(12) United States Patent
Colarusso et al.

(10) Patent No.: US 7,119,073 B2
(45) Date of Patent: Oct. 10, 2006

(54) PEPTIDES AND THEIR USE AS INHIBITORS OF HEPATITIS C VIRUS NS3 PROTEASE

(75) Inventors: Stefania Colarusso, Pomezia (IT); Cristina Gardelli, Pomezia (IT); Benjamin Gerlach, Arco (IT); Steven Harper, Pomezia (IT); Uwe Koch, Pomezia (IT); Victor Giulio Matassa, Hirschberg (DE); Ester Muraglia, Pomezia (IT); Frank Narjes, Pomezia (IT); Jesus Maria Ontoria Ontoria, Pomezia (IT); Alessia Petrocchi, Pomezia (IT); Simona Ponzi, Pomezia (IT); Ian Stansfield, Pomezia (IT); Vicenzo Summa, Pomezia (IT)

(73) Assignee: Istituto Di Ricerche Di Biologia Molecolare P. Angeletti SpA, Pomezia (IT)

( * ) Notice: Subject to any disclaimer, the term of this patent is extended or adjusted under 35 U.S.C. 154(b) by 47 days.

(21) Appl. No.: 10/473,443

(22) PCT Filed: Mar. 26, 2002

(86) PCT No.: PCT/EP02/03435

§ 371 (c)(1),
(2), (4) Date: Mar. 3, 2004

(87) PCT Pub. No.: WO02/079234

PCT Pub. Date: Oct. 10, 2002

(65) Prior Publication Data

US 2004/0142876 A1    Jul. 22, 2004

(30) Foreign Application Priority Data

Mar. 29, 2001  (GB) ................................ 0107924

(51) Int. Cl.
| | | |
|---|---|---|
| A61K 38/06 | (2006.01) | |
| A61K 38/07 | (2006.01) | |
| C07K 5/08  | (2006.01) | |
| C07K 5/10  | (2006.01) | |
| C07K 7/04  | (2006.01) | |
| A61K 38/00 | (2006.01) | |
| C07K 2/00  | (2006.01) | |

(52) U.S. Cl. .................... 514/18; 514/17; 530/331; 530/330; 530/329

(58) Field of Classification Search .............. None
See application file for complete search history.

(56) References Cited

U.S. PATENT DOCUMENTS 4,297,346 A * 10/1981 Rips et al. .................. 514/19

FOREIGN PATENT DOCUMENTS

| WO | WO 9206108 A1 * | 4/1992 |
|---|---|---|
| WO | WO 98/46630 A | 10/1998 |
| WO | WO 99/64442 A | 12/1999 |

OTHER PUBLICATIONS

Llinas-Brunet, M. et al., "Peptide-Based Inhibitors of the Hepatitis C Virus Serine Protease", 1998, Bioorganic & Medicinal Chemistry Letters, vol. 8, No. 13, pp. 1713-17318.

Bailey, M.D. et al., "Novel C-Terminal Carboxylic Acid Tri-Peptide Inhibitors of Hepatitis C Virus Serine Protease", American Chemical Society, vol. 220, pp. MED188 XP00964834 (2000).

Landro, J.A. et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", 1997, Biochemistry, vol. 35, No. 11, pp. 9340-9348.

Llinas-Brunet M. et al., "Studies on the C-Terminal of Hexapeptide Inhibitors of the Hepatitis C Virus Serine Protease", 1998, Biorganic Medicinal Chemistry Letters 8, pp. 2719-2724.

Beilstein Registry No. 8123814, XP-002206365, reference to: Eaton S.R., et al., J. Med. Chem., 1998, vol. 41, No. 22, pp. 4329-4342.

Beilstein Registry No. 5835997, XP002206366, reference to: Rich, D.H., et al., J. Med. Chem., 1992, vol. 35, No. 21, pp. 3803-3812.

* cited by examiner

Primary Examiner—Bruce R. Campbell
Assistant Examiner—Andrew D. Kosar
(74) Attorney, Agent, or Firm—Kenneth R. Walton; Valerie J. Camara

(57) ABSTRACT

Compounds of formula (I), and pharmaceutically acceptable salts and esters thereof: (I); wherein Q, R2, X, Y and Z are as defined herein; are inhibitors of the hepatitis C virus (HCV) NS3 protease

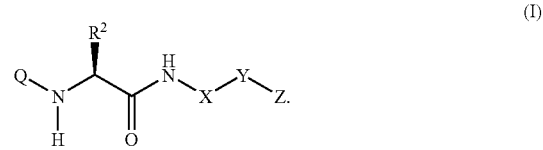

20 Claims, No Drawings

PEPTIDES AND THEIR USE AS INHIBITORS OF HEPATITIS C VIRUS NS3 PROTEASE

FIELD OF THE INVENTION

This invention relates to compounds which can act as inhibitors of the hepatitis C virus (HCV) NS3 protease, to uses of such compounds and to their preparation.

BACKGROUND OF THE INVENTION

The hepatitis C virus (HCV) is the major causative agent of parenterally-transmitted and sporadic non-A, non-B hepatitis (NANB-H). Some 1% of the human population of the planet is believed to be affected. Infection by the virus can result in chronic hepatitis and cirrhosis of the liver, and may lead to hepatocellular carcinoma. Currently no vaccine nor established therapy exists, although partial success has been achieved in a minority of cases by treatment with recombinant interferon-α, either alone or in combination with ribavirin. There is therefore a pressing need for new and broadly-effective therapeutics.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions.

Previous research has identified classes of peptides, in particular hexapeptides, showing degrees of activity in inhibiting the NS3 protease. The aim of the present invention is to provide further compounds which exhibit similar, and if possible improved, activity.

Llinàs-Brunet et al (Bioorganic Medicinal Chemistry Letters 8 (1998) 2719–2724) described hexapeptide inhibitors of HCV. The activity of their inhibitors could be improved when the C-terminal carboxylic acid group was "activated" as an amide. Notably, benzylamides are exemplified in this document. However, derivatization as an amide was associated with loss of specificity of inhibition. The authors of this reference made no suggestion that peptides shorter than six amino acids long could be of any utility.

SUMMARY OF THE INVENTION

The present inventors have discovered that certain peptidic phenethylamides and related compounds are effective inhibitors of NS3 protease. Although not wishing to be bound by any particular theory, the inventors believe that these compounds are non-covalent inhibitors of serine protease which may be involved in a partial bond with the serine hydroxyl group of the enzyme. This distinguishes the compounds of the invention from compounds previously suggested as serine protease inhibitors and which rely on formation of a covalent bond with the serine hydroxyl group.

The inventors have found that by including a phenethylamide or analogous group at the C-terminus the activity of hexapeptide inhibitors may be improved. However, in some embodiments molecules containing less than six amino acids retain useful activity because of the presence of the phenethylamide, or analogous, group at the C-terminus.

According to the present invention there is provided a compound of Formula (I), or a pharmaceutically acceptable salt or ester thereof:

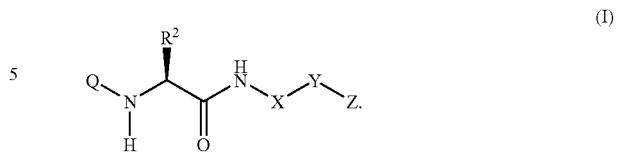

wherein Q is selected from the group consisting of:

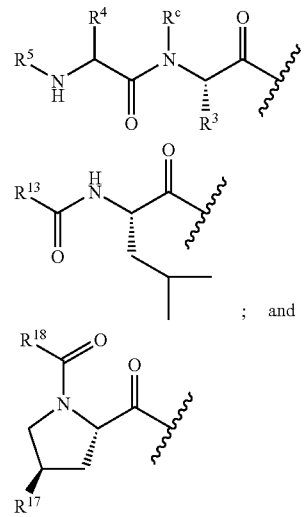

wherein X is —CH$_2$— or —O—;

Y is a group of formula —C(R$^a$)$_2$— where each R$^a$ is independently selected from hydrogen, hydroxyl, carboxylic acid, lower alkyl (such as methyl), aryl (such as phenyl), heteroaryl, aralkyl or heteroaralkyl, or the two R$^a$ groups together form a cycloalkyl group containing 3 to 7, preferably 3 to 5 carbon atoms;

Z is a substituted or unsubstituted aryl or heteroaryl group;

R$^2$ is a lower alkyl group, optionally substituted with one or more fluorine atoms, or is —CH$_2$SH;

R$^3$ is an optionally substituted alkyl, aryl, heteroaryl, aralkyl, or heteroaralkyl group containing from 2 to 16 carbon atoms, or together with R$^c$ forms a ring including the nitrogen atom which bears R$^c$;

R$^c$ is hydrogen or a lower alkyl group or together with R$^3$ forms a ring;

R$^4$ is an alkyl, alkenyl, aralkyl, heteroaralkyl, aryl or heteroaryl group containing from 2 to 16 carbon atoms or is an acidic group;

R$^5$ is selected from (R$^6$)$_2$NCO—, R$^7$CO—, R$^7$OCO—, R$^7$NHCO—, R$^7$CO.CO—, R$^7$S(O)$_2$— and R$^8$ pep where "pep" is an amino acid, di- or tri- peptide;

each R$^6$, independently, is selected from hydrogen and optionally substituted, optionally interrupted lower alkyl or lower alkenyl, aryl, heteroaryl, aralkyl or heteroaralkyl groups, or the two R$^6$ taken together form a four to seven membered ring optionally containing one or more other heteroatoms in addition to the nitrogen atoms to which the R$^6$ groups are bonded;

R$^7$ is an optionally substituted, optionally interrupted alkyl, alkenyl, aralkyl, heteroaralkyl, aryl or heteroaryl group containing from 1–18 preferably 1 to 14 carbon atoms, particularly, 1–8 carbon atoms;

$R^8$ is a group of formula $(R^6)_2NCO—$, $R^7CO—$, $R^7OCO—$, $R^7NHCO—$, $R^7COCO—$, and $R^7S(O)_2—$;

"pep" if present is an amino acid, di, or tri peptide of formula C—B-A;

wherein A is selected from naturally and non-naturally occurring amino acids having a hydrophobic side chain containing 1–20 carbon atoms;

B may be absent, in which case C will also be absent, but if present is selected from naturally or non-naturally occurring amino acids having a side chain which includes an acidic functionality;

C may be absent, either by itself or together with B, but if present may be selected from naturally or non-naturally occurring amino acids containing an acidic functionality;

$R^{13}$ is a group containing up to 25 carbon atoms, 0–5 oxygen atoms, 0–3 nitrogen atoms, 0–2 sulphur atoms and up to 9 other heteroatoms which may be the same or different;

$R^{17}$ is hydrogen, a lower alkyl, lower alkenyl, aryl, heteroaryl, aralkyl, heteroaralkyl, hydroxyl, alkoxy, aryloxy, aralkoxy, heteroaralkoxy, thioether, sulfonyl or sulfoxide group; and $R^{18}$ is a group containing up to 25 carbon atoms, 0–5 oxygen atoms, 0–3 nitrogen atoms, 0–2 sulphur atoms and up to 9 other heteroatoms which may be the same or different.

DETAILED DESCRIPTION OF THE INVENTION

Definitions

In the discussion of the invention which follows certain terms are used repeatedly. Therefore, we seek to define each at the outset. Where definitions in the text differ from those given here it should be understood that the possibilities set out are those which are preferred among the broader definitions set out here.

By "lower alkyl" and "lower alkoxy" are intended groups having from 1 to 10, preferably 1 to 6, most preferably 1 to 4 carbon atoms. "Lower alkenyl" groups have from 2 to 10, preferably 2 to 6 carbon atoms.

The term "aryl" as used herein implies an aromatic ring optionally fused, e.g. benzofused, with one to three cycloalkyl, aromatic, heterocyclic or heteroaromatic rings. Preferred groups containing a carbocyclic aromatic radical have from 6 to 14 more preferably 6 to 10 carbon atoms. Examples of such groups include phenyl and naphthyl. The term "heteroaryl" as used herein implies a heteroaromatic ring which is optionally fused with one to three cycloalkyl, aromatic, heterocyclic or heteroaromatic rings. Heteroaryl groups, in general, include a 3 to 7 membered heterocyclic aromatic ring consisting of one or more carbon atoms and from one to four heteroatoms selected from nitrogen, oxygen and sulphur.

Lower alkyl and lower alkoxy groups as defined above may, optionally, carry one or more aryl or heteroaryl substituent. The result is an aralkyl, heteroaralkyl, aralkyloxy or heteroaralkyloxy group. Examples of aralkyl- and heteroaralkyl groups include, but are not limited to, those of formula:

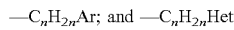
—$C_nH_{2n}$Ar; and —$C_nH_{2n}$Het where "Ar" designates aryl and "Het" designates heteroaryl and n is an integer of 1 to 10. Examples of aralkyloxy- and heteroaralkyloxy-groups include but are not limited to, those of formula:

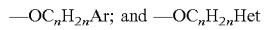
—$OC_nH_{2n}$Ar; and —$OC_nH_{2n}$Het where "n", "Ar" and "Het" are as defined above. Preferred aralkyl, heteroaralkyl, aralkyloxy- and heteroaralkyloxy-groups generally include from 2 to 20, say from 4 to 15 carbon atoms.

Optional substituents are not particularly limited but may be selected from the following list: lower alkyl or alkenyl, aryl, heteroaryl, lower alkoxy, aryloxy or aralkyloxy, heteroaryloxy or heteroaralkyloxy, amino, nitro, halo, hydroxy, carboxylic acid, acyl, formyl, sulphonamide, acylsulphonamide, ester, amide, cyano, and trihalomethyl groups. As appropriate an optional substituent may itself optionally be interrupted and/or be substituted by another substituent.

Where a group is described as "optionally interrupted" it may contain at least one of the following:

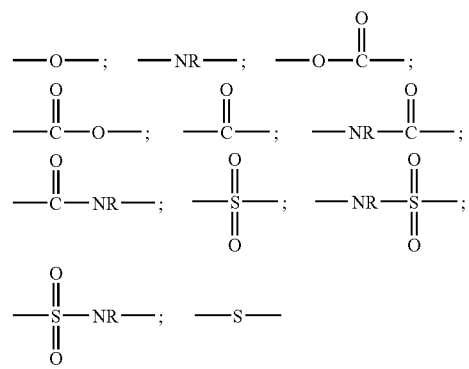

where R is hydrogen, or an alkyl, e.g. lower alkyl, alkenyl, e.g. lower alkenyl, aryl, heteroaryl, aralkyl or heteroaralkyl group.

Where specific stereochemistries are indicated in the formulae herein, these are the preferred stereochemistries. It should be understood that enantiomeric and diastereomeric forms of each molecule are within the scope of the invention.

General

The compounds of the present invention all have in common a "C-terminal portion" of the following formula:

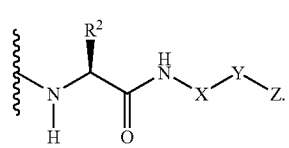

(I)

Of this, the fragment:

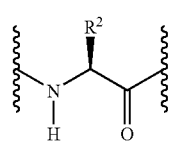

may be thought of as derived from an α-amino acid of formula:

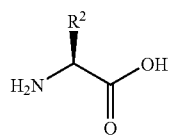

In the compounds of the invention this amino acid is chosen to be identical to, or to mimic, the amino acid found at the so-called P1 position at the trans-cleavage sites of the natural substrates for HCV NS3 serine protease.

Thus generally, $R^2$ is a lower alkyl group, optionally substituted with one or more fluorine atoms, or is the side chain of cysteine (—$CH_2SH$). Apart from the cysteine side chain, other preferred $R^1$ groups are —$CH_2$—$CHF_2$ (the side chain of difluoroaminobutyric acid), —$CH_2CF_3$ (the side chain of trifluoroaminobutyric acid) and —$CH_2CH_3$ (the side chain of aminobutyric acid).

X is —$CH_2$— or —O—;

Y is a group of formula —$C(R^a)_2$— where each $R^a$ is independently selected from hydrogen, hydroxyl, carboxylic acid, lower alkyl (such as methyl), aryl (such as phenyl), heteroaryl aralkyl or heteroaralkyl, or the two $R^a$ groups together form a cycloalkyl group containing 3 to 7, preferably 3 to 5 carbon atoms.

Preferred combinations —X—Y— are —O—$CH_2$— and —$CH_2CH_2$—, of which the latter is the more preferred.

Z is a substituted or unsubstituted aryl or heteroaryl group.

Preferably, it is an optionally substituted phenyl group, although other preferred possibilities include optionally substituted indolyl, thienyl, naphthyl, and pyridyl groups.

Where present, the possible substituents may be selected from a wide range, such as set out above under the heading "definitions". Particularly, preferred substituents on phenyl are the halogens, especially chlorine and fluorine, carboxylic acid (possibly in the form of an ester, e.g. lower alkyl ester), acylsulphonamide, and tetrazole. Another preferred substituent has the formula:

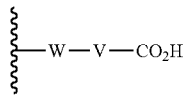

which, again, may be in the form of a lower alkyl ester. W is selected from —$CH_2$—, —O—, and —NH— and V is selected from —$CH_2$— and —$CHR^b$— where $R^b$ is an optionally substituted lower alkyl, lower alkenyl, aralkyl, heteroaralkyl, aryl, or heteroaryl group. Alternatively W and V together form a carbon carbon double bond, preferably with a trans configuration.

In the case where the Z group is phenyl and this is substituted with an acidic substituent (carboxylic acid, acyl sulphonamide or tetrazole), the acidic group is preferably at the 4-position of the phenyl group (i.e. para to the remainder of the molecule. The substituent —W—V—$CO_2H$ is however preferably at the 3-position, although substitution at the 4-position is also possible. Substitution by halogens, particularly fluorine and chlorine is preferably at the position(s) ortho- to the rest of the molecule—i.e. at the 2- and/or 6-position. Particularly preferred compounds have an acidic group (carboxylic acid, tetrazole, acylsulphonamide) at the 4-position and either 2 fluorines (at positions 2- and 6-) or a chlorine in the 2-position.

In addition to the characteristic "C-terminal portion" illustrated above at (I), the compounds of the invention include an "N-terminal portion" linked to the "C-terminal portion". This is chosen such that the molecule as a whole is capable of binding to the NS3 protease of HCV, and in particular in the S1 binding pocket of the enzyme.

The extent to which the compounds bind to the NS3 serine protease is reflected by their $IC_{50}$s in inhibition assays, for instance as described herein. Preferably, the $IC_{50}$ is 100 μM or less, particularly 10 μm or less and, ideally 100 nM or less. However, activity in an inhibition assay should not be thought of as the sole indicator of usefulness. A molecule having relatively low activity may be useful for another reason—e.g. because of its small size or relative lack of peptidic character which render it resistant to degradation when taken orally.

It is to be understood that pharmaceutically acceptable salts and esters of the compounds described herein are within the scope of the invention.

Examples of the compounds of the present invention fall into several groups, or aspects, and these are considered in some more detail below.

Compounds of the First Aspect

According to a first aspect of the present invention there are provided compounds of Formula (1):

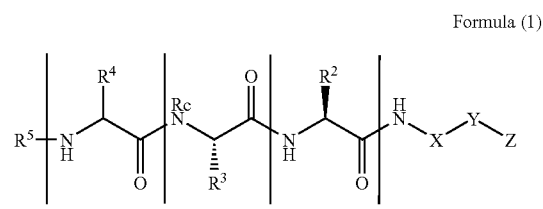

Formula (1)

and pharmaceutically acceptable salts and esters thereof.

In this formula, the groups $R^2$, X, Y and Z are as defined above, and the groups described above as preferred are also preferred in Formula (1).

The various other groups present in this molecule are considered in turn below.

$R^3$

There are generally two possibilities for $R^3$. The first is that it is a side chain whose distal end is free. Alternatively, together with Rc it forms a ring which includes the adjacent nitrogen atom.

When $R^3$ is a side chain it is generally an optionally substituted (e.g. by fluorine or carboxylic acid group) alkyl, aryl, heteroaryl, aralkyl or heteroaralkyl group, containing from 2 to 16 carbon atoms. Preferred $R^3$ groups are unsubstituted hydrocarbons, in particular alkyl groups, such as the side chains of alanine (—$CH_3$), valine (—$CH(CH_3)_2$)) leucine (—$CH_2CH(CH_3)_2$), isoleucine (—$CH(CH_3)(C_2H_5)$) or cyclohexylalanine

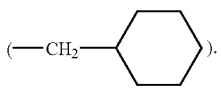

When R³ together with R^c form a ring including a nitrogen atom the ring is desirably 4 to 7 membered, particularly 5-membered and may be saturated or unsaturated. Optionally, the ring is substituted, for instance by one or more lower alkyl, lower alkenyl, aryl, heteroaryl, aralkyl, or heteroaralkyl groups. Substituents present on adjacent ring carbons may together form a further 4 to 7 membered ring. Other possible substituents in the ring include, among others, hydroxyl, alkoxy (such as lower alkoxy), aryloxy, heteroaryloxy, aralkoxy, heteroaralkoxy thioether, aryl-, or alkyl-, sulfonyl and aryl-, or alkyl-, sulfoxide groups.

Preferably, when R³ together with R^c form a ring then the amino acid residue including the ring is a proline residue of formula:

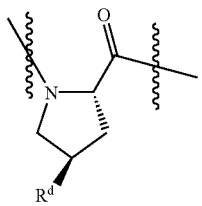

wherein $R^d$ is hydrogen or, more preferably is one of the substituents discussed above—i.e. it is preferably selected from lower alkyl, lower alkenyl, aryl, heteroaryl, aralkyl, or heteroaralkyl groups, a hydroxyl, alkoxy, aryloxy, heteroaryloxy, aralkoxy, heteroaralkoxy, thioether, sulfonyl and sulfoxide groups. Particularly, preferred substituents are phenyl, cyclohexyl, benzyl ether, benzyl thioether, and the thioethers, sulfones and sulfoxides formed with phenyl, cyclohexyl or n-propyl groups.

R^c

R^c is preferably hydrogen or, as described above may form a ring with R³. Less preferably it may be a lower alkyl group, especially methyl.

R⁴

R⁴ is an alkyl, alkenyl, aralkyl, heteroaralkyl, aryl or heteroaryl group containing from 2 to 16 carbon atoms. Preferably it is a lower alkyl group, for instance the side chain of alanine (—CH₃), leucine (—CH₂—CH(CH₃)₂), isoleucine (—CH(CH₃)(C₂H₅), or valine (—CH(CH₃)₂), a cyclopentyl or t-butyl group. Of these the side chain of valine is preferred. Alternatively, R⁴ may be an acidic group, e.g. a carboxyalkyl group containing from 2 to 8 carbon atoms, such as the side chain of aspartic acid (—CH₂COOH) or, more preferably, glutamic acid (—CH₂CH₂COOH).

R⁵

R⁵ is selected from (R⁶)₂NCO—, R⁷CO—, R⁷OCO—, R⁷NHCO—, R⁷CO.CO—, R⁷S(O)₂— and R⁸ pep where "pep" is an amino acid, di- or tri- peptide.

Each R⁶, independently, is selected from hydrogen and optionally substituted, optionally interrupted lower alkyl or lower alkenyl, aryl, heteroaryl, aralkyl or heteroaralkyl groups, or the two R⁶ taken together form a four to seven membered ring optionally containing one or more other heteroatoms in addition to the nitrogen atoms to which the R⁶ groups are bonded.

R⁷ is an optionally substituted, optionally interrupted alkyl, alkenyl, aralkyl, heteroaralkyl, aryl or heteroaryl group containing from 1–18 preferably 1 to 14 carbon atoms, particularly, 1–8 carbon atoms.

R⁸ is a group of formula (R⁶)₂NCO—, R⁷CO—, R⁷OCO—, R⁷NHCO—, R⁷COCO—, and R⁷S(O)₂—

"pep" if present is an amino acid, di, or tri peptide of formula C—B-A wherein A is selected from naturally and non-naturally occurring amino acids having a hydrophobic side chain containing 1–20 carbon atoms. Possibilities include leucine, methionine, isoleucine or, more preferably, diphenylalanine.

B may be absent. If it is, then C will also be absent. Where present, B is selected from naturally or non-naturally occurring amino acids having a side chain which includes an acidic functionality. Preferred examples are glutamic and aspartic acid, with the former being particularly preferred.

C may be absent, either by itself or together with B. Where present it may be selected from naturally or non-naturally occurring amino acids containing an acidic functionality. Aspartic acid is preferred, although glutamic acid is another possibility.

Preferably "pep" is absent and the compounds are tripeptides.

Preferred R⁵ groups are those of formula R⁶OCO—.

Preferred R⁷ groups are t-butyl and isobutyl.

Compounds of this aspect of the invention each include several asymmetric carbon atoms and they can, therefore, exist in the form of optically pure diastereoisomers, mixtures of diastereoisomers, diastereoisomeric racemates or mixtures of diatereoisomeric racemates. All of these possible forms are included within the scope of the present invention. However, it is preferred that all amino acids or amino acid analogues have the L-configuration. Nevertheless, some deviation from this generalisation can be tolerated.

Specific examples of preferred compounds of this aspect of the invention are shown in Tables 1 to 5.

Compounds of the Second Aspect

In a second aspect, the present invention is concerned with dipeptides, and pharmaceutically acceptable salts and esters thereof. At the C-terminus, these resemble the tri- and higher peptides described above. However, instead of a third amino acid (providing the side group R⁴ in formula (1), the molecules contain a "cap".

One preferred group of compounds includes dipeptides of the following formula:

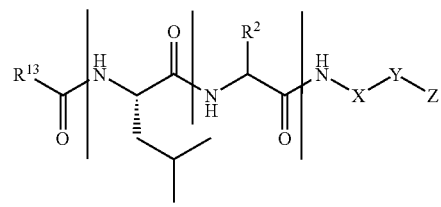

In this formula, X, Y, Z and R² are as defined above. Preferred examples of these groups described above are also preferred in this embodiment. In particular, X and Y are preferably both —CH₂— and R² is preferably —CH₂CHF₂ or —CH₂SH.

R¹³ is a group containing up to 25, preferably 4–21, particularly 4–16 carbon atoms and 0–5 oxygen atoms, 0–3 nitrogen atoms, 0 to 2 sulphur atoms, and up to 9 other heteroatoms, such as halogen atoms) which may be the same or different. Preferred $R_{13}$ groups contain an acidic functionality, preferably a carboxylic acid group which may be in prodrug form—e. g. esterified.

Substituent groups $R^{13}$ preferably include a relatively hydrophobic portion such as a cycloalkyl, aryl, heteroaryl, aralkyl, or heteroaralkyl group each of which may, optionally, be substituted.

Preferred examples of the group $R^{13}$ include indolines of formula:

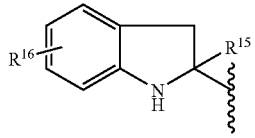

and tetrahydroquinolines of formula:

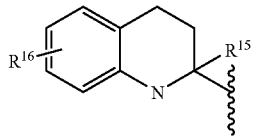

where $R^{15}$ is hydrogen, an optionally branched, optionally interrupted and optionally substituted lower alkyl or lower alkenyl group, or an optionally substituted aralkyl or heteroaralkyl group and $R^{16}$ is hydrogen or an optionally substituted and optionally interrupted lower alkoxy, aryloxy or heteroaryloxy group.

A preferred substituent on $R^{15}$ is —$CO_2H$, optionally in the form of a lower alkyl ester. When $R^{15}$ is an aralkyl group it is preferably an optionally substituted benzyl or thienylmethyl group. Preferred substituents in the aryl group include halogens, especially chlorine, lower alkoxy (e.g. OMe) and aryloxy (e.g. PhO—) groups, cyano, and carboxylic acid groups. Carboxylic acid groups, optionally in the form of lower alkyl esters are especially preferred.

Especially preferred $R^{15}$ groups include:

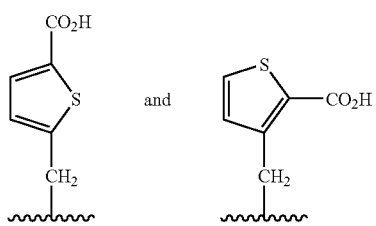

Another preferred example of the group $R^{13}$ has the following formula:

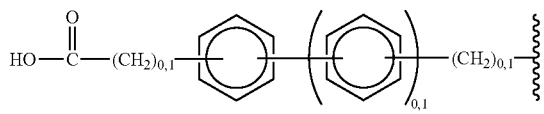

Once again, the carboxylic acid group may be esterified for instance as a lower alkyl ester such as a methyl ester. Alternatively, the carboxylic acid group may be amidated, e.g. as —$CONH_2$.

Preferred groups of this type have the formula:

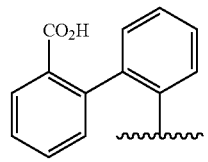

Other possible $R^{13}$ groups are listed under the heading "$R^3$" at Table 7. Each $R^{13}$ exemplified may be used in conjunction with any of the groups "$R_2$" and "$R_1$" listed in the table.

Another preferred group of dipeptides includes proline, or a proline derivative at the P2 position. Compounds in this category have the formula:

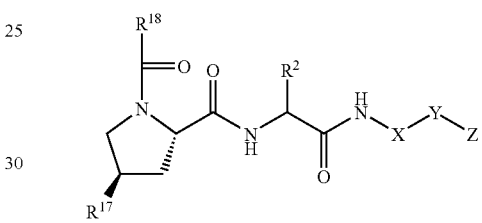

where X, Y, Z and $R^2$ are as defined above. Preferred examples of these groups, described above are also preferred in this embodiment. In particular, X and Y are preferably both —$CH_2$— and $R^2$ is preferably $CH_2CHF_2$ or $CH_2SH$. Z is preferably 2,6-difluoro-4-carboxy-phenyl-.

$R^{17}$ is hydrogen or more preferably is a lower alkyl, lower alkenyl, aryl, heteroaryl, aralkyl or heteroaralkyl group, a hydroxyl, alkoxy, aryloxy, heteroaryloxy, aralkoxy, heteroaralkoxy thioether, sulfonyl or sulfoxide group. Particularly preferred substituents are phenyl, cyclohexyl, benzyl ether, benzyl thioether, and the thioethers, sulfones and sulfoxides formed with phenyl, cyclohexyl or n-propyl groups. Miscellaneous examples of this group can be found at table 6.

$R^{18}$ is a group containing up to 25, preferably 4–21, particularly 4 to 16 carbon atoms and 0 to 5 oxygen atoms, 0–3 nitrogen atoms, 0–2 sulphur atoms and up to 9 other heteroatoms, such as halogen atoms, which may be the same or different.

Some examples of suitable $R^{18}$ groups include the following:

where $R^{19}$ is an alkyl group, preferably a lower alkyl group, including branched especially α-branched alkyl groups such as isopropyl or t-butyl groups, a $C_3$–$C_7$ cycloalkyl group, or anoptionally substituted aryl group. Preferred substituents include $C_{1-8}$ alkoxy, halogen or —$CF_3$.

Another suitable $R^{18}$ group has the formula:

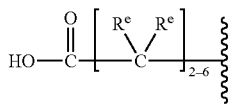

wherein each $R^e$ is independently selected from hydrogen, lower alkyl (especially methyl), lower alkenyl, lower alkoxy, optionally substituted aryl, heteroaryl, aralkyl or heteroaralkyl groups (such as those substituted with halogen, —$CF_3$ or lower alkyl or alkoxy groups) or two $R^e$ taken together result in the formation of a three to seven membered aliphatic or aromatic ring which optionally contains at least one heteroatom. In the case where two $R^e$ taken together result in the formation of a ring containing unsaturation, especially an aromatic ring, then other $R^e$ may be absent.

Optionally one or more groups

may be replaced by —O—. Preferably no more than one such group is replaced.

A preferred subclass of this group of compounds is

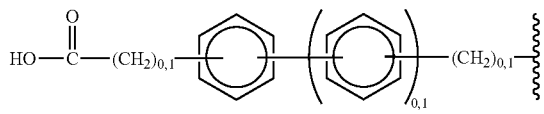

such as

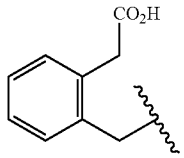

The carboxylic acid group in any of this preferred class of compounds may be esterified for instance as a lower alkyl ester such as a methyl ester.

The —OH group of the carboxyl acid group may also optionally be replaced by an —$SO_2NH$— group, especially by Ph—$SO_2$—NH—.

Examples of other groups suitable as substitiaent $R^{18}$ are shown under the heading "$R_4$" in Table 6. Each of the exemplified groups may be used in conjunction with any of the other groups exemplified in the table.

Other Aspects of the Invention

According to a third aspect, the present invention provides a compound or derivative according to the first aspect, for use in any therapeutic method, preferably for use in inhibiting the HCV NS3 protease, and/or for use in treating or preventing hepatitis C or a related condition. By "related condition" is meant a condition which is or can be caused, directly or indirectly, by the hepatitis C virus, or with which the HCV is in any way associated.

According to a fourth aspect the present invention provides the use of a compound or derivative according to the first aspect in the manufacture of a medicament for the treatment or prevention of hepatitis C or a related condition.

A fifth aspect of the invention provides a pharmaceutical composition which includes one or more compounds or derivatives according to the first aspect.

The composition may also include pharmaceutically acceptable adjuvants such as carriers, buffers, stabilisers and other excipients. It may additionally include other therapeutically active agents, in particular those of use in treating or preventing hepatitis C or related conditions.

The pharmaceutical composition may be in any suitable form, depending on the intended method of administration. It may for example be in the form of a tablet, capsule or liquid for oral administration, or of a solution or suspension for administration parenterally.

According to a sixth aspect of the invention, there is provided a method of inhibiting HCV NS3 protease activity, and/or of treating or preventing hepatitis C or a related condition, the method involving administering to a human or animal (preferably mammalian) subject suffering from the condition a therapeutically or prophylactically effective amount of a composition according to the fourth aspect of the invention, or of a compound or derivative according to the first aspect. "Effective amount" means an amount sufficient to cause a benefit to the subject or at least to cause a change in the subject's condition.

The dosage rate at which the compound, derivative or composition is administered will depend on the nature of the subject, the nature and severity of the condition, the administration method used, etc. Appropriate values can be selected by the trained medical practitioner. Preferred daily doses of the compounds are likely to be of the order of about 1 to 100 mg. The compound, derivative or composition may be administered alone or in combination with other treatments, either simultaneously or sequentially. It may be administered by any suitable route, including orally, intravenously, cutaneously, subcutaneously, etc. Intravenous administration is preferred. It may be administered directly to a suitable site or in a manner in which it targets a particular site, such as a certain type of cell—suitable targeting methods are already known.

A seventh aspect of the invention provides a method of preparation of a pharmaceutical composition, involving admixing one or more compounds or derivatives according to the first aspect of the invention with one or more pharmaceutically acceptable adjuvants, and/or with one or more other therapeutically or prophylactically active agents.

Compounds of the present invention may be prepared by reacting protected form of the P1 amino acid:

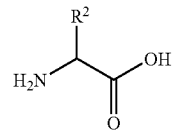

with a compound of formula $H_2N$—X—Y-Z.

The resulting compound may subsequently be extended towards the N-terminus by conventional methods of synthesis employing protected amino acids, peptides or "capped" amino acids.

The invention provides, according to an eighth aspect, a method as described above for preparing a compound according to the first or second aspect.

EXAMPLES

Embodiments of the invention are described below by way of example only.

The following abbreviations are used in the examples and tables:

| | |
|---|---|
| Ac: | acetate; |
| 4-AMP: | 4-aminomethylpiperidine; |
| BEMP: | 2-tert.-butylimino-2-diethylamino-1,3-dimethyl-perhydro-1,3,2-diazaphosphorine; |
| Bn: | benzyl; |
| Boc: | tert-butyloxycarbonyl[Me3CO(O)]; |
| i-Boc: | isobutyloxycarbonyl[Me$_2$CHCH$_2$CO(O)]; |
| Cbz: | benzyloxycarbonyl; |
| Cha: | L-cyclohexylalanine; |
| Cpg: | L-cyclopentylglycine; |
| DCM: | dichloromethane; |
| DIEA: | diisopropylethyl amine; |
| Dif: | L-diphenylalanine; |
| DMAP: | N,N-dimethylaminopyridine; |
| DMF: | dimethylformamide; |
| DMSO: | dimethylsulfoxide; |
| EDC: | 1-ethyl-3-(3'-dimethylaminopropyl)carbodiimide hydrochloride; |
| Et: | ethyl; |
| EtOAc: | ethyl acetate; |
| Et$_2$O: | diethyl ether; |
| Fmoc: | fluorenylmethyloxycarbonyl; |
| HATU: | [O-7-azabenzotriazol-1-yl)-1,1,3,3-tetramethyluronium hexafluorophosphate]; |
| HOBt: | N-hydroxybenzotriazole; |
| KHMDS: | potassium bis(trimethylsilyl)amide; |
| LDA: | lithium diisopropyl amide; |
| mCPBA: | meta chloroperoxybenzoic acid; |
| Me: | methyl; |
| NBS: | N-bromosuccineamide; |
| NMM: | N-methyl morpholine; |
| Ph: | phenyl; |
| pip: | piperidine; |
| PPTs: | pyridinium-para-toluenesulfonate; |
| Pr: | propyl; |
| RP-HPLC: | reversed phase high-pressure liquid chromatography; |
| RT: | retention time; |
| TES: | triethylsilane; |
| TFA: | trifluoroacetic acid; |
| THF: | tetrahydrofuran; |
| TIPS: | triisopropylsilane; |
| TLC: | thin-layer chromatography; |
| TMEDA: | N,N,N',N'-tetramethyl-ethylendiamine; |
| TsCl: | tosyl chloride. |

Nuclear magnetic resonance (NMR) spectra were recorded on a Bruker AMX 300 or AMX 400 spectrometer. The chemical shifts (δ) are reported in ppm relative to internal tetramethylsilane or the residual solvent peak.

Mass spectral data were obtained on a Perkin Elmer API 100 in negative or positive ionization mode. Organic extracts were usually dried over sodium sulfate, the drying agent was removed by filtration and the solvents evaporated on a rotary evaporator under reduced pressure.

Flash chromatography was carried out on silca gel according to Still's published procedure (W. C. Still et al., J. Org. Chem. 1978, 43, 2923) or on Flash chromatography systems with prepacked columns (Biotage corporation).

Preparative RP-HPLC was carried out with a Waters Delta Prep 4000 separation module, equipped with a Waters 486 absorption detector. A SymmetryPrep C18 column (7 micron, 100 A, 19×150 mm, Waters) was routinely used. Compounds were eluted with gradients of water (solvent A) and acetonitrile (solvent B) both containing 0.1% TPA (v/v) at 17 mL/min.

General Scheme for Synthesis of Compounds

The compounds of the present invention were synthesized according to a general process illustrated in the scheme below(where PG is an amino protecting group, usually a carbamate):

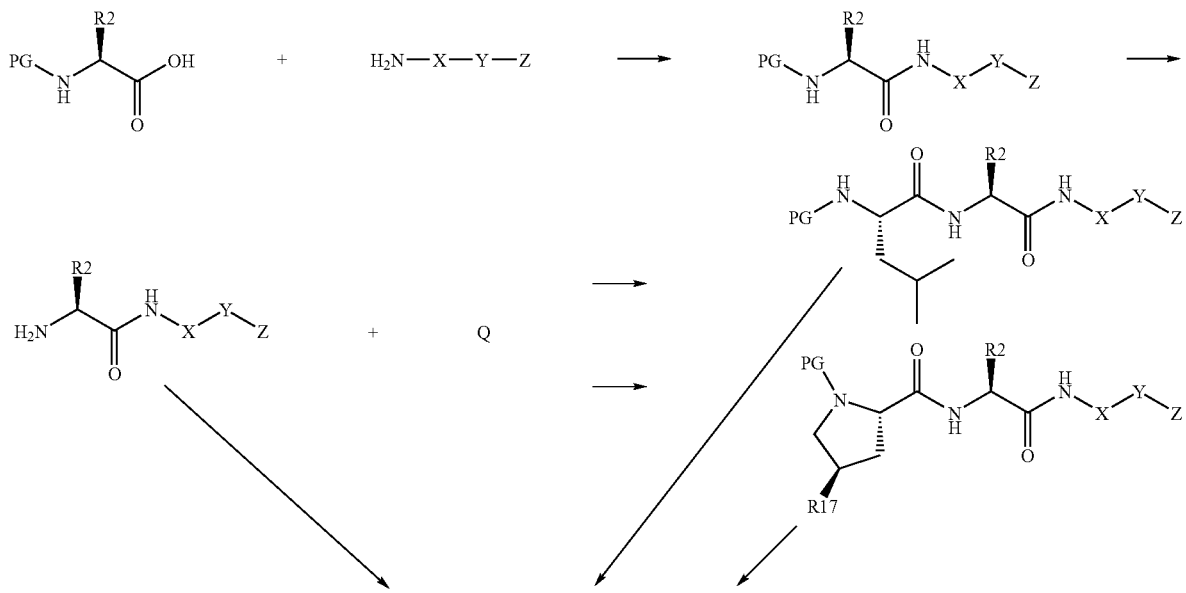

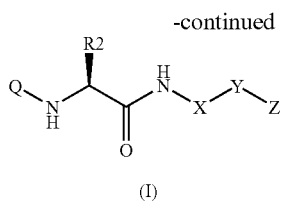

(I)

Briefly, an amine H₂N—X—Y-Z—i.e. a P' building block—(either commercially available or prepared as laid out in the experimental section), was coupled to an amino acid containing R²—i.e. a P₁ building block—using well known peptide coupling techniques. After removal of the PG group by standard techniques, a compound Q can be coupled using peptide coupling techniques to give a compound of formula (I). Alternatively, the compound can be elongated with another amino acid using the methods described. This deprotection and coupling procedure is repeated until the desired compound is obtained. Different capping groups (as in $R^{13}C=O$ or $R^{18}C=O$) were either introduced by standard amide bond formation or by acylation of the free amino group.

Generally these reactions can be carried out in solution phase or using solid phase methodology, where the group $R^2$ is linked to the resin (see examples 19 and 27).

The detailed examples below describe the synthesis of certain "building blocks". Those building blocks required for synthesis of the compounds of tables 1 to 7 and whose detailed synthesis is not described below are either readily commercially available, or else can by synthesized by techniques known to the person skilled in the art and analogous to those described below. The building blocks whose synthesis are described are referred to as P', P₁, P₂ or P₃ building blocks by analogy with the terminology applied to amino acids at the cleavage site of the natural substrate for NS3.

P' Building Blocks

Example 1

Synthesis of 3-(2-aminoethyl)thiophene (1)

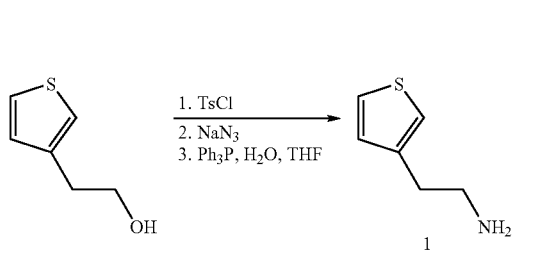

2-(3-Thienyl)ethyl alcohol (2.62 g, 20.4 mmol) was dissolved in DCM (100 mL) and cooled to 0° C. After addition of triethylamine (3.10 g, 30.6 mmol) and solid tosyl chloride (3.89 g, 20.4 mmol), the reaction was stirred at room temperature overnight. DCM was evaporated, the mixture was diluted with EtOAc and washed subsequently with aqueous hydrochloric acid (1 N), water, saturated sodium hydrogen carbonate and brine. Drying and evaporation afforded an oil, which was dissolved in anhydrous DMF (20 mL). Sodium azide (2.65 g, 40.8 mmol) was added and the mixture heated to 40° C. for 3 h. After cooling to room temperature, EtOAc was added and the solution was washed with water (4×) and brine, then dried and evaporated. The resulting oil was filtered over silica gel (100 g) with the aid of PE/EtbAc (10:1) to obtain 2-(3-thienyl)ethyl azide (2.45 g, 78%) as a colorless liquid. ¹H-NMR (CDCl₃) δ 7.3 (dd, J=2.9, 4.9 Hz, 1 H), 7.07 (m, 1 H), 6.98 (dd, J=1.2, 4.9 Hz, 1 H), 3.51 (t, J=7.1 Hz, 2 H), 2.94 (t, J=7.1 Hz, 2 H).

Reduction of the azide (2.43 g, 15.86 mmol) was accomplished using triphenylphosphine (4.16 g, 15.86 mmol) in THF (50 mL) and water (314 mg, 17.45 mmol) (according to B. Ganem et al., J. Org. Chem. 1987, 52, 5044). After stirring overnight, the THF was evaporated in vacuo, then aqueous hydrochloric acid was added. The aqueous phase was washed thoroughly with EtOAc. Sodium hydroxide was then added until a pH of 9 was reached. Extraction of the solution with DCM, evaporation and drying (sodium sulfate) gave crude 1 which was purified by kugelrohr distillation (bp 75° C., 0.5 mbar): 1.48 g (73%), colorless liquid. ¹H-NMR (CDCl₃) δ 7.27 (dd, J=2.8, 4.9 Hz, 1 H), 6.99 (bd, J=2.0 Hz, 1 H), 6.95 (dd, J=1.0, 4.9 Hz, 1 H), 2.96 (t, J=6.8 Hz, 2 H), 2.78 (t, J=6.8 Hz, 2 H), 1.24 (bs, 2 H).

Example 2

Synthesis of 2-cyclopropyl-2-phenylethylamine (2)

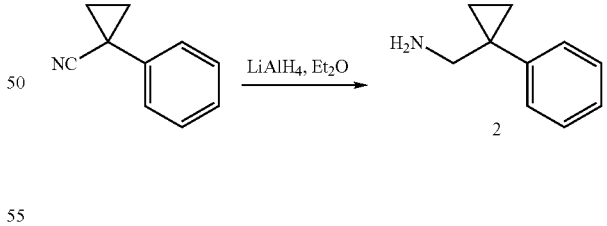

1-Phenyl-1-cyclopropanecarbonitrile (1.0 g, 6.98 mmol) was added to a stirred suspension of lithium aluminum hydride in anhydrous diethyl ether (25 mL). The suspension was refluxed for 2 h, then cooled to 0° C., and the excess hydride was destroyed by careful addition of water. After treatment with sodium hydroxide (1 N), the mixture was filtered and the filtrate extracted with diethyl ether. After drying of the organic phase with and evaporation 2 (719 mg, 70%) was obtained as a clear liquid and used without further purification. ¹H NMR (DMSO-d₆): δ 7.28 (m, 4 H), 7.17 (m, 1 H), 2.70 (s, 2 H), 1.45 (bs, 2 H); 0.78 (dd, J=6.2, 3.8 Hz, 2 H); 0.67 (dd, J=6.2 Hz, 3.8 Hz, 2 H). MS: (m/z) 148 (M+1)+.

Example 3

Synthesis of 3-(2-Aminoethyl)-1-(tert-butyl-acetyl) indole (3)

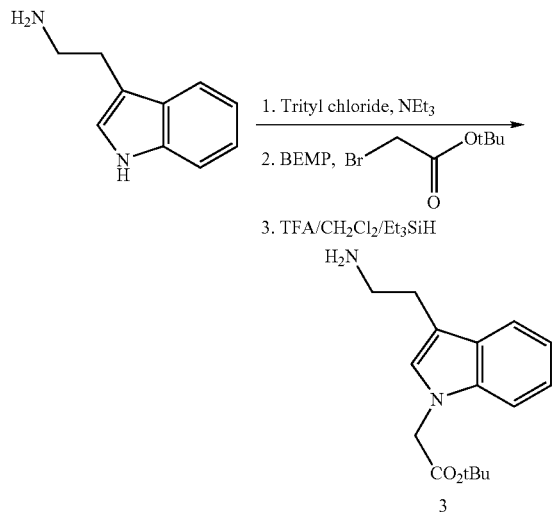

2.0 g of tryptamine (12.5 mmol) were dissolved in DCM (50 mL) and treated in one portion with triethylamine (1.74 mL. 12.5 mmol, 1 eq) and trityl chloride (3.44 g, 12.3 mmol). The resulting solution was stirred for 24 h at room temperature while protected from light. Volatiles were evaporated and the residue treated with aqueous HCl (1 N). The solid formed was filtered and washed with small portions of ether then dissolved in aqueous sodium hydrogencarbonate and extracted into DCM. The organic layer was dried and evaporated to give 4.48 g (89%) of 3-(N-trityl-(2-aminoethyl))-indole, which was used without further purification.

To a solution of the foregoing compound (0.5 g, 1.24 mmol) in anhydrous THF (12 mL), BEMP (0.46 mL, 1.61 mmol) and t-butyl-bromoacetate (0.24 mL, 1.61 mmol, 1.2 eq) were added dropwise via syringe. The solution was stirred at room temperature for 48 h and then diluted with diethyl ether, washed with water (2×) and brine. The organic layer was dried and evaporated and the residue purified by flash chromatography (eluent: PE/EtOAc 7:1, 50 g silica gel) affording 537 mg (85%) of the acylated indole.

The foregoing compound (530 mg, 1.02 mmol) was deprotected with TFA/DCM/TES (5:90:5, 11 mL). After 10 min the mixture was poured into hydrochloric acid (1 N), the aqueous layer was washed with DCM and diethyl ether and then brought to pH 9 by addition of sodium carbonate. Extraction with DCM, drying of the organic layer and evaporation gave 172 mg (63%) of 3 as a pale-yellow oil, which was used without further purification. $^1$H NMR (300 MHz, DMSO-$d_6$): δ 7.53 (d, J=7.8 Hz, 1 H); 7.27 (d, J=8.2 Hz, 1 H); 7.11 (s, 1 H); 7.11 (t, J=7.1 Hz, 1 H); 7.01 (t, J=7.4 Hz, 1 H); 4.91 (s, 2 H); 2.78 (m, 4 H); 1.98 (bs, 2 H), 1.41 (s, 9 H). MS (m/z) 275 (M+1)+.

Example 4

Synthesis of tert-Butyl-4-(2-aminoethyl)-benzoate hydrochloride (5a) and the methyl ester 5b

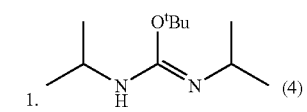

α-Bromo-4-toluic acid (10 g, 46.5 mmol) was suspended in DCM and isourea 4 (18.6 g, 93 mmol) in DCM (50 mL) was added dropwise. The resulting mixture was refluxed for 6 h, then another portion of 4 (18.6 g, 46.5 mmol) was added. After refluxing the mixture overnight, it was filtered through a plug of silica gel, eluting with PE/EtOAc (9:1). A colorless oil was obtained (13.4 g) after evaporation of the solvents, which contained tert-butyl-4-bromomethyl benzoate and 14% of diisopropylurea. This material was dissolved in DMF (50 µL) and added dropwise during 15 min to a solution of sodium cyanide (2.84 g, 58 mmol) in water (5 mL) at 0° C. The yellow solution was stirred for 1 h at this temperature, then water (200 mL) was added and the aqueous phase was extracted with diethyl ether. The organic phase was washed with water and brine, dried (sodium sulfate) and evaporated. The crude product was purified by flash chromatography (PE/EtOAc, 92.5:7.5) to give tert-butyl-4-cyanomethyl benzoate (8.2 g, 76%) as a colorless oil. $^1$H NMR (CDCl$_3$) δ 8.01 (d, J=8.3 Hz, 2 H), 7.40 (d, J=8.3 Hz, 2 H), 3.82 (s, 2 H), 1.61 (s, 9 H).

The foregoing compound (5.0 g, 23.6 mmol) was hydrogenated in a mixture of methanol/acetic acid (4:1, v/v, 150 mL) using palladium on charcoal (1.5 g, 10% Pd) under balloon pressure of hydrogen overnight. After removal of the catalyst by filtration, toluene (250 mL) was added to the filtrate and the solution was evaporated in vacuo. This process was repeated two times. The oily residue was then dissolved in toluene (150 mL) and a solution of hydrochloric acid in diethyl ether (1 M, 60 mL) was added. After evaporation, an off-white solid was obtained, which was crystallized from chloroforme and n-heptane. Compound 5 was obtained as a white solid (3.42 g, 56%). Another 2.25 g (37%) were obtained from by evaporating the mother liquor and crystallizing the residue as described above. $^1$H NMR (DMSO-$d_6$) δ 8.52 (bs, 3 H), 7.93 (d, J=6.6 Hz, 2 H), 7.29 (d, J=6.6 Hz, 2 H), 3.23–3.41 (bs, 4 H), 1.58 (s, 9 H).

Using identical procedures for the cyanide displacement and the hydrogenation, but methyl-α-bromotoluic ester as the starting material (obtained from the acid by esterification with trimethylsilyl diazomethane in methanol), methyl-4-(2-aminoethyl)-benzoate hydrochloride (5b) was obtained. $^1$H NMR (DMSO-$d_6$) δ 8.18 (bs, 3 H), 7.89 (d, J=6.7 Hz, 2 H), 7.40 (d, J=6.7 Hz, 2 H), 3.80 (s, 3 H), 2.89–3.10 (m, 4 H).

Example 5

Synthesis of Ethyl-3-(2-aminoethyl)-cinnamate hydrochloride (6)

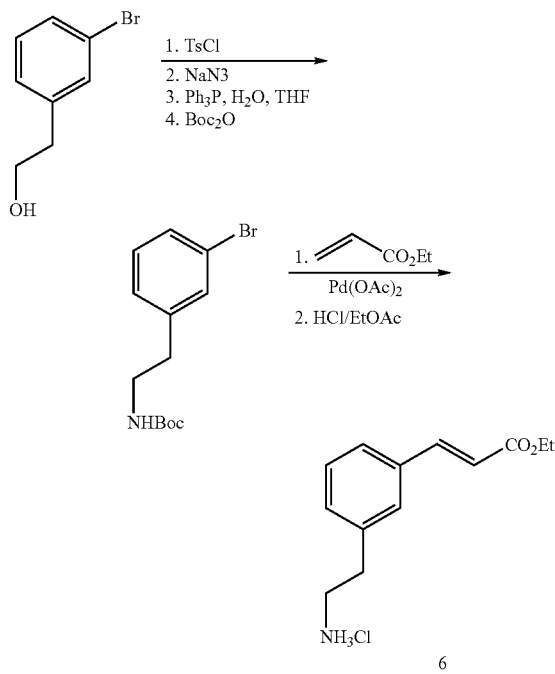

2-(3-Bromophenyl)ethyl alcohol (2.01 g, 10 mmol) was dissolved in DCM (50 mL) and cooled to 0° C. After addition of triethylamine (1.52 g, 15 mmol) and tosyl chloride (1.91 g, 10 mmol) the reaction was stirred at room temperature overnight. TLC indicated complete conversion of the starting material. DCM was evaporated, the mixture was diluted with EtOAc and washed subsequently with aqueous hydrochloric acid (1 N), water, saturated sodium hydrogen carbonate and brine. Drying and evaporation afforded an oil, which was dissolved in anhydrous DMF (10 mL). Sodium azide (1.3 g, 20 mmol) was added and the mixture heated to 40° C. for 16 h. After cooling to room temperature, EtOAc was added and the solution was washed with water (4×) and brine. The resulting oil was filtered over (100 g) with the aid of PE/EtOAc (10:1) to obtain 2-(3-bromophenyl)ethyl azide (1.63 g, 72%) as a colorless oil. $^1$H-NMR (CDCl$_3$) δ 7.39 (m, 2 H), 7.16–7.22 (m, 2 H), 4.51 (bs, 1 H), 3.50 (d, J=6.6 Hz, 2 H), 2.83 (t, J=6.6 Hz, 2 H).

The foregoing compound (1.60 g, 7.08 mmol) was dissolved in THF (70 mL). After triphenylphosphine (1.86 g, 7.08 mmol) and water (140 mg, 7.79 mmol) was added, the mixture was stirred overnight at ambient temperature. The solvent was evaporated, then aqueous hydrochloric acid was added. The aqueous phase was washed thoroughly with EtOAc and DCM. Sodium hydroxide was then added until a pH of 9 was reached. 2-(3-bromophenyl)-ethyl amine (922 mg, 65%) was obtained by extraction of the solution with DCM, evaporation and drying.

The foregoing amine (750 mg, 3.75 mmol) was converted to its Boc-derivative using Boc$_2$O (818 mg, 3.75 mmol) and triethylamine (569 mg, 5.63 mmol) in DCM (20 mL). After workup, the Boc-protected amine (742 mg, 66%) was isolated by flash chromatography (PE/EtOAc 12:1) as a colorless oil. $^1$H-NMR (CDCl$_3$) δ 7.39 (m, 2 H), 7.20 (m, 2 H), 4.51 (bs, 1 H), 3.28 (bd, J=6.3 Hz, 2 H), 2.79 (t, J=6.8 Hz, 2 H), 1.46 (s, 9 H).

The foregoing compound (380 mg, 1.26 mmol) was dissolved in anhydrous DMF (10 mL). Palladium acetate (28 mg, 0.126 mmol), tris-(2-tolyl)phosphine (153 mg, 0.50 mmol), sodium acetate (310 mg, 3.78 mmol) and ethyl acrylate (164 mg, 1.64 mmol) were added. The solution was heated to 120° C. under an atmosphere of argon. After 16 h, the reaction was cooled to room temperature, EtOAc was added and the resulting solution was washed with water (3×) and brine. Drying and evaporation gave an orange oil, which was purified by flash chromatography (PE/EtOAc 10:1) to give Boc-protected 6 as a colorless oil (308 mg, 77%). $^1$H-NMR (CDCl$_3$) δ 7.67 (d, J=16.0 Hz, 1 H), 7.40 (d, J=7.7 Hz, 1 H), 7.35 (s, 1 H), 7.33 (t, J=7.5 Hz, 1 H), 7.22 (d, J=7.4, 1 H), 6.43 (d, J=16.0 Hz, 1 H) 4.55 (bs, 1 H), 4.27 (q, J=7.1, 2 H), 3.39 (bs, 2 H), 2.81 (t, J=6.9 Hz, 2 H), 1.43 (s, 9 H), 1.34 (t, J=7.1, 3 H).

120 mg (0.375 mmol) of this material were dissolved in EtOAc (2 mL) and treated with a solution of hydrochloric acid in EtOAc (3 M, 2 mL). After 6 h the solvents were evaporated to give 6 as an off white solid (89 mg, 93%) after washing with n-pentane. $^1$H-NMR (DMSO-$d_6$) δ 8.19 (bs, 3 H), 7.62 (d, J=16.0 Hz, 1 H), 7.60 (m, 2 H), 7.37 (t, J=7.5 Hz, 1 H), 7.31 (d, J=7.1, 1 H), 6.64 (d, J=16.0 Hz, 1 H), 4.18 (q, J=7.0, 2 H), 3.08 (bs, 2 H), 2.81 (bs, 2 H), 1.25 (t, J=7.0, 3 H).

Example 6

Methyl-(3-chloro-4-(2-aminoethyl))benzoate hydrochloride (7a)

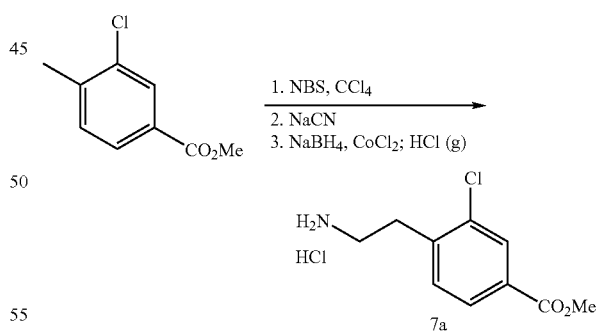

A mixture of of methyl-(3-chloro-4-methyl)-benzoate (4.90 g, 26.54 mmol), NBS (4.72 g, 26.54 mmol) and dibenzoyl peroxide (291 mg, 1.06 mmol) in tetrachloromethane was refluxed for 2 h. The white precipitate that had formed, was removed by filtration, the filtrate diluted with DCM (150 mL) and washed with cold water (3×) and brine. Drying and evaporation afforded a yellow oil (6.24 g). $^1$H NMR (DMSO-$d_6$, 400 MHz) δ 7.96 (d, J=1.7 Hz, 1 H), 7.92 (dd, J=8.0 Hz, 1.7 Hz, 1 H), 7.77 (d, J=8.0 Hz, 1 H), 4.79 (s, 2 H), 3.87 (s, 3 H).

This material was added neat to a solution of tetra-n-butylammonium cyanide (6.31 g, 23.5 mmol) in anhydrous acetonitrile (24 mL) at 0° C. After 10 min the solution was diluted with DCM, and passed through a plug of neutral alumina. The eluate was evaporated and partitioned between diethyl ether and water. The aqueous phase was extracted with diethyl ether and the combined organic phases washed with water and brine. Drying and evaporation gave a brown oil, which was purified by flash chromatography on silica gel (100 g, PE/EtOAc 87:13). A yellow oil was obtained which was further purified by flash chromatography on silica gel (200 g, PE/DCM 1:1) to give methyl-(3-chloro-4-(2-cyanpethyl))benzoate as a white solid (750 mg, 15%).

To a cold (0° C.) solution of the foregoing compound (590 mg, 2.81 mmol) and $CoCl_2$ hexahydrate (1.33 g, 5.6 mmol) in MeOH (20 mL) was added $NaBH_4$ (1.06 g, 28 mmol portionwise during 10 min). The mixture was poured into hydrochloric acid (1 N, 60 mL) and stirred until the black precipitate had dissolved. The aqueous layer was made alkaline with conc ammonia, extracted with $CHCl_3$, dried, filtered and concentrated to give 7a as a brown oil, which was treated with hydrogen chloride in EtOAc (3.2 M, 2 mL). After evaporation and trituration with diethyl ether, 7a was obtained as a yellow powder (420 mg, 60%). $^1$H NMR (DMSO-$d_6$) δ 8.09 (bs, 3 H), 7.95 (d, J=1.7 Hz, 1 H), 7.89 (dd, J=1.7, 7.9 Hz, 1 H), 7.56 (d, J=7.9 Hz, 1 H), 3.87 (s, 3 H), 3.099 (bs, 4 H).

Example 7 tert-Butyl-(3-chloro-4-(2-aminoethyl))benzoate hydrochloride (7b)

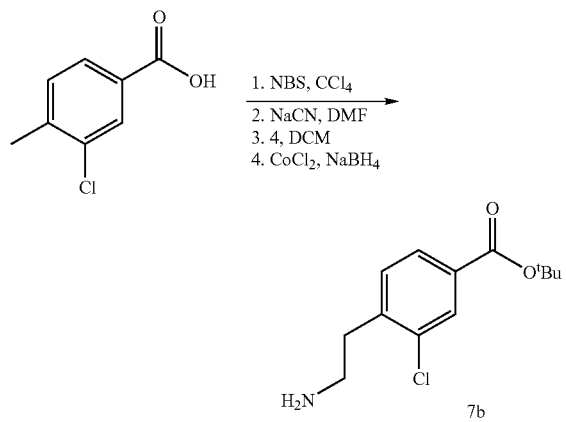

The procedures used for the synthesis of compound 7b are similar to the ones described in example 6. Bromination of 3-chloro-4-methyl-benzoic acid (0.5 g, 2.93 mmol) with NBS in $CCl_4$ (15 mL) gave 4-(bromomethyl)-3-chlorobenzoic acid as a white powder (0.68 g, 93% yield). $^1$H NMR (CDCl$_3$, 400 MHz) δ 7.92 (s, 1 H), 7.87 (dd, J=7.9 Hz, 1.4 Hz, 1 H), 7.70 (d, J=7.9 Hz, 1 H), 4.76 (s, 2 H).

The foregoing compound was dissolved in DMF (3 mL) and cooled to 0° C. NaCN (2 equ) dissolved in 1 mL of water and 2 mL of DMF were added to the solution and the reaction mixture was stirred for 0.5 h. After diluting the mixture with ethyl acetate it was washed with aqueous ammonium sulfate and brine, dried ($Na_2SO_4$), filtered and evaporated to give a yellow solid which was directly used in the esterification step. 2-(2-Chloro-4-carboxyphenyl)-acetonitrile (0.391 g, 2 mmol) was treated with 2 equiv of isourea 4 in 35 mL of DCM at reflux over night. After evaporation of DCM, the crude was diluted in EtOAc (50 mL) and filtered. The filtrate was concentrated and purified by flash chromatography in silica gel eluting with 1% EtOAc in petroleum ether to give tert-Butyl-4-(cyanomethyl)-3-chlorobenzoate (0.24 g, 47% yield). $^1$H NMR (CDCl$_3$, 400 MHz) δ 8.03 (d, J=1.6 Hz, 1 H), 7.93 (dd, J=8.02 Hz, J=1.62 Hz, 1 H), 7.60 (d, J=8.02 Hz, 1 H), 3.89 (s, 2 H), 1.61 (s, 9 H).

The foregoing compound (0.240 g, 0.95 mmol) in MeOH (10 mL), was reduced with $CoCl_2$ hexahydrate (2 equiv) as described in example 6 to give free amine 7b as a brown oil (0.140 g, 58%) after extraction. $^1$H NMR (CDCl$_3$, 400 MHz) δ 7.98 (s, 1 H), 7.80 (d J=7.9 Hz, 1 H), 7.25 (d, J=7.9 Hz, 1 H), 3.10–2.80 (m, 4 H), 1.53 (s, 9 H).

Example 8

Synthesis of tert.-Butyl-(4-(2-aminoethyl)-3,5-difluoro)-benzoate hydrochloride (8)

Step 1:

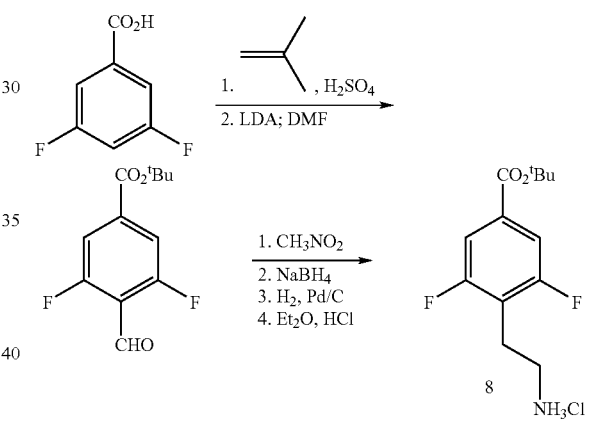

3,5-Difluorobenzoic acid (25 g, 0.158 mol) was dissolved in DCM (150 mL) and dioxane (50 mL). The mixture was transferred into a stainless steel autoclave. Concentrated sulfuric acid (3.6 mL) was added, followed by isobutene (100 mL). The mixture was kept in the autoclave for 5 days. Excess isobutene and the solvents were removed under reduced pressure, the mixture diluted with EtOAc and washed with water, saturated aqueous sodium hydrogen carbonate and brine. Drying and evaporation gave a dark-yellow oil, which was purified by kugelrohr distillation (80–100° C., 1.0 mbar) to give tert-butyl-3,5-difluorobenzoate (27.51, g, 81%) as a colorless solid.

The foregoing compound (10.34 g, 48.3 mmol) was dissolved in anhydrous THF (50 mL) and added to a solution of LDA (53.2 mmol) in THF (100 mL) at −78° C. and left for 1 h at this temperature. Anhydrous DMF (4.1 mL, 53.2 mmol) was added dropwise and 30 min later acetic acid (8 mL), followed by water. The reaction was brought to room temperature and taken into EtOAc. The aqueous phase was extracted with EtOAc and the combined organic fractions washed with brine and dried. Kugelrohr distillation (0.2 mbar, 100° C.) after evaporation of the solvents gave 9.0 g (77%) of tert.-butyl-3,5-difluoro-4-formyl benzoate as a yellow solid. $^1$H NMR (CDCl$_3$) δ 10.38 (s, 1 H), 7.57 (d, J=9.0 Hz, 2 H), 1.60 (s, 9 H).

The foregoing compound (16.9 g, 69.8 mmol) was added to a solution of potassium fluoride (0.93 g) and NMM (113 mL) in isopropanol (75 mL). The mixture was cooled to 0° C. and nitromethane (12.5 mL) was added. After 2 h at 0° C. the mixture was stirred at room temperature overnight. Acetic anhydride (94 mL) and sodium acetate (1.9 g) were added and the mixture brought to 60° C. After 1 h the reaction was cooled to room temperature, diluted with EtOAc and washed successively with hydrochloric acid (1 N, 2×) water, aqueous sodium hydrogencarbonate (2×) and brine. Drying and evaporation gave the nitrostyrene as a brown solid (20.5 g). $^1$H NMR (CDCl$_3$) δ 8.14 (d, J=14.0 Hz, 1 H), 7.89 (d, J=14.0 Hz, 1 H), 7.61 (d, J=9.1 Hz, 2 H), 1.60 (s, 9 H).

The nitrostyrene was dissolved in isopropanol (215 mL) and chloroform (1 l). Silica gel (172 g) was added followed by sodium borohydride (11.0 g, 292 mmol) in 10 portions. After 30 min TLC indicated complete consumption of the starting material. After acidification with hydrochloric acid (100 mL, 1 N) the silica gel was removed by filtration and washed thoroughly with chloroform. The combined filtrates were washed with water and brine, dried and evaporated.

Crystallization of the crude product from hot ethanol gave 8.9 g (43%) of tert-butyl-3,5-difluoro-4-(2-nitroethyl) benzoate as a brown solid. The mother liquor was evaporated and the remaining solid purified by flash chromatography (PE/EtOAc 18:1) to yield another 460 mg (2%). $^1$H NMR (CDCl$_3$) δ 7.52 (app d, J=7.9 Hz, 2 H), 4.62 (t, J=7.3 Hz, 2 H), 3.49 (t, J=7.3 Hz, 2 H), 1.60 (s, 9 H).

The foregoing compound (5.32 g, 18.5 mmol) was dissolved in methanol (93 mL) and hydrogenated over palladium on charcoal (1.0 g, 10% Pd) under atmospheric pressure overnight. Filtration and evaporation in the presence of diethyl ether containing hydrogen chloride (28 mL, 1 N) gave 8 as a yellow solid (5.3 g, 98%). $^1$H NMR (DMSO-d$_6$) δ 8.19 (bs, 3 H), 7.51 (d, J=7.7 Hz, 2 H), 3.26 (m, 4 H), 1.57 (s, 9 H). MS (m/z) 258 ((M+H)$^+$, free amine).

Example 9

Synthesis of 9

3,5-difluorobenzoate in example 8. The crude residue was purified by flash chromatography (PE/EtOAc 8:1) and afforded 1.53 g of pure aldheyde (60%). $^1$H NMR (400 MHz, CDCl$_3$): δ 10.34 (s, 1 H); 7.30 (d, J=7.3 Hz, 2 H). MS (m/z), 168 (M+1)$^+$.

As described in example 8, the foregoing aldehyde was converted to the nitrostyrene, which was reduced with sodium borohydride to give 655 mg of pure 3,5 difluoro-4-(2-nitroethyl)benzonitrile. $^1$H NMR (400 MHz, CDCl$_3$): δ 7.22 (d, J=6.1 Hz, 2 H); 4.61 (t, J=7.1 Hz, 2 H); 3.42 (t, J=7.1 Hz, 2 H). MS (m/z) 213 (M+1)$^+$.

The foregoing compound (262 mg, 1.23 mmol) was dissolved in anhydrous DMF (5 mL), treated with ammonium chloride (132 mg, 2.47 mmol, 2 eq) and sodium azide (160 mg, 2.47 mmol, 2 eq) and heated overnight at 120° C. After evaporation of DMF the residue was taken up into EtOAc, washed with water, 0.1 N hydrochloric acid and brine. The organic layer was dried and evaporated to afford 132 mg (42%) of nitro tetrazole. $^1$H NMR (400 MHz, DMSO-d$_6$): δ 7.73 (d, J=7.8 Hz, 2 H); 4.84 (t, J=6.8 Hz, 2 H); 3.36 (t, J=6.7 Hz, 2 H).

Reduction of the nitro group with 10% Pd/C (26 mg) in methanol (5 mL) at atmospheric pressure of hydrogen for 48 h gave the desired amine 9 (78 mg, 67%) as a colorless solid after removal of the catalyst by filtration and evaporation of the solvent. $^1$H NMR (400 MHz, CDCl$_3$) δ 7.57 (d, J=8.6 Hz, 2 H); 4.61 (t, J=6.8 Hz, 2 H); 3.45 (t, J=6.7 Hz, 2 H); 1.89 (bs, 2 H).

Example 10

Synthesis of 12

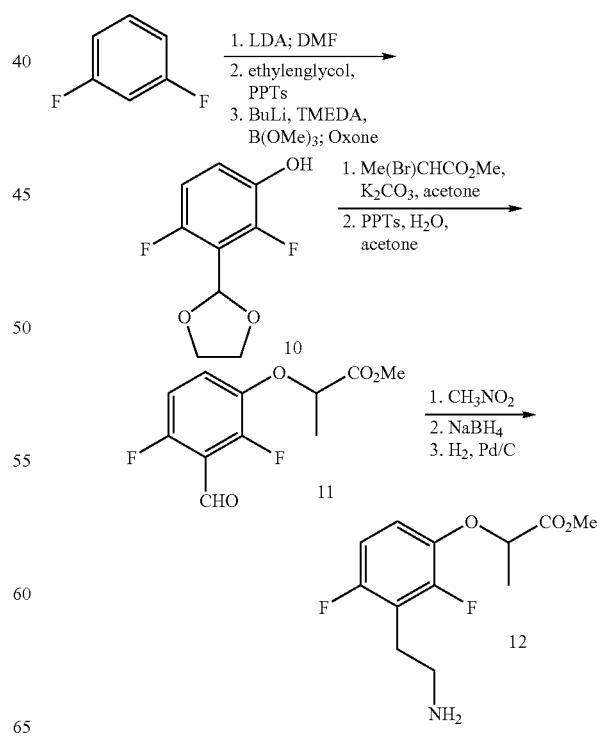

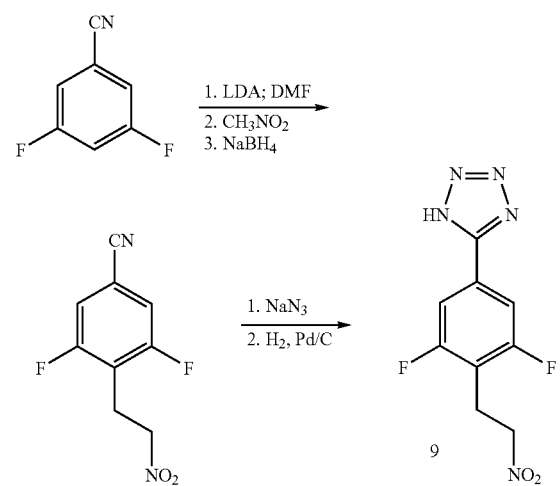

The formylation of 3,5-difluorobenzonitrile (2 g, 14.4 mmol) in dry THF (8 mL) was carried out as described for

Synthesis of 10

The formylation of 1,3-difluorobenzene was carried out as described in example 8. 1,3-difluorobenzene (10 g, 87.65 mmol) in anhydrous THF (174 mL) was added over 5 min to a stirred solution of LDA (48.20 ml, 2M solution in hexane, 96.41 mmol) in THF (20 ml) at −78° C. After 1 h at −78° C., anhydrous DMF (7.46 ml, 96.41 mmol) was added dropwise over 5 minutes. The reaction was further stirred at −78° C. for 20 min, then quenched with glacial AcOH (15 ml) and water (200 ml) and quickly extracted with diethyl ether (3×60 ml). The combined organic layers were washed with water and brine, dried and evaporated to afford 12.3 g of 2,5-difluoro-benzaldehyde. $^1$H-NMR (CDCl$_3$): δ, 7.02 (m 2 H), 7.58 (tt, J=6.2, 8.5 Hz, 1 H), 10.38 (s 1 H).

The aldehyde was dissolved in benzene (173 ml), 1,2-ethanediol (259.86 mmol, 16.13 g) and PPTs (17.3 mmol, 4.35 g) were added and the mixture was refluxed for 4 h. Water was removed with a Dean-Stark trap. After evaporation of the solvent the residue was taken into diethylether and washed with sodium hydrogen carbonate and brine, Drying and evaporation dried over afforded 15 g of crude product. A portion of this material (5 g) were purified by kugelrohr distillation (0.6 mbar, 150–160° C.) giving 4.7 g of pure ketal. $^1$H-NMR (CDCl$_3$): δ 4.05 (m 2 H), 4.21 (m 2 H), 6.25 (s 1 H), 6.89 (m 2 H), 7.29 (tt, J=6.25, 8.4 Hz, 1 H).

TMEDA (25.68 mmol, 3.9 ml, 1.2 eq) was added to a solution of BuLi (2.2 M in hexane, 11.67 ml, 1.2 eq) in THF (70 mL) at −78° C. Then a solution of the foregoing ketal (21.4 mmol, 3.98 g) in THF (40 mL) was added dropwise over 10 min. The solution was stirred for 1 h at −78° C., then trimethylborate (64.2 mmol, 6.67 g) was added in one portion. After warming to 0° C., the reaction was acidified to pH 6.5 with HCl (1M), the THF was evaporated and the residue extracted with DCM after addition of a solution of saturated ammoniumchloride. The combined organic layers were washed with brine, dried and evaporated to give a pink solid (4.5 g), which converted immediately to the phenol (according to K. S. Webb and D. Levy, Tetrahedron Letters, 1995, 36, 5117).

A mixture of the foregoing compound (19.58 mmol, 4.5 g), NaOH (21.54 mmol, 0.86 g), water (60 ml) and acetone (20 ml) was stirred for 5 min until complete dissolution, then sodium bicarbonate (108.86 mmol, 9.14 g) was added. The mixture was cooled to 0° C., a solution of oxone (11.75 mmol, 7.2 g) in an aqueous solution of EDTA (44 ml, 0.004 M) was added dropwise, maintaining the internal temperature below 8° C. during the addition. After 30 min, the reaction was quenched with sodium bisulfite (1 g in 10 ml of water), diluted with EtOAc and acidified with concentrated hydrochloric acid. The aqueous phase was extracted with EtOAc, the combined organic layers were washed with distilled water, dried and evaporated to give 3.8 g of crude phenol 10. Flash chromatography (PE/EA 4:1) gave pure 10 (2.5 g, 63% ) as a colorless solid. $^1$H-NMR (CDCl$_3$): δ 4.05 (m 2 H), 4.21 (m 2 H), 5.09 (s, 1 H), 6.22 (s 1 H), 6.78 (dt, J=1.95, 9.5, 1 H), 6.96 (dt, J=5.19, 9.3 1 H).

Synthesis of 11

Phenol 10 (300 mg, 1.48 mmol) was dissolved in acetone (7.5 mL) containing potassium carbonate (409 mg, 2.96 mmol). Methyl-2-bromopropionate was added and the mixture was refluxed for 3 h. After cooling the reaction to room temperature, EtOAc was added, the organic phase was washed with water and brine, dried (sodium sulfate) and evaporated. The crude product was taken into acetone (15 mL), water (4 mL) and PPTs (107 mg, 0.43 mmol) were added and the resulting mixture was refluxed overnight. After cooling to room temperature, EtOAc was added, the organic phase was washed with aqueous sodium hydrogencarbonate and brine, dried (sodium sulfate) and evaporated. The aldehyde 11 (304 mg) was 906 pure as judged by $^1$H-NMR and taken directly to the Henry aldol reaction. $^1$H-NMR (CDCl$_3$, 400 MHz), d 10.34 (s, 1 H), 7.22 (dt, J=9.0, 5.2 Hz, 1 H), 6.89 (dt, J=1.75, 9.3 Hz, 1 H), 4.74 (q, J=6.8 Hz, 1 H), 3.77 (s, 3 H), 1.66 (d, J=6.8 Hz, 3 H).

Synthesis of 12

Aldehyde 11 (300 mg, 1.23 mmol) was reacted with nitromethane and the resulting nitrostyrene was reduced to the nitroethyl compound as described in example 8. After flash chromatography (PE/EtOAc 5:1) 196 mg (55% ) of the nitroethyl compound were obtained. This material (190 mg, 0.66 mmol) was dissolved in methanol (7 mL) and hydrogenated under atmospheric pressure of hydrogen using palladium on charcoal (40 mg, 10% Pd). After filtration and evaporation amine 12 (155 mg) was obtained, which was used without further purification. $^1$H-NMR (CDCl$_3$, 400 MHz), d 6.68–6.87 (m, 2 H), 4.69 (q, J=6.9 Hz, 1 H), 3.76 (s, 3 H), 2.95 (t, J=7.1 Hz, 2 H), 2.83 (t, J=7.1 Hz, 2 H), 1.68 (d, J=6.8 Hz, 3 H). MS (m/z) 260 (M+H)$^+$.

P$_1$ Building Blocks (L)-2-Amino-4,4-difluorobutanoic acid (13) was synthesized according to Burger et al. (Synthesis, 1996, 1419). It was converted to N-carbamate protected derivatives 14 using standard methodology, as exemplified in example 11.

Other amino acids used like 2-aminobutanoic acid or 2-amino-4,4,4-trifluorobutanoic acid are commercially available.

Example 11

Synthesis of 14

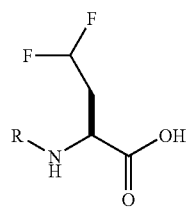

13  R = H
14a R = Cbz
14b R = Boc
14c R = Fmoc 1.0 g (7.19 mmol) of 13 was converted to its Cbz derivative using N-(benzyloxycarbonyloxy)-succinimide (CbzOsu, 1.79 g, 7.19 mmol) in a mixture of water (30 mL) and dioxane (30 mL) containing sodium carbonate (1.52 g, 14.38 mmol). After stirring overnight, dioxane was evaporated and an extractive workup (see also example 15) yielded 2.0 g (quantitative) of 14a as a colorless oil, which was used without further purification. $^1$H-NMR (DMSO-d$_6$) δ 2.08–2.40 (m, 2 H), 4.13 (m, 1 H), 5.04 (s, 2 H), 6.08 (app.

tt, J=56.2, 4.7 Hz, 1 H), 7.20–7.48 (m, 5 H), 7.78 (d, J=7.7 Hz, 1 H), 12.9 (bs, 1 H). MS (m/z) 274 (M+H)+.

From similar experiments, but using Boc-anhydride or FmocOSu instead of CbzOSu gave 14b (88%) or 14c (quantitative). 14b: $^1$H-NMR (DMSO-$d_6$) δ 1.37 (s, 9 H), 2.08–2.29 (m, 2 H), 4.03 (app. dt, J=5.0, 8.8 Hz, 1 H), 6.07 (app. tt, J=56.4, 4.6 Hz, 1 H), 6.92 (bs, 1 H), 7.25 (d, J=8.3 Hz, 2 H), 12.8 (bs, 1 H). MS (m/z) 240.5 (M+H)+. 14c: $^1$H-NMR (DMSO-$d_6$) δ 2.10–2.40 (m, 2 H), 4.13 (m, 1 H), 4.21 (t, J=6.6 Hz, 1 H), 4.32 (d, J=6.9 Hz, 2 H), 6.07 (app. tt, J=56.2, 4.7 Hz, 1 H), 7.32 (t, J=7.3, 2 H), 7.41 (t, J=7.3, 2 H), 7.70 (d, J=7.3 Hz, 2 H), 7.79 (d, J=8.3 Hz, 1 H), 7.88 (d, J=7.3 Hz, 2 H), 12.9 (bs, 1 H). MS (m/z) 362 (M+H)+.

P$_2$ Building Blocks

Example 12

Synthesis of (2S,4S)-Fmoc-4-cyclohexyl-pyrrolidine-2-carboxylic acid (15a) and the Boc-derivative 15b

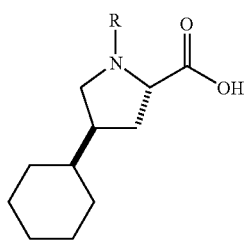

15a R = Fmoc
15b R = Boc

Commercial (2S,4S)-Boc-4-phenyl-pyrrolidine-2-carboxylic acid (1.0 g, 3.43 mmol) was deprotected using TFA (10 mL) in DCM (10 mL). The resulting oil obtained after evaporation of the solvents and coevaporation with hydrogen chloride in diethyl ether was dissolved in ethanol (20 mL). Platinum oxide (100 mg) was added and the resulting mixture was stirred under an atmosphere of hydrogen overnight. After 3 h another 100 mg of platinum oxide was added. Filtration and evaporation gave a colorless solid (782 mg). This compound was converted to the carbamates as described in example 11. 15a (mixture of rotamers): $^1$H NMR (300 MHz, DMSO-$d_6$) δ 12.58 (bs, 1 H) 7.85 (m, 2 H); 7.60 (m, 2 H); 7.20–7.41 (m, 4 H), 4.28 (m, 1 H); 4.25 (m, 1 H); 4.14 (m, 2 H); 3.52 (m, 2 H); 2.92 (m, 1 H); 1.90 (m, 3 H); 1.59 (m, 4 H); 1.13 (m, 4 H); 0.88 (m, 2 H). MS (m/z) 420 (M+1)+. 15b (mixture of rotamers): $^1$H NMR (300 MHz, DMSO-$d_6$) δ 12.44 (s, 1 H); 4.09 (t, J=8.6 Hz, 1 H); 3.51 (m, 1 H); 2.85 (m, 1 H); 1.89 (m, 3 H); 1.59 (m, 5 H); 1.37 and 1.32 (s, 9 H); 1.13 (m, 4 H); 0.90 (m, 2 H).

Example 13

Synthesis of 4-(R)-cyclohexylthio-proline methyl ester hydrochloride (18)

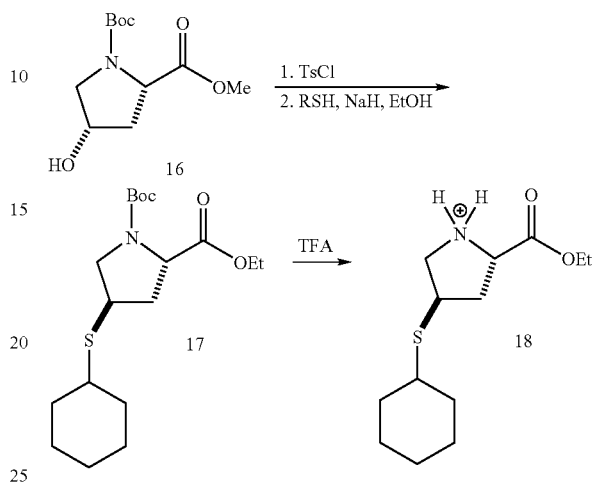

Synthesis of 17

DMAP (100 mg, 0.824 mmol) and p-toluenesulfonyl chloride (1.72 g, 9.07 mmol) were added successively to a solution of 16 (2.02 g, 8.24 mmol) in pyridine (4 ml) at 0° C. under nitrogen and the solution was stirred at room temperature for 48 hrs. The solution was diluted with EtOAc and the organic phase washed with 1N aqueous HCl, aqueous saturated NaHCO$_3$, brine, dried and evaporated to leave a residue which was purified by flash chromatography (PE/EtOAc) yielding 1.35 g (41%) of a colorless oil. $^1$H NMR (rotameric mixture) (DMSO-$d_6$, 400 MHz): δ 0.75–0.85 (1 H, m), 1.29 (5 H, s), 1.33 (4 H, s), 1.98–2.04 (1 H, m), 2.39 (3 H, s), 3.25–3.35 (1 H, m), 3.50–3.55 (1 H, m), 3.55 (1 H, s), 3.57 (2 H, s), 4.25–4.30 (1 H, m), 5.00–5.06 (1 H, m), 7.45 (2 H, d, J=8.0 Hz), 7.72 (2 H, d, J=8.0 Hz). MS (m/z) 400.1 (M+H)+.

To a solution of the foregoing compound (730 mg, 1.83 mmol) in EtOH (2.7 ml) at room temperature under nitrogen were added 2.5 ml of a 2M solution of Na and cyclohexyl mercaptan in EtOH and the solution stirred overnight. The solvent was evaporated in vacuo and the residue was purified by flash chromatography (PE/EtOAc) to obtain 451 mg (70%) of 17 as a colorless oil. $^1$H NMR (rotameric mixture) (DMSO-$d_6$, 400 MHz): δ 1.12–1.36 (17 H, m), 1.48–1.54 (1 H, m), 1.59–1.67 (2 H, m), 1.79–1.88 (2 H, m), 2.07–2.19 (2 H, m), 2.70–2.76 (1 H, m), 3.09–3.14 (1 H, m), 3.37–3.44 (1 H, m), 3.67–3.73 (1 H, m), 4.05–4.15 (2 H, m), 4.15–4.22 (1 H, m); MS (m/z) 358 (M+H)+.

Synthesis of 18

To compound,17 (236 mg, 0.661 mmol) dissolved in EtOAc (3 ml) under nitrogen at room temperature was added HCl/EtOAc (2.5 ml) and the solution stirred for 2 hrs. The solvent was removed in vacuo and the residue washed with Et$_2$O to leave 18 as a colourless oil (100%). $^1$H NMR (DMSO-$d_6$, 400 MHz): δ 1.16–1.29 (8 H, m), 1.48–1.55 (1 H, m), 1.61–1.68 (2 H, m), 1.81–1.86 (2 H, m), 2.07–2.13 (1 H, m), 2.75–2.84 (1 H, m), 2.95 (1 H, dd, J=7.0, 11.6 Hz), 3.34 (m, 1 H), 3.52 (1 H, qn, J=6.9 Hz), 3.64 (1 H, dd, J=7.2, 11.6 Hz), 4.18 (2 H, q, J=7.2 Hz), 4.48 (1 H, t, J=8.0 Hz); MS (m/z): 257.9 (M+H)+.

Example 14

Synthesis of (4R)-(3-phenyl-propyloxy)-proline (20)

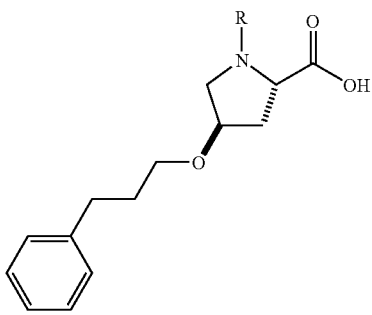

R = Boc 20a
R = Fmoc 20

According to the procedure of Smith et al. (J. Med. Chem. 1988, 31, 875), a mixture of sodium hydride (0.69 g, 60% dispersion in mineral oil, washed with hexane) and N-Boc-L-hydroxyproline (2.0 g, 8.7 mmol) in 20 mL of THF was stirred at room temperature for 45 min. 1.5 equiv of 1-bromo-3-phenylpropane were added and mixture was refluxed for 3 h. Reaction mixture was poured into sodium hydroxide (1 N) and the aqueous layer was washed with hexane, acidified with HCl (1 N) and extracted with DCM. The organic phase was dried over sodium sulfate, filtered and concentrated to afford the title compound 20a as a colorless oil (0.5 g, 17% yield) $^1$H NMR (CDCl$_3$, 400 MHz) δ 7.33–7.17 (m, 5 H), 4.52–4.44 (m, 1 H), 4.08–4.03 (m, 1 H), 3.54–3.39 (m, 4 H), 2.27 (t, J=7.33 Hz, 2 H), 2.44–2.19 (m, 2 H), 1.94–1.85 (m, 2 H), 1.51 (s, 9 H).

The Boc group was removed with hydrogen cloride in dioxane (483 mg of 20a, 7 mL, 4 M, 1 h at room temperature). After evaporation of the solvents, the amine hydrochloride was converted to the Fmoc protected compound 20 using FmocOSu as described in example 11 (504 mg, 78%). $^1$H NMR (DMSO-d$_6$, 300 MHz) δ 7.88 (m, 2 H), 7.65 (m, 2 H), 7.42 (m, 2 H), 7.32 (m, 3 H), 7.25 (m, 2 H), 7.19 (m, 2 H), 4.25–4.35 (m, 2 H), 4.12–4.23 (m, 2 H), 4.06 (m, 1 H), 3.58–3.35 (m, 4 H), 2.61 (t, J=7.4 Hz, 2 H), 2.29 (m, 1 H), 1.97 (m, 1 H), 1.73–1.84 (m, 2 H).

P$_3$ Building Blocks

Example 15

Synthesis of N-(Isobutyloxycarbonyl)-valine (21)

L-Valine (5.86 g, 50 mmol) was dissolved in a mixture of water (200 mL) containing sodium carbonate (10.6 g, 100 mmol). The solution was cooled to 0° C., then a solution of isobutylchloroformate (6.76 g, 49.5 mmol) in dioxane (100 mL) was added dropwise over 50 min. The ice-bath was removed and the reaction stirred overnight. Dioxane was evaporated, the aqueous phase was extracted once with diethylether and the brought to pH 2 by addition of hydrochloric acid. Extraction with DCM (3×, 150 mL each), drying of the organic phase (sodium sulfate) and evaporation gave 21 (14.2 g) as a colorless solid. $^1$H-NMR (DMSO-d$_6$) δ 12.48 (bs, 1 H), 7.24 (d, J=8.2 Hz, 1 H), 3.95 (dd, J=6.2, 8.3 Hz, 1 H), 3.73 (d, J=6.7 Hz, 1 H), 2.01 (m, 1 H), 1.83 (m, 1 H), 0.87 (bs, 12 H).

Example 16

Synthesis of N-(Isobutyloxycarbonyl)-γ-tert-butyl-glutamate (22)

Using the conditions described in example 15, (γ-O-tert.-Butyl)-L-glutamic acid (10 g, 49.2 mmol) was converted to 22 (colorless solid, 14.2 g, 95%). $^1$H-NMR (DMSO-d$_6$) δ 12.57 (bs, 1 H), 7.34 (d, J=8.1 Hz, 1 H), 3.95 (m, 1 H), 3.72 (d, J=6.6 Hz, 1 H), 2.25 (m, 1 H), 1.93 (m, 1 H), 1.85–1.71 (m, 2 H), 1.38 (s, 9 H).

Example 17

Synthesis of Indoline (25)

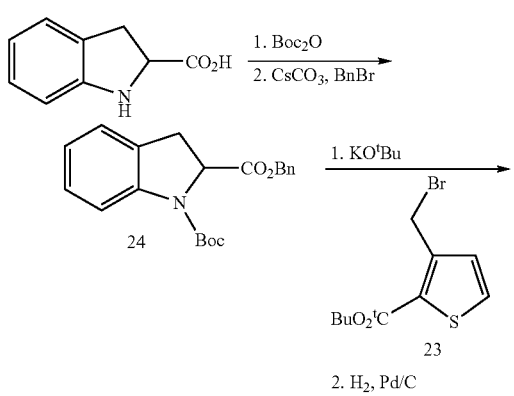

24

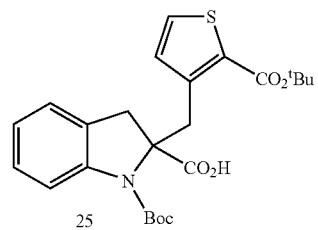

25

Synthesis of 23

O-tert-butyl-N,N'-diisopropylisourea 4 (10.55 g, 52.7 mmol) was added to a solution of 3-Methyl-2-thiophene-carboxylicc acid in DCM (45 ml). The reaction mixture was slowly warmed to reflux and maintained at reflux for 8 hours. Another 10.55 g of 4 was added and reflux was continued for an additional 10 hours. Cooling, filtration and evaporation left a solid residue which was suspended in EtOAc/PE (1:9) and filtered over a short pad of silica-gel. Evaporation of the solvents gave 6.1 g (87%) of the tert-butyl ester.

To a solution of the above compound (5.0 g, 25.4 mmol) in CCl$_4$ (120 ml) was added benzoylperoxide (25 mg) and the reaction mixture stirred at 85° C. for 10 min. NBS (4.97 g, 28 mmol) and more benzoylperoxide (25 mg) were added and mixture stirred at reflux for 2 hours. Cooling, filtration and evaporation left an oil which was purified by flash chromatography on silica gel (PE/EtOAc 60:1) to give 5.8 g (82%) 23 as a colorless oil. $^1$H-NMR (DMSO-d$_6$) δ 7.81 (d, J=5.1 Hz, 1 H), 7.26 (d, J=5.1 Hz, 1 H), 4.93 (s, 2 H), 1.55 (s, 9 H). MS (m/z) 278 (M+H)$^+$.

Synthesis of 24

To a solution of (±) indoline-2-carboxylic acid (2.33 g, 20 mmol) and Et$_3$N (5.6 mL, 40 mmol) in MeOH (40 mL) cooled to 0° C. was added portionwise Boc$_2$O (5.24 g, 24 mmol). The ice bath was removed and the mixture stirred at room temperature for 18 hours. After evaporation of the solvent the resulting oil was dissolved in EtOAc and washed successively with hydrochloric acid (1 N) and brine. Drying and evaporation gave 4.48 g (85%) of a white solid. The N-Boc protected indoline-2-carboxylic acid (4.48 g, 17 mmol) was dissolved in DMF (50 mL) and cesium carbonate (5.54 g, 17 mmol) and benzyl bromide (1.65 mL, 16.2 mmol) were added. The resulting solution was stirred at room temperature for 24 hours. The reaction mixture was diluted with EtOAc and washed with 1 N aqueous HCl, saturated aqueous NaHCO$_3$ and brine. Drying and evaporation gave an oil, which was purified by flash chomatography on silica gel (PE/EtOAc 12:1) to give 5.42 g (95%) of indoline 24.

Synthesis of 25

To a solution of KHMDS (0.5 N in toluene, 8 ml, 4 mmol) in THF (6 ml) cooled to −78° C. was added dropwise a solution of 24 (706 mg, 2 mmol) in THF (4 ml). The resulting solution was stirred at −40° C. for 1 hour and then cooled to −78° C., whereupon 23 (1.66 g, 6 mmol) in THF (4 ml) was added dropwise. The reaction mixture was allowed to warm to room temperature over 5 h, and then diluted with EtOAc (100 ml). The organic layer was washed with hydrochloric acid (1 N), saturated aqueous NaHCO$_3$ and brine. Drying and evaporation gave an oil, which was purified by flash chromatography on silica gel (PE/EtOAc 8:1) to give 935 mg (85%) of the fully protected alkylated indoline. $^1$H-NMR (DMSO-d$_6$) δ 7.51 (bs, 1 H); 7.50 (d, J=5.2 Hz, 1 H), 7.34 (s, 5 H), 7.03 (t, J=8.0 Hz, 1 H), 6.91 (d, J=7.3 Hz, 1 H), 6.78 (t, J=7.4 Hz, 1 H), 6.72 (d, J=5.1 Hz, 1 H), 5.25 (d, J=12.7 Hz, 1 H), 5.20 (d, J=12.7 Hz, 1 H), 4.16 (d, J=14.2 Hz, 1 H), 3.70 (d, J=14.2 Hz, 1 H), 3.29 (s, 2 H), 1.51 (s, 9 H), 1.48 (s, 9 H). MS (m/z) 550.7 (M+H)$^+$.

This compound was dissolved in MeOH (50 ml). Pd/C 30% (160 mg) was added and the reaction mixture was stirred at room temperature under hydrogen (atmospheric pressure) for 18 hours. Dilution with EtOAc, filtration and evaporation of the solvent gave 781 mg (100%) of 25 as an oil. $^1$H-NMR (DMSO-d$_6$) δ 7.52 (bs, 1 H); 7.51 (d, J=5.2 Hz, 1 H), 7.03 (t, J=7.4 Hz, 1 H), 6.91 (d, J=7.3 Hz, 1 H), 6.79 (t, J=7.3 Hz, 1 H), 6.72 (d, J=5.2 Hz, 1 H), 4.20 (d, J=14.2 Hz, 1 H), 3.70 (d, J=14.2 Hz, 1 H), 3.30 (s, 2 H), 1.51 (s, 9 H), 1.49 (s, 9 H).

Example 18

Synthesis of tetrahydroquinoline (27)

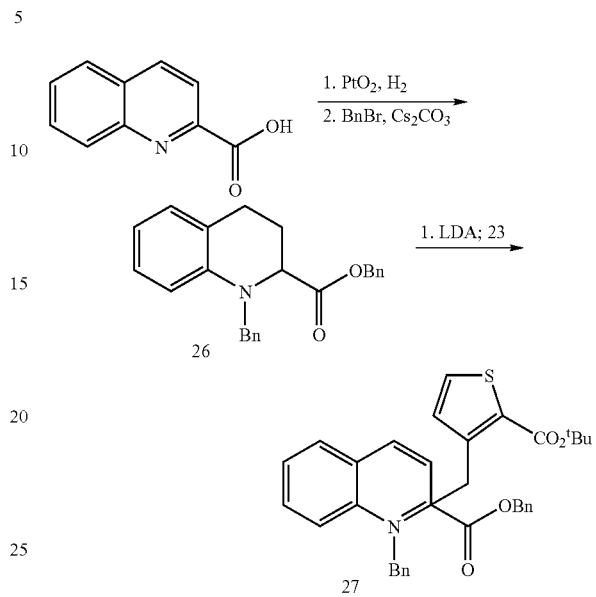

A solution of quinaldic acid (5 g, 28.9 mmol) in MeOH (100 mL) was treated with PtO$_2$ (500 mg) then stirred under a positive pressure of hydrogen for 4 h. The solution was filtered and concentrated to afford an orange oil which was taken up in DMF (30 mL) and treated with cesium carbonate (18.4 g, 56.4 mmol) and benzyl bromide (6.71 mL, 56.4 mmol). After stirring for 15 h the mixture was diluted with hydrochloric acid (1 N) and extracted with EtOAc. Concentration of the dried organic layer gave 26 as a white solid (5.8 g, 57%). $^1$H NMR (DMSO-d$_6$) 7.32 (m, 10 H), 6.89 (m, 2 H), 6.51 (m, 1 H), 6.39 (d, J=8.1 Hz, 1 H), 5.17 (d, J=7.5 Hz, 1 H), 5.13 (d, 1 H, J=7.5 Hz, 1 H), 4.63 (d, J=8.1 Hz, 1 H), 4.40 (m, 1 H), 4.39 (d, J=8.1 Hz, 1 H), 2.68 (m, 1 H), 2.55 (m, 1 H), 2.30 (m, 1 H), 2.13 (m, 1 H); MS (m/z) 268.3 (MH)$^+$ A solution of 26 (1.50 g, 4.20 mmol) in dry THF (20 mL) was treated dropwise at −78° C. with LDA (2 M solution in THF, 1.96 mL, 3.92 mmol) and the solution was maintained at −78° C. for 1.5 h. A solution of 23 (3.49 g, 12.6 mmol) in THF (5 mL) was added over 30 min via syringe pump, and the mixture was warmed to room temperature and stirred for 15 h. After addition of hydrochloric acid (1 N), the mixture was extracted with EtOAc. Concentration of the organic layer gave a residue which was purified by chromatography (Biotage column, silica gel, 40×115, PE/EtOAc 98:2) to give 27 as a solid (994 mg, 43%). $^1$H NMR (DMSO-d$_6$) 7.63 (d, J=5.2 Hz, 1 H), 7.25 (m, 6 H), 7.15 (m, 2 H), 7.10 (m, 2 H), 7.04 (d, J=5.2 Hz, 1 H), 6.84 (m, 2 H), 6.50 (m, 1 H), 6.27 (d, J=7.8 Hz, 1 H), 5.12 (m, 2 H), 4.88 (d, J=11.1 Hz, 1 H), 4.49 (d, J=13.7 Hz, 1 H), 3.98 (d, J=10.5 Hz, 1 H), 3.37 (d, J=10.5 Hz, 1 H), 2.57 (m, 1 H), 2.43 (m, 1 H, 2.15 (m, 2 H), 1.42 (s, 9 H)

Synthesis of Inhibitors

Reactions on solid support were performed either in polyethylene syringes agitating the reaction mixture on a wheel, or with the Quest 210 synthesizer (Argonaut Technologies) using standard solid-phase techniques.

Example 19

Solid Phase Synthesis of 165

Step 1:

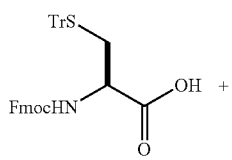

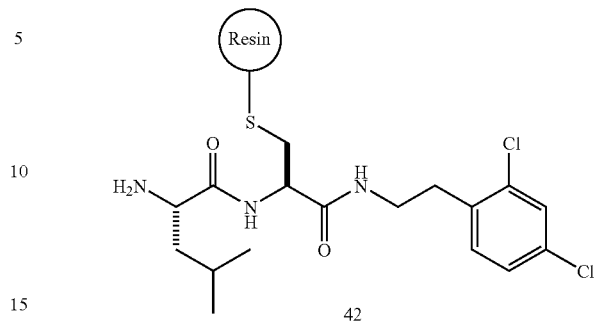

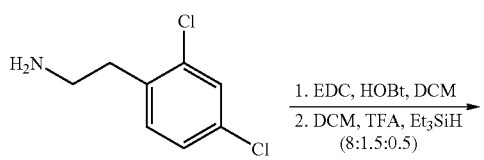

Step 2:

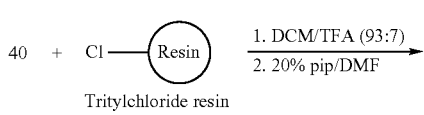

Step 4:

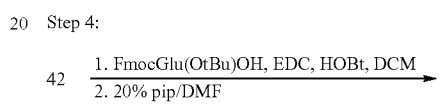

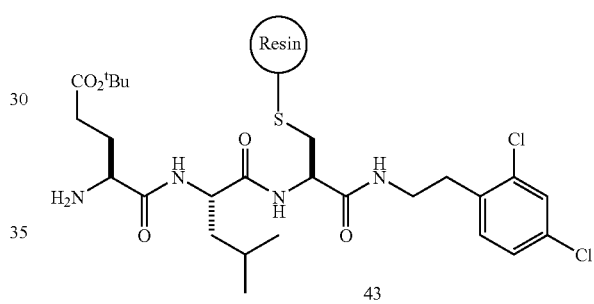

Step 5:

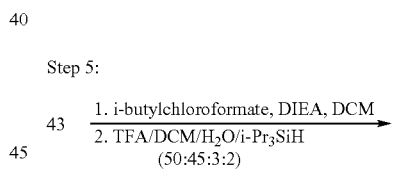

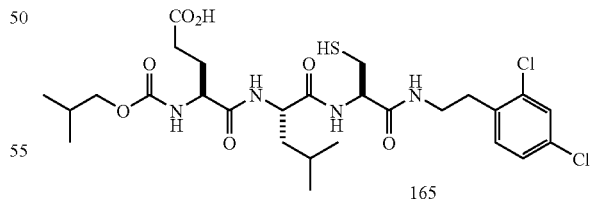

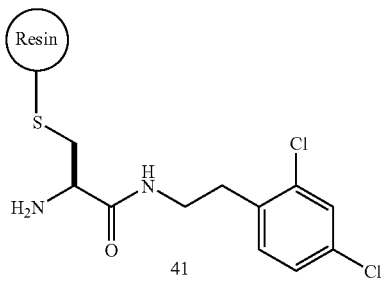

Step 3:

Step 1: N2-[(9-Fluorenyl)methoxycarbonyl]-N1-[2-(2,4-dichloropenyl)ethyl]-L-cysteinamide (40)

A solution of Fmoc-S-trityl-L-cysteine (12.0 g, 20.5 mmol), EDC (4.32 g, 22.55 mmol) and HOBt (3.05 g, 22.55 mmol) was stirred at 0° C. in anhydrous DCM (200 mL) for 15 min. Then 2-(2,4-dichlorophenyl)ethyl amine (4.68 g, 24.6 mmol) was added dropwise. The cooling bath was removed and the mixture stirred overnight. Most of the DCM was removed in vacuo, the residue was dissolved in EtOAc (300 mL) and subsequently washed with aqueous potassium hydrogensulfate (1 M, 2×), water, saturated aqueous sodium hydrogencarbonate and brine. Drying over sodium sulfate and removal of the solvent gave an off-white foam (16.0 g).

14.0 g (18.48 mmol) of this material were stirred in DCM containing 15% (TFA) and 5% TES (total volume 200 mL) at room temperature. After 10 min the. reaction was evaporated to dryness, the solid residue was washed three times with 150 mL n-pentane/diethylether (1:1, v/v) and then dried under high vacuum. 8.86 g of 40 compound was obtained as a colorless solid. $^1$H-NMR (DMSO), δ 8.08 (t, J=5.5 Hz, 1 H), 7.89 (d, J=7.5 Hz, 2 H), 7.73 (d, J=7.4 Hz, 2 H), 7.54 (s, 1 H), 7.41 (t, J=7.4 Hz, 2 H), 7.32 (t, J=7.4 Hz, 2 H), 7.30 (bs, 2 H), 4.32 (m, 1 H), 4.27 (m, 2 H), 4.02 (m, 1 H), 3.31 (m, 2 H), 2.82 (t, J=6.9 Hz, 2 H), 2.75 (m, 1 H), 2.61 (m, 1 H), 2.22 (t, J=8.4 Hz, 1 H).

Step 2: Synthesis of Resin 41

1.5 g Trityl chloride resin (Novabiochem, loading 2.05 mmol of active chlorine) was washed once with DCM and then added to a solution of 40 in DCM containing 7% TFA (40 mL). The solution was agitated overnight (orbital shaker, or slow stirring on a magnetic stirrer). The resin was isolated on a sintered glass funnel, washed with DCM (5×50 mL), then methanol (1×50 mL), again with DCM and dried overnight in vacuo. 2.57 g of this material in a 50 mL syringe with a 20 micron frit were treated with a solution of 20% piperidine in DMF for 1 h. The resin was drained, washed 3× with DMF and the treatment with 20% piperidine/DMF was repeated. After drainage, the resin was washed with DMF (2×20–25 mL), DMF/DCM(1×25 mL)), DCM (3×20–25 mL), methanol and diethylether (1×20–25 mL each) and dried in vacuo.

Step 3: Synthesis of Resin 42

The foregoin resin was acylated with a premixed solution of Fmoc-L-leucine (4.23 g, 12.35 mmol), EDC (2.30 g, 12.35 mmol) and HOBt (1.62 g, 12.35 mmol) in DCM (40 mL) for 3 h. After drainage the resin was washed with DCM (1×25 mL), DMF (2×20–25 mL), DMF/DCM (1×25 mL), DCM (3×20–25 mL), methanol and diethylether (1×25 mL each). After drying in vacuo it was treated with a solution of 20% piperidine/DMF (25 mL, 40 min). The resin was drained, washed with DMF (2×20–25 mL), DMF/DCM (1×25 mL), DCM (3×20–25 mL), methanol and diethylether (1×20–25 mL each) and then dried in vacuo.

Step 4:. Synthesis of Resin 43

1.6 g of resin 42 were acylated with a premixed solution of Fmoc-(γ-O-tert.-butyl)-L-glutamic acid (3.3 g, 7.7 mmol), EDC (1.48 g, 7.7 mmol) and HOBt (1.04 g, 7.7 mmol) in DCM (30 mL) for 5 h. After washing, drying and deprotection with a solution of 20% piperidine/DMF (20 mL, 1 h) as described above in step 3, the resin was drained, washed with DMF (2×20–25 mL), DMF/DCM (1×25 mL), DCM (3×20–25 mL), methanol and diethylether (1×20–25 mL each), then dried first under a stream of nitrogen, and subsequently in vacuo.

Step 5: Synthesis of 165

To 30 mg of resin 43 (ca. 0.029 mmol of compound) was added DCM (1 mL), followed by diisopropylethylamine (0.2 mL) and isobutyl chloroformate (0.038 mL, 0.29 mmol). The resin was agitated for 5 h. Prior to cleavage, the resin was washed with DMF (3×1 mL) and DCM (3×1 mL) and then treated with a solution of 50% TFA/45% DCM/5% water (1.5 mL) containing TIPS (0.02 mL) for 30 min at room temperature. The resin was washed with cleavage mixture (1–1.5 mL) and DCM (2 mL). The combined filtrates were evaporated, the residue was dissolved in 30% water/70% acetonitrile and lyophilized to obtain crude 165 (21 mg, quantitative) as a white powder. A sample (15 mg) was purified by preparative RP-HPLC (gradient: 60% A, 2 min isocratic, then in10 min to 30% A (RT 11.2 min). Fractions containing the desired product were pooled and lyophilized to give compound 165 (10 mg).

$^1$H-NMR (DMSO-d$_6$) δ 12.0 (bs, 1 H), 7.98 (m, 2 H), 7.93 (d, J=7.7 Hz, 1 H), 7.55 (s, 1 H), 7.32 (s, 2 H), 7.27 (d, J=7.7 Hz, 1 H), 4.26 (m, 2 H), 3.97 (m, 1 H), 3.72 (d, J=6.6 Hz, 2 H), 3.34 (m, 1 H), 3.27 (m, 1 H), 2.81 (t, J=6.9 Hz, 2 H), 2.58–2.72 (m, 2 H), 2.24 (t, J=7.7 Hz, 2 H), 2.19 (t, J=8.5 Hz, 1 H), 1.85 (m, 2 H), 1.72 (m, 1 H), 1.58 (m, 1 H), 1.45 (m, 2 H), 0.86 (m, 9 H), 0.83 (d, J=6.5 Hz, 3 H). MS (m/z) 635.4, 637.4 (M+H)$^+$.

Example 20

Synthesis of Compound 225

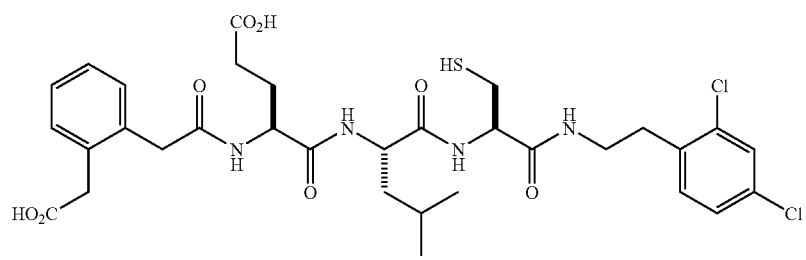

To resin 43 (30 mg, see example 19) was added DCM (1 mL), DIEA (0.2 mL), EDC (29 mg, 0.15 mmol) and 1,2-phenylen diacetic acid (56 mg, 0.29 mmol). After agitation for 5 h, the resin was drained, washed and cleaved as described in example 19, step 5. Evaporation of the solvents gave the crude product, which was purified by preparative RP-HPLC. Gradient: 60% A, 2 min isocratic, then in 10 min to 30% A (RT 8.3 min). Fractions containing the desired product were pooled and lyophilized to give compound 225 (10 mg, 48%). $^1$H-NMR (DMSO-$d_6$) δ 12.2 (bs, 2 H), 8.27 (d, J=7.6 Hz, 1 H), 7.99 (m, 2 H), 7.95 (d, J=8.1 Hz, 1 H), 7.55 (s, 1 H), 7.31 (s, 2 H), 7.22 (m, 1 H), 7.17 (m, 3 H), 4.23 (m, 3 H), 3.68 (d, J=16.1 Hz, 1 H), 3.62 (d, J=16.1 Hz, 1 H), 3.54 (d, J=15.4 Hz, 1 H), 3.50 (d, J=15.4 Hz, 1 H), 3.20–3.40 (m, 2 H), 2.81 (t, J=6.9 Hz, 2 H), 2.68 (m, 1 H), 2.60 (dd, J=7.6, 14.5 Hz, 1 H), 2.24 (m, 3 H), 1.89 (m, 1 H), 1.72 (m, 1 H), 1.56 (m, 1 H), 1.45 (m, 2 H), 0.86 (d, J=6.5 Hz, 3 H), 0.82 (d, J=6.5 Hz, 3 H). MS (m/z) 711.3, 713.5 (M+H)$^+$.

Example 21

Synthesis of Compound 101

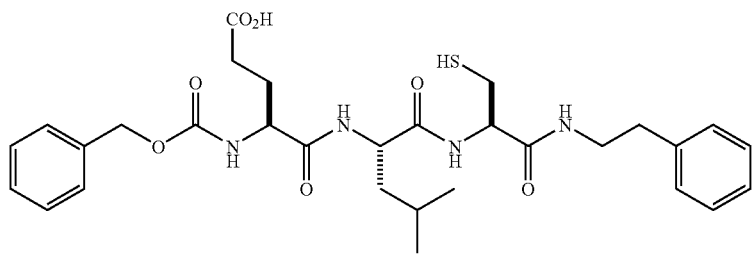

Step 1: N2-[(9-Fluorenyl)methoxycarbonyl]-N1 [2-phenyl-ethyl]-L-cysteinamide

The title compound was obtained analogous to procedure described in to example 19, step 1 from coupling of Fmoc-S-trityl-L-cysteine and phenethylamine and subsequent deprotection with TFA and TES.

Step 2

Analogous to the procedure described in example 19, step 2, trityl chloride resin (525 mg, Novabiochem, loading 0.4 mmol of active chlorine) was alkylated with the foregoing compound (380 mg, 0.85 mmol) in DCM containing 5% TFA (4 mL). The resin was then deprotected with 20% piperidine/DMF.

Step 3

Analogous to the procedure described in example 19, step 3, the foregoing resin (450 mg) was acylated with Fmoc-L-leucine (239 mg 0.68 mmol) and then treated with 20% piperidine/DMF to cleave the Fmoc protecting group.

Step 4

Analogous to the procedure described in example 19, step 4, the foregoing resin (270 mg) was acylated with Fmoc-(γ-O-tert.-butyl)-L-glutamic acid (77 mg, 0.18 mmol) and then treated with 20% piperidine/DMF to cleave the Fmoc protecting group.

Step 5

As described in example 19, step 5, the foregoing resin was acylated with N-(benzyloxycarbonyloxy)succinimide (90 mg, 0.36 mmol) in DCM (1 mL) and DIEA (0.5 mL). After agitating the mixture overnight the resin was drained and washed as described. After cleavage from the resin, 101 was isolated by preparative RP-HPLC (gradient: 65% A, 3 min isocratic, then in 9 min to 35% A; RT 10.2 min). $^1$H-NMR (DMSO-$d_6$) δ 12.0 (bs, 1 H), 7.98 (m, 3 H), 7.45 (d, J=8.1 Hz, 1 H), 7.22–7.38 (m, 7 H), 7.18 (m, 3 H), 5.01 (s, 2 H), 4.27 (m, 2 H), 4.01 (m, 1 H), 3.20–3.40 (m, 2 H), 2.68 (t, J=7.2 Hz, 2 H), 2.60–2.68 (m, 2 H), 2.25 (t, J=7.6, 2 H), 2.16 (t, J=8.4, 1 H), 1.86 (m, 1 H), 1.73 (m, 1 H), 1.59 (m, 1 H), 1.46 (m, 2 H), 0.87 (d, J=6.4 Hz, 3 H), 0.83 (d, J=6.3 Hz, 3 H). MS (m/z) 601.4 (M+H)$^+$.

Example 22

Synthesis of Compound 102

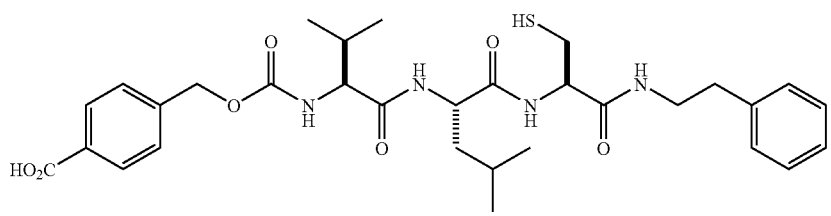

The resin (160 mg) obtained in example 21 (steps 1 to 3, ca. 0.021 mmol of compound) was acylated with FmocValOH (36 mg, 0.105 mmol) analogous to the procedure described in example 19, step 4, and then treated with 20% piperidine/DMF to cleave the Fmoc protecting group. The resulting resin was then suspended in DCM (1 mL) and DIEA (0.5 mL). Solid N-(4-carboxymethyl-benzyloxycarbonyloxy)-succinimide (65 mg, 0.21 mmol, prepared from methyl-(4-hydroxymethyl)-benzoate and N,N'-disuccinimidyl carbonate according to A. K. Gosh et al, Tetrahedron Letters 1992, 33, 2781–2784) was added. After agitating the mixture overnight the resin was drained and washed with DMF (3×1 mL) and DCM (3×1 mL) and then treated with a solution of 50% TFA/45% DCM/5% water (2.5 mL) containing TIPS (0.02 mL) for 30 min at room temperature. The resin was washed with cleavage reagent (1–1.5 mL) and DCM (2 mL) and the combined filtrates were evaporated. The crude methyl ester was hydrolyzed with aqueous sodium hydroxide (1 mL, 1 N) in methanol (2 mL) for 20 min at 50° C. After cooling to room temperature, hydrochloric acid (1 mL, 1 N) was added and the mixture diluted with acetonitrile/water (40/60, v/v). Compound 102 was obtained by preparative RP-HPLC (gradient: 65% A, 3 min isocratic, then in 9 min to 35% A; RT 8.2 min; 7 mg, 54% 6). $^1$H-NMR (DMSO-$d_6$) δ 12.7 (bs, 1 H), 7.99 (app. d, J=7.3, 2 H), 7.92 (m, 3 H), 7.45 (d, J=7.9 Hz, 2 H), 7.39 (d, J=8.8 Hz, 1 H), 7.26 (m, 1 H), 7.25 (d, J=6.9 Hz, 1 H), 7.18 (d, J=7.2 Hz, 2 H), 7.17 (m, 1 H), 5.10 (s, 2 H), 4.28 (m, 2 H), 3.85 (app. t, J=7.6 Hz, 1 H), 3.20–3.30 (m, 2 H), 2.69 (t, J=7.3 Hz, 2 H), 2.60–2.68 (m, 2 H), 2.15 (t, J=8.2, 1 H), 1.95 (m, 1 H), 1.60 (m, 1 H), 1.45 (m, 2 H), 0.84 (m, 12 H). MS (m/z) 615.5 (M+H)$^+$.

Example 23

Synthesis of Compound 247

Step 1: N2-[(9-Fluorenyl)methoxycarbonyl]-N1-[2-(2-chloropenyl)ethyl]-L-cysteinamide The title compound was obtained analogous to the procedure described in to example 19, step 1 from coupling of Fmoc-S-trityl-L-cysteine (14.0 g, 23.9 mmol) and 2-(2-chlorophenyl)ethyl amine (31.07 mmol) and subsequent deprotection with TFA and TES.

Step 2

Analogous to the procedure described in example 19, step 2, trityl chloride resin (1.8 g, Novabiochem, loading 2.05 mmol/g of active chlorine) was alkylated with the foregoing compound (10.8 g, 22.6 mmol) in DCM containing 5% TFA (45 mL). The Fmoc group was cleaved with 20% pip/DMF.

Step 3

Analogous to the procedure described in example 19, step 3, the foregoing resin was acylated with a premixed solution of Fmoc-L-leucine (3.70 g, 10.4 mmol), PyBop (5.4 g, 10.4 mmol), DIPEA (20.8 mmol) and HOBt (1.6 g, 10.4 mmol) in DMF (25 mL) overnight. After drainage and washing the resin was then treated with 20% piperidine/DMF to cleave the Fmoc protecting group.

Step 4

Analogous to the procedure described in example 1, step 4, the foregoing resin was acylated with a premixed solution of Fmoc-(γ-O-tert.-butyl)-L-glutamic acid (4.4 g, 10.4 mmol), PyBop (5.4 g, 10.4 mmol), DIPEA (20.8 mmol) and HOBT (1.6 g, 10.4 mmol) in DMF (25 mL) and then treated with 20% piperidine/DMF to cleave the Fmoc protecting group.

Step 5

The foregoing resin (20 mg, 0.022 mmol) in DCM (2 mL) was reacted with phenylisocyanate (26 mg, 0.22 mmol) and DIPEA (0.046 mL, 0.22 mmol) for 2 h. Then the resin was drained and washed with DMF (2×10 mL), DCM (2×10 mL) and diethyl ether (2×10 mL). Cleavage of the product was affected with a mixture of TFA/DCM/water/and TIPS (6:6:1:1; 2 mL) for 10 min. This procedure was repeated two times. The combined filtrates were aged for 40 min, then evaporated. The residue was dissolved in a mixture of water

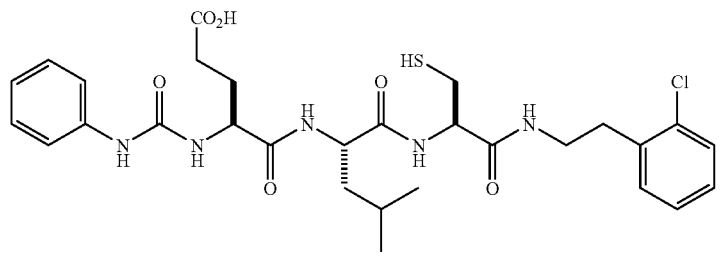

and acetonitrile (30/70, 3 mL) and lyophilized to give 247 as a colorless powder. $^1$H-NMR(DMSO-$d_6$) δ 8.65 (s, 1H), 8.22 (4, J=7.72, 1H), 8.017 (m,2H), 7.43–7.19 (m, 8H), 6.89 (t, 7.31 Hz, 1H), 6.41 (d,J=7.84 Hz, 1H), 4.33–4.26 (m, 3H), 3.31 (m,2H), 2.85 (t,J=7.10 Hz,2 H), 2.71 (m,2H), 2.28–2.16 (m,3H),1.89–1.45 (m,5 H), 0.89 (d, J=6.61 Hz, 3H), 0.85 (d, J=6.61 Hz, 3H); MS (m/z) 619 (M+H)$^+$.

Example 24

Synthesis of Compound 252

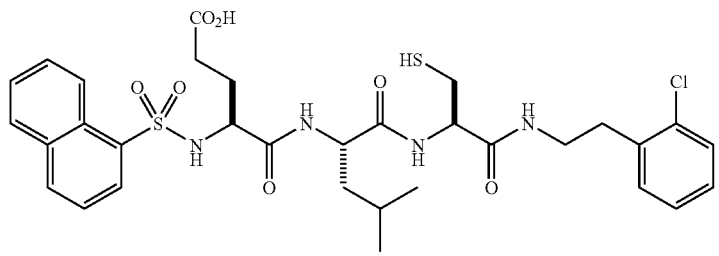

The resin (20 mg) obtained in example 23, step 4 was acylated with 1-naphthalensulfonyl chloride (50 mg, 0.22 mmol) under identical conditions described in example 23, step 5. After cleavage and lyophilization 252 was obtained as a colorless powder. $^1$H-NMR(DMSO-$d_6$) δ 8.65 (d, J=7.96 Hz, 1H), 8.31 (d, J=9.04 Hz, 1 H),8.20 (d, J=8.28, 1 H), 8.12–7.92 (m, 5 H), 7.68–7.56 (m, 3 H), 7.40 (m, 1 H), 7.31–7.22 (m, 3 H), 4.22 (q, J=7.33 Hz, 1 H), 4.04 (m, 1 H), 3.81 (q, J=5.65, 1 H),3.36–3.22 (m, 2 H),2.81 (t, J=5.98 Hz, 2 H)2.67–2.58 (m,2 H), 2.14–1.95 (m,3 H),1.76–1.60 (m,2 H),1.28–1.57 (m, 3 H),0.75 (d, J=5.83 Hz, 3 H),0.61 (d,J=5.83 Hz, 3 H); MS (m/z) 691 (M+H)$^+$.

Example 25

Synthesis of Compound 409

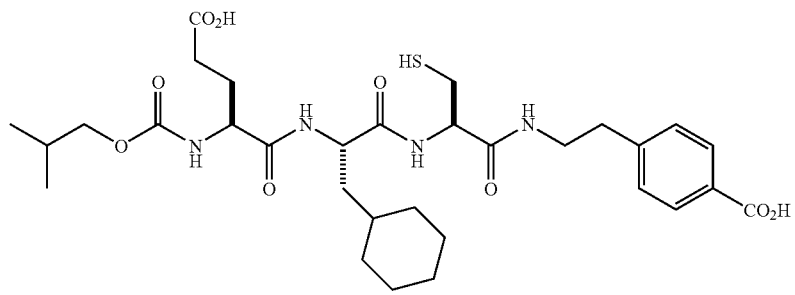

Step 1: N2-[(9-Fluorenyl)methoxycarbonyl]-N1-[2-(4-carboxymethyl-phenyl)ethyl]-L-cysteinamide The title compound was obtained analogous to the procedure described in to example 19, step 1 from coupling of Fmoc-S-trityl-L-cysteine and amine hydrochloride 5b and subsequent deprotection with TFA and TES.

Step 2–5

The procedures are identical to the ones described in example 19, using 20 mg of resin, but in step 3 (2S, 4S)-Fmoc-L-cyclohexyl-alanine was used instead of Fmoc-Leu-OH. The crude product obtained after cleavage (22 mg0.033 mmol) was dissolved in methanol (1 mL) and cooled to 0° C. After 5 minutes 1 ml of 1 N NaOH (30 equiv) was added and reaction mixture was left at room temperature. After 90 min solution was concentrated in vacuo and ethyl acetate was added. The organic layer was washed with 1 N HCl (3×), brine and dried. Evaporation of the solvent and freeze drying from acetonitrile/water gave 409 (8 mg, 35% ). $^1$H-NMR (DMSO-$d_6$, 300 MHz, 300K) δ 8.00–7.92 (m, 3H), 7.85 (d, J=8.19 Hz, 2H), 7.33 (d, J=8.19, 2H), 7.28 (m, 1H), 4.36–4.22 (m, 2H), 3.97 (m, 1H), 3.73 (d, J=6.63 Hz, 2H), 2.79 (t, J=6.92, 2H), 2.68–2.62 (m, 2H), 2,2–2,1 (m, 3H), 1.9–1.0 (m, 18 H), 0.877 (d, J=6.63 Hz, 6H). MS (m/z) 651.5 (M+H)$^+$.

Example 26

Synthesis of Compound 506

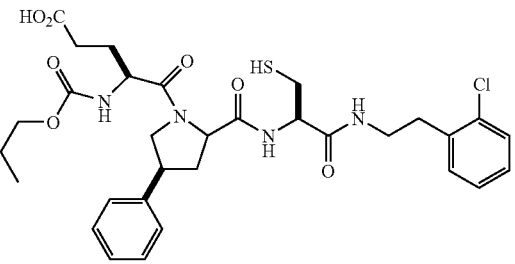

The procedure is identical to the one described in example 23, but in step 3 (2S,4S)-Fmoc-4-phenyl-pyrrolidine-2-carboxylic acid was used instead of Fmoc-Leu-OH and in step 5 isobutyl chloroformate was used for the acylation. $^1$H-NMR(DMSO-$d_6$) δ 8.13 (d, J=8.08 Hz, 1H),7.99 (t, J=3.8 Hz,1H), 7.43–7.20 (m, 10H), 4.54 (t, J=4.96 Hz, 1H),4.33 (q, J=7.89 Hz,2H), 4.15 (m, 1H),3.71 (d, J=6.52 Hz, 2H),3.55(m,2H), 3.39–3.28 (m,2H),2.86 (t, J=7.11 Hz, 2H), 2.78–2.65 (m, 2H), 2.48–2.23 (m, 5H),1.94–1.24 (m,3H), 0.86 (d, J=6.6 Hz, 6H); MS (m/z) 661 (M+H)$^+$.

Example 27

Synthesis of Compound 177 and 178

Step 1: Synthesis of Resin 44

A solution of Fmoc-S-trityl-L-cysteine (10.0 g, 17.1 mmol), in DCM containing 15% trifluoroacetic acid (TFA) and 5% TES (total volume 150 mL) was stirred at room temperature. After 10 min the reaction was evaporated to dryness, the solid residue was washed three times with 150 mL n-pentane and then dried under high vacuum. 4.46 g of Fmoc-L-cysteine was obtained as a colorless solid. This material was dissolved in DCM (20 mL) containing 7% TFA. 1.0 g Trityl chloride resin (Novabiochem, loading 2.05 mmol of active chlorine) was added in one portion. The solution was slowly agitated overnight (orbital shaker, or slow stirring on a magnetic stirrer). The resin was isolated on a sintered glass funnel, washed with DCM (5×40 mL), methanol (1×40 mL) and again with DCM and dried overnight in vacuo.

Step 1:

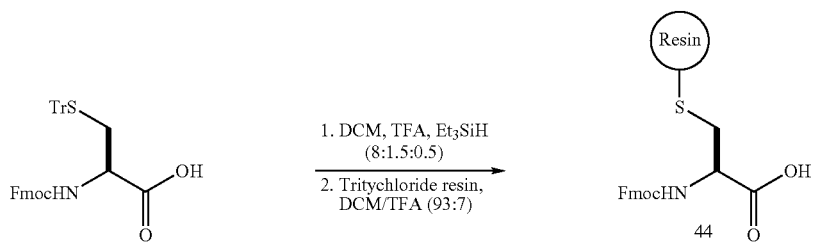

Step 2:

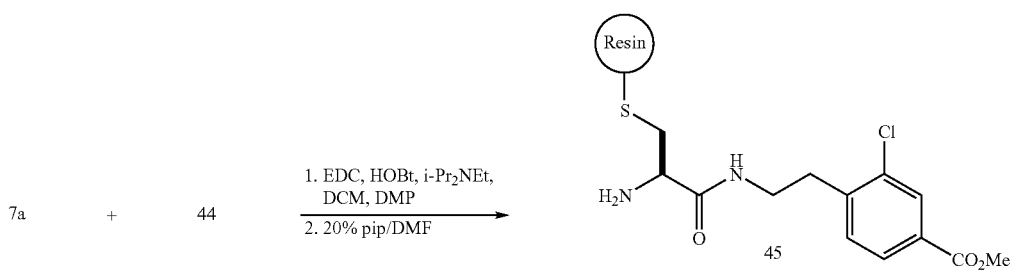

Step 3

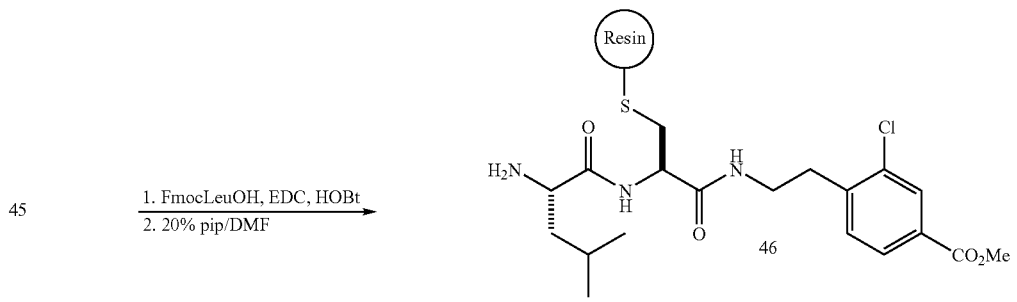

Step 4:

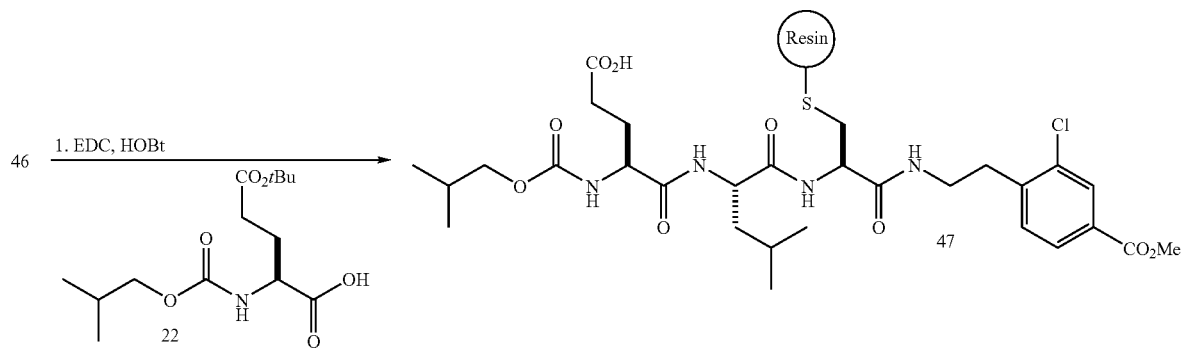

Step 5:

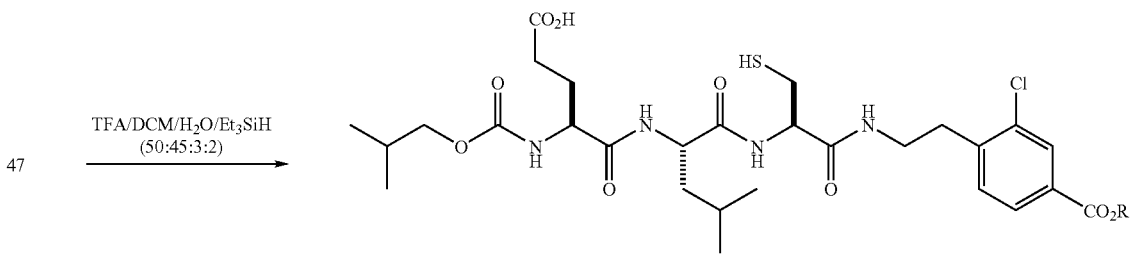

TFA/DCM/H₂O/Et₃SiH
(50:45:3:2)

47 →

Step 6:

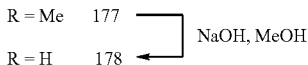

R = Me  177
R = H   178     NaOH, MeOH

Step 2: Synthesis of 45

To 40 mg (loading ca. 1.25 mmol/g, 0.05 mmol) of resin 44 was added a solution of 7a (53 mg, 0.26 mmol), EDC (50 mg, 0.26 mmol) and HOBt (40 mg, 02.6 mmol) in DCM (1.5 mL), followed by DIEA (0.2 mL). The reaction was agitated overnight, the resin was washed with DMF (2×3 mL), DCM/DMF (1×3 mL), DCM (1×), methanol (1×) and DCM (3×3 mL). Deprotection of the Fmoc-group was achieved by treatment with 20% piperidine/DMF (3 mL) for 1 h, then washing the resin with DMF (2×3 mL) and again treatment with 20% piperidine/DMF. After drainage, the resin was washed with DMF (2×3 mL), DCM/DMF (1×3 mL), DCM (1×), methanol (1×) and DCM (3×3 mL) and dried under a stream of nitrogen.

Step 3: Synthesis of Resin 46

To resin 45 was added a solution of Fmoc-L-leucine (92 mg, 0.26 mmol), EDC (50 mg, 0.26 mmol) and-HOBt (40 mg, 0.26 mmol) in DCM(1.5 mL). After 4 h the resin was washed as described in step 2, then treated with 3 mL of 20% piperidine/DMF for 1 h. The resin was washed as described in step 2, and dried under a stream of nitrogen.

Step 4: Synthesis of Resin 47

Compound 22 (79 mg, 0.26 mmol), EDC (50 mg) and HOBt (40 mg) in DCM (1.5 mL) was added to resin 46 and agitated for 4 h. The resin was washed and dried as described in step 3.

Step 5: Synthesis of 177

Resin 47 was treated with a solution of 50% TFA/45% DCM/5% water (2.5 mL) containing TES (0.02 mL) for 30 min at room temperature. After drainage, the resin was washed with cleavage reagent (2 mL) and DCM (3 mL) and the combined filtrates were evaporated. The residue was dissolved in 30% water/70% acetonitrile and lyophilized to obtain methyl ester 177 (30 mg, ca.91% crude) as a white powder. A sample (7 mg) of the compound was purified by preparative RP-HPLC (gradient: 65% A, 3 min isocratic, then in 9 min to 35% A; RT 10.7 min; 4 mg). $^1$H-NMR (DMSO-d$_6$) δ 8.0 (m, 2 H), 7.92 (d, J=7.7 Hz, 1 H), 7.89 (d, J=1.6 Hz, 1 H), 7.81 (dd, J=1.6, 7.95 Hz, 1 H), 7.45 (d, J=7.9 Hz, 1 H), 7.25 (d, J=7.6 Hz, 1 H), 4.25 (m, 2 H), 3.95 (app. dd, J=8.2, 13.7 Hz, 1 H), 3.84 (s, 3 H), 3.71 (d, J=6.6 Hz, 2 H), 3.37 (m, 2 H), 2.90 (t, J=6.8 Hz, 2 H), 2.69 (m, 1 H), 2.62 (m, 1 H), 2.23 (t, J=7.6 Hz, 2 H), 2.19 (t, J=8.6 Hz, 1 H), 1.82 (m, 2 H), 1.71 (m, 1 H), 1.58 (m, 1 H), 1.44 (m, 2 H), 0.86 (m, 9 H), 0.82 (d, J=6.5 Hz, 3 H). MS (m/z) 659.5, 661.0 (M+H)$^+$.

Step 6: Synthesis of 178

The remaining methyl easter 177 (23 mg) was dissolved in methanol and THF (1 mL each) and 1 N sodium hydroxide (1 mL) was added dropwise. After 15 min 1 N HCl (1 mL) was added and the solution diluted with water/acetonitrile (50/50, v/v). Compound 178 was isolated by preparative RP-HPLC (gradient: 65% A, 3 min isocratic, then in 9 min to 35% A; RT 7.2 min; 13 mg). $^1$H-NMR (DMSO-d$_6$) δ 8.0 (m, 2 H), 7.93 (d, J=7.7 Hz, 1 H), 7.87 (d, J=1.5 Hz, 1 H), 7.79 (dd, J=1.5, 7.9 Hz, 1 H), 7.42 (d, J=7.9 Hz, 1 H), 7.25 (d, J=7.8 Hz, 1 H), 4.25 (m, 2 H), 3.96 (app. dd, J=8.1, 13.7 Hz, 1 H), 3.71 (d, J=6.6 Hz, 2 H), 3.37 (m, 2 H), 2.90 (t, J=6.9 Hz, 2 H), 2.70 (m, 1 H), 2.62 (m, 1 H), 2.23 (t, J=7.7 Hz, 2 H), 2.19 (t, J=8.3 Hz, 1 H), 1.83 (m, 2 H), 1.72 (m, 1 H), 1.58 (m, 1 H), 1.44 (m, 2 H), 0.86 (m, 9 H), 0.82 (d, J=6.5 Hz, 3 H). MS (m/z) 645.5, 647.5 (M+H)$^+$.

Example 28

Synthesis of Compound 181

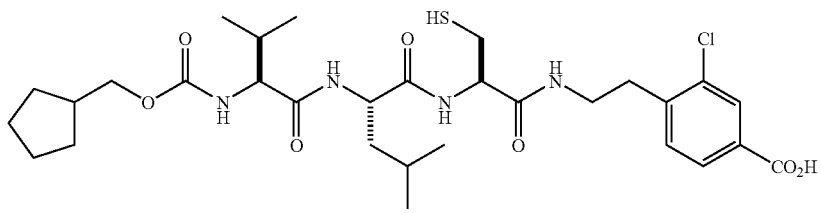

Resin 46 (200 mg) (obtained as in example 27, steps 1 to 3) was acylated with a premixed solution of Fmoc-L-Valine (441 mg, 1.3 mmol), EDC (249 mg, 1.3 mmol) and HOBt (199 mg, 1.3 mmol) for 5 h. After washing and drying of the resin as described in example 27, step 2, the Fmoc group was deprotected with 20% piperidine/DMF (6 mL) for 1 h. After drainage and washing (step 2, example 27) the resin was dried under a stream of nitrogen.

The acylating reagent cyclopentylmethyloxycarbonyl-N-hydroxysuccinimide was prepared in situ by addition of 2qcyclopentanol (50 mg, 0.5 mmol) and triethylamine (152 mg, 1.5 mmol) to a solution of N,N'-disuccinimidyl carbonate (128 mg, 0.5 mmol) in anhydrous acetonitrile (2 mL) (see A. K. Gosh et al, Tetrahedron Letters 1992, 33, 2781–2784). After 30 min stirring at room temperature the solution was diluted with DCM (2 mL) and added to 40 mg (0.05 mmol) of the foregoing resin. After agitation for 5 h, the resin was drained and washed as described above. It was then treated with a solution of 50% TFA/45% DCM/5% water (2.5 mL) containing TES (0.02 mL) for 30 min at room temperature. After drainage, the resin was washed with cleavage reagent (2 mL) and DCM (3 mL). The combined filtrates were evaporated, the residue was dissolved in 30% water/70% acetonitrile and lyophilized to obtain the methyl ester of 181 as a white powder. This powder was dissolved in methanol (1 mL) and 1 N sodium hydroxide (1 mL) was added dropwise. After 30 min 1 N HCl (1 mL) was added and the solution diluted with water/acetonitrile (60/40, v/v). Compound 181 was purified by preparative RP-HPLC (gradient: 65% A, 5 min isocratic, then in 7 min to 30% A; RT 12.8 min; 8 mg, 25% ). $^1$H-NMR (DMSO-$d_6$) δ 8.06 (bs, 1 H), 7.96 (m, 2 H), 7.88 (d, J=1.5 Hz, 1 H), 7.79 (dd, J=1.5, 7.9 Hz, 1 H), 7.44 (d, J=7.9 Hz, 1 H), 7.10 (d, J=8.6 Hz, 1 H), 4.26 (m, 2 H), 3.83 (d, J=7.0 Hz, 2 H), 3.82 (m, 1 H), 3.35 (m, 2 H), 2.91 (t, J=6.7 Hz, 2 H), 2.55–2.70 (m, 2 H), 2.21 (t, J=8.6 Hz, 1 H), 2.11 (m, 1 H), 1.94 (m, 1 H), 1.33–1.78 (m, 9 H), 1.21 (m, 2 H), 0.88 (d, J=6.5 Hz, 3 H), 0.83 (m, 9 H). MS (m/z) 661.7, 643.7 (M+H)$^+$.

Example 29

Synthesis of Compounds 135 and 134

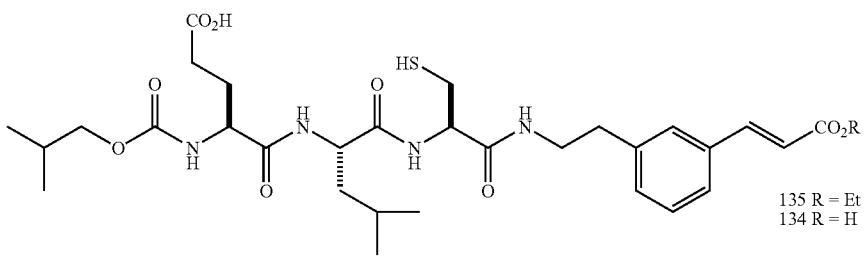

135 R = Et
134 R = H

The synthesis of compound 135 proceeds analogous to the procedures described in example 27, steps 2 to 5, using 60 mg of resin 44 and 6 (100 mg, 0.39 mmol). After cleavage from the resin, 135 was isolated by preparative reversed-phase HPLC. Gradient: 65% A, 5 min isocratic, then in 7 min to 35% A. Fractions containing the desired product (RT 12.4 min) were pooled and lyophilized. $^1$H-NMR (DMSO-$d_6$) δ 7.96 (m, 2 H), 7.92 (d, J=7.8 Hz, 1 H), 7.61 (d, J=16.1 Hz, 1 H), 7.55 (s, 1 H), 7.53 (m, 1 H), 7.32 (t J=7.6 Hz, 1 H), 7.25 (m, 2 H), 6.60 (d, J=16.1 Hz, 1 H), 4.25 (m, 2 H), 4.17 (q, J=7.1 Hz, 2 H), 3.96 (m, 1 H), 3.71 (d, J=6.6 Hz, 2 H), 3.23–3.50 (m, 2 H), 2.73 (t, J=7.2 Hz, 2 H), 2.66 (m, 1 H), 2.2.61 (m, 1 H), 2.24 (t, J=7.6 Hz, 2 H), 2.13 (t, J=8.2 Hz, 1 H), 1.83 (m, 2 H), 1.76 (m, 1 H), 1.59 (m, 1 H), 1.45 (m, 2 H), 1.25 (t, J=7.1 Hz, 3 H), 0.86 (m, 9 H), 0.82 (d, J=6.5 Hz, 3 H). MS (m/z) 665.5 (M+H)$^+$.

Synthesis of 134

Crude 135 from a similar experiment was dissolved in methanol (1 mL) and 1 N sodium hydroxide (1 mL) was added dropwise. After 15 min 1 N HCl (1 mL) was added and the solution diluted with water/acetonitrile (50/50, v/v). The compound was purified by preparative RP-HPLC with as described for 134. Fractions containing 134 (RT 9.1 min) were pooled and lyophilized. $^1$H-NMR (DMSO-d$_6$) δ 7.97 (m, 2 H), 7.92 (d, J=7.8 Hz, 1 H), 7.55 (d, J=16.0 Hz, 1 H), 7.51 (s, 1 H), 7.50 (m, 1 H), 7.31 (t J=7.5 Hz, 1 H), 7.25 (m, 2 H), 6.50 (d, J=16.0 Hz, 1 H), 4.27 (m, 2 H), 3.97 (app. dd, J=8.0, 13.5 Hz, 1 H), 3.72 (d, J=6.6 Hz, 2 H), 3.40–3.50 (m, 2 H), 2.73 (t, J=7.1 Hz, 2 H), 2.60–2.68 (m, 2 H), 2.24 (t, J=7.6 Hz, 2 H), 2.13 (t, J=8.2 Hz, 1 H), 1.83 (m, 2 H), 1.76 (m, 1 H), 1.58 (m, 1 H), 1.44 Em, 2 H), 0.86 (m, 9 H), 0.82 (d, J=6.5 Hz, 3 H). MS (m/z) 637.5 (M+H)$^+$.

Example 30

Synthesis of Compound 109

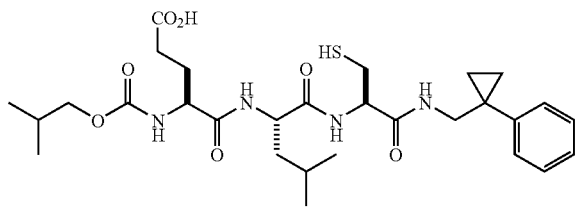

The synthesis of compound 109 proceeds analogous to the procedures described in example 27, steps 2 to 5, using 40 mg of resin 44 and 2 (38 mg, 0.26 mmol). After cleavage from the resin, 109 (15 mg, 50% ) was isolated by preparative reversed-phase HPLC. Gradient: 65% A, 5 min isocratic, then in 7 min to 30% A; RT 11.8 min. $^1$H NMR: (300 MHz, DMSO-d$_6$): δ 7.98 (d, J=8.1 Hz, 1 H); 7.89 (m, 2 H); 7.24 (m, 5 H); 7.1 (m, 1 H); 4.29 (m, 2 H); 3.96 (m, 1 H); 3.73 (d, J=6.6 Hz, 2 H); 3.47 (dd, J, =13.8 Hz, J$_2$=6.2 Hz, 1 H); 3.23 (dd, J$_1$=13.7 Hz, J$_2$=5.3 Hz, 1 H); 2.60 (m, 2 H); 2.24 (t, J=7.8 Hz, 2 H); 2.09 (t, J=8.1 Hz, 1 H); 1.84 (m, 2 H); 1.73 (m, 1 H); 1.60 (m, 1 H); 1.43 (m, 2 H); 0.85((m, 14 H); 0.74 (m, 2 H). MS (m/z) 593 (M+1)$^+$.

Example 31

Synthesis of Compound 188

The synthesis of compound 188 proceeds analogous to the procedures described in example 27, steps 2 to 5, using 40 mg of resin 44 and 3 (71 mg, 0.26 mmol). After cleavage from thee resin, 188 (20 mg, 58% ) was isolated by preparative reversed-phase HPLC. Gradient: 65% A, 5 min isocratic, then in 7 min to 30% A; RT 9.5 min). $^1$H NMR (300 MHz, DMSO-d$_6$): δ 8.04 (m, 2 H) 7.96 (d, J=7.8 Hz, 1 H); 7.55 (d, J=7.8 Hz, 1 H); 7.33 (d, J=8.1 Hz, 1 H); 7.28 (d, J=8.0 Hz, 1 H); 7.14 (s, 1 H); 7.12 (t, J=7.1 Hz, 1 H); 7.03 (t, J=6.9 Hz, 1 H); 4.93 (s, 2 H); 4.31 (m, 2 H); 3.99 (dd, J$_1$=8.0 Hz, J$_2$=5.5 Hz, 1 H); 3.73 (d, J=6.6 Hz, 2 H); 3.32 (m, 2 H); 2.81 (t, J=7.7 Hz, 2 H); 2.71 (m, 2 H); 2.24 (m, 3 H); 1.85 (m, 2 H); 1.74 (m, 1 H); 1.60 (m, 1 H); 1.49 (m, 2 H); 0.88 (n, 12 H). MS (m/z) 664 (M+1)$^+$.

Example 32

Synthesis of Compound 190

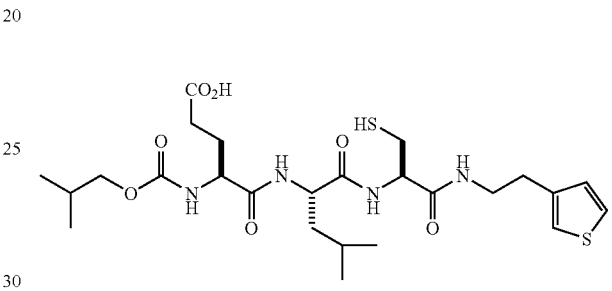

The synthesis of compound 190 proceeds analogous to the procedures described in example 27, steps 2 to 5, using 40 mg of resin 44 and 1 (33 mg, 0.26 mmol). After cleavage from the resin, 190 was isolated by preparative reversed-phase HPLC. Gradient: 65% A, 5 min isocratic, then in 7 min to 30% A; RT 10.3 min. $^1$H NMR (300 MHz, DMSO-d$_6$): δ 12.0 (bs, 1 H), 7.98 (m, 2 H) 7.93 (d, J=7.8 Hz, 1 H), 7.43 (dd, J=3.0, 4.9 Hz, 1 H),7.26 (d, J=7.7 Hz, 1 H), 7.18 (bs, 1 H); 6.99 (d, J=4.9, 1 H); 4.27 (m, 2 H); 3.97 (app dd, J=7.6, 13.4 Hz, 1 H); 3.72 (d, J=6.6 Hz, 2 H); 3.34 (m, 2 H); 2.72 (t, J=7.1 Hz, 2 H); 2.59–2.80 (m, 2 H); 2.24 (t, J=7.8 Hz, 2 H); 2.16 (t, J=8.1 Hz, 1 H); 1.83 (m, 2 H); 1.72 (m, 1 H); 1.59 (m, 1 H); 1.45 (m, 2 H); 0.86 (m, 9 H); 0.83 (d, J=6.6 Hz, 3 H). MS (m/z) 573 (M+1)$^+$.

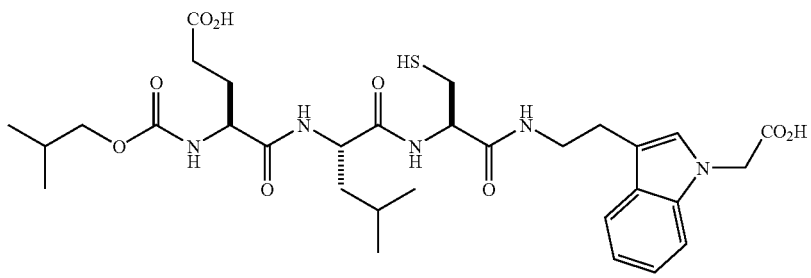

Example 33

Synthesis of Compound 163

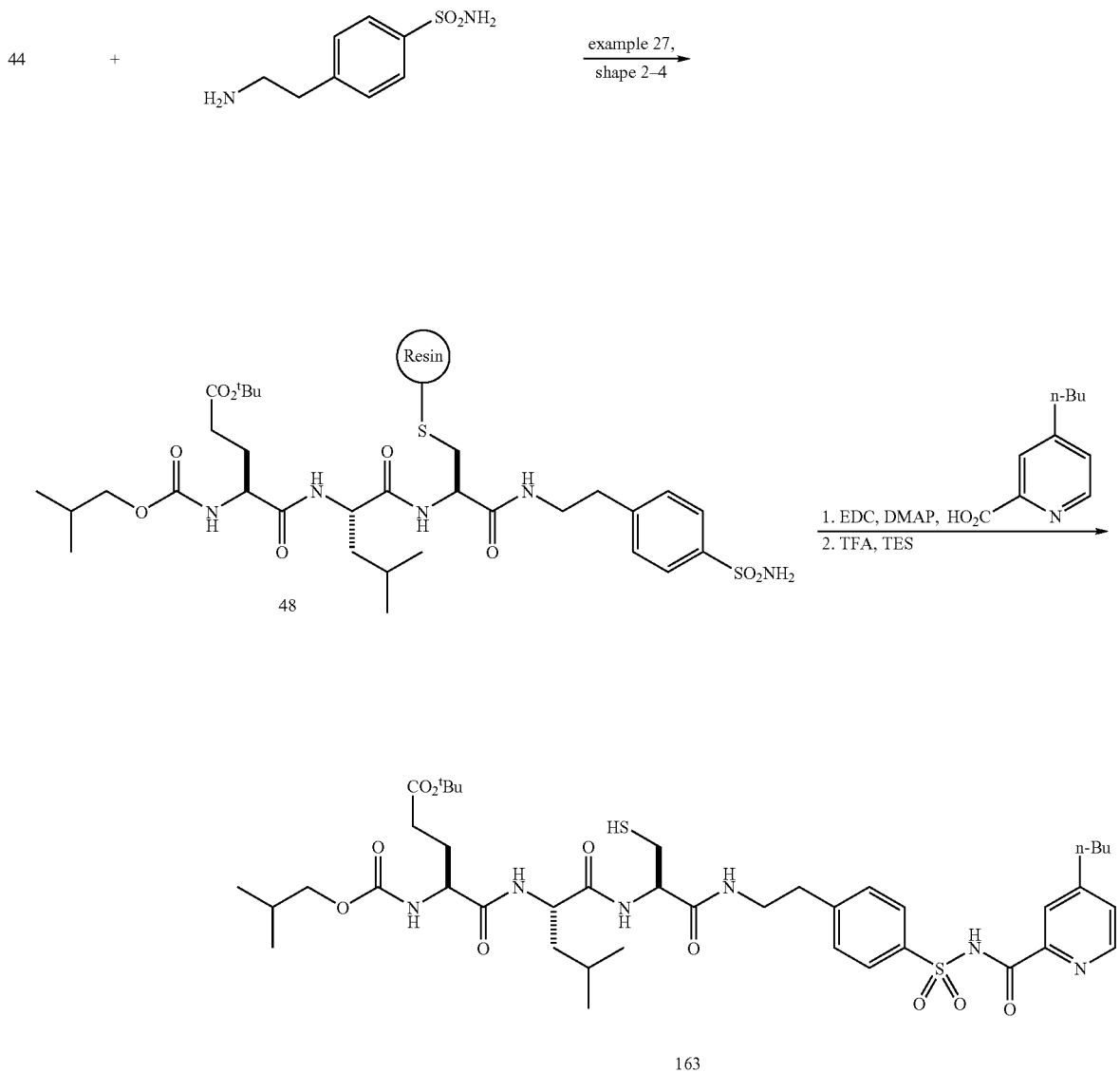

Synthesis of Resin 48

The synthesis of resin 48 is analogous to the procedures described in example 27 steps 2 to 4, using 120 mg of resin 44 and (4-(2-aminoethyl)-sulfonamide (156 mg, 0.78 mmol). For this coupling step a mixture of DMF/DCM(1/1, v/v, 3 mL) was used. Fmoc-L-Leucine and 22 were coupled as described to give resin 48.

Acylation of Resin 48

30 mg of resin 48 (0.038 mmoles) were suspended in DCM (2 mL) and treated with EDC (73 mg, 0.38 mmoles), DMAP (46 mg, 0.38 mmoles), and fusaric acid (68 mg, 0.38 mmoles) for 4 h. The resin was drained, washed with DMF and DCM, and the coupling repeated. Then the resin was drained, washed (2×DMF, 2×DCM) and dried under vacuum. Cleavage was achieved by treating the resin with TFA/DCM/H$_2$O 50:45:5 (2 mL) in the presence of of TES (0.02 mL) for 30 minutes, followed by filtration. Evaporation of the filtrate afforded 35 mg of an orange oil which was purified by preparative RP-HPLC. Gradient: 70% A, 5 min isocratic, then in 7 min to 30% A. Compound 163 was obtained as the trifluoroacetate after lyophilization. $^1$H NMR (300 MHz, DMSO-d$_6$): δ 8.55 (s, 1 H); 7.99 (m, 2 H); 7.94(d, J=8.3 Hz, 2 H); 7.94 (m, 1 H); 7.88 (s, 1 H); 7.87 (d, J=1.8 Hz, 1 H); 7.46(d, J=8.3 Hz, 2 H); 7.28(d, J=7.8 Hz, 1 H); 4.25 (m, 2 H); 3.97 (m, 1 H); 3.73 (d, J=6.7 Hz, 2 H); 2.81 (t, J=6.9 Hz, 2 H); 2.68 (m, 4 H); 2.25 (d, J=6.7 Hz, 2 H); 2.15 (t, J=8.0 Hz, 1 H); 1.80 (m, 3 H); 1.57 (m, 3 H); 1.46 (m, 2 H); 1.29 (m, 2 H); 0.86 (m, 15 H). MS (m/z) 807 (M+1)$^+$.

Example 34

Synthesis of Compound 321

Step 1:

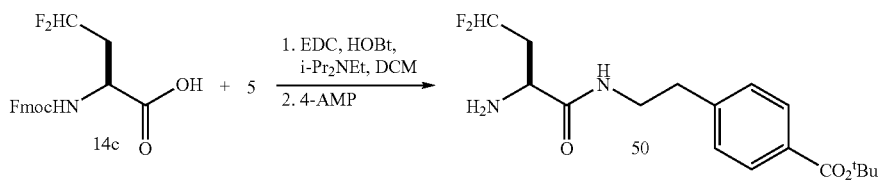

Step 2:

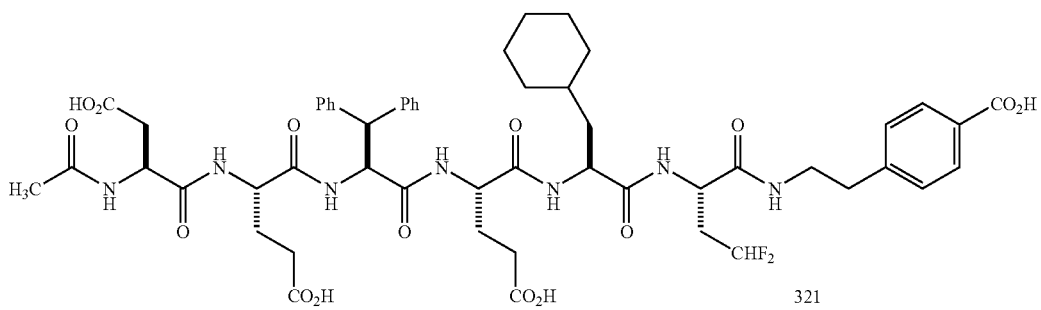

For the synthesis of 321 the protected pentapeptide Ac-Asp(OtBu)-Glu(OtBu)-Dif-Glu(OtBu)-ChaOH (49) was used. Peptide 49 can be synthesized by classical solid-phase synthetic methods, or by a solution phase protocol using Fmoc-protection and deprotection of the Fmoc group with 4-AMP.

Step 1: Synthesis of 50

Acid 14c (700 mg, 1.94 mmol) was coupled to amine hydrochloride 5 (549 mg, 2.13 mmol) in DCM (20 mL) using EDC (409 mg, 2.13 mmol) and HOBt (326 mg, 2.13 mmol) in the presence of DIPEA (376 mg, 2.91 mmol) overnight at room temperature. An acid-base extractive workup gave the crude product, which was purified by flash chromatography (PE/EtOAC 3:1, 1% ethanol) to give a colorless foam (787 mg). 230 mg (0.42 mmol) of this material were dissolved in DCM (8 mL) and treated with 4-AMP (1.92 g, 16.8 mmol). After 20 min EtOAc (60 mL) was added and the solution thoroughly extracted with phosphate buffer (pH 5.5). After dryingiand evaporation amine 50 (135 mg, 94%) was obtained as a colorless oil in sufficient purity. $^1$H-NMR (DMSO-$d_6$) δ 8.07 (bs, 1 H); 7.81 (d, J=7.9 Hz, 1 H); 7.32 (d, J=7.9 Hz, 1 H); 6.08 (tt, J=56.9, 4.5 Hz, 1 H); 3.3–3.4 (m, 2 H); 2.79 (t, J=6.9 Hz, 2 H); 2.0–2.2 (m, 1 H); 1.8–1.95 (m, 1 H); 1.53 (s, 9 H). MS (m/z) 343 (M+H)$^+$.

Step 2: Synthesis of 321

Pentapeptide 49 (50 mg, 0.051 mmol) was dissolved in DMF (0.8 mL). HATU (21 mg, 0.056 mmol) and amine 50 (20 mg, 0.06 mmol) were added, followed by 2,6-lutidine (11 mg, 0.10 mmol). After stirring overnight, EtOAc (50 mL) was added, the solution was extracted with hydrochloric acid (1 N), saturated aqueous sodium hydrogen carbonate and brine. Drying and evaporation gave a colorless solid, which was dissolved in a mixture of DCM/TFA/water (60:35:5, 10 mL) and left for 30 min. Evaporation gave an offwhite solid, which was purified by preparative RP-HPLC. Gradient: 70% A, 3 min isocratic, then in 7 min to 35% A; RT 8.6 min. $^1$H-NMR (DMSO-$d_6$) δ 8.15 (d, J=7.5 Hz, 1 H); 8.08 (d, J=8.1 Hz, 1 H); 7.80–8.00 (m, 6 H); 7.41 (d, J=6.6 Hz, 1 H); 7.02–7.38 (m, 14 H); 5.96 (tt, J=56.1, 4.6 Hz, 1 H); 5.19 (app. t, J=9.3 Hz, 1 H); 4.48 (m, 1 H); 4.38 (d, J=10.4 Hz, 1 H); 4.34 (m, 1 H); 4.01–4.18 (m, 3 H); 3.4 (m, 2 H, under water from DMSO); 2.78 (t, J=7.0 Hz, 2 H); 2.39–2.52 (m, 2 H); 1.98–2.20 (m, 6 H); 1.84 (s, 3 H); 1.50–1.85 (m, 9 H); 1.33–1.40 (m, 2 H); 1.08–1.31 (m, 4 H); 0.74–0.92 (m, 2 H). MS (m/z) 1079 (M+H)$^+$.

Example 35

Synthesis of Compound 522

Step 1

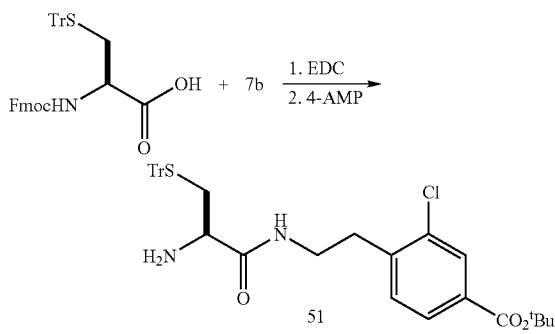

Step 2

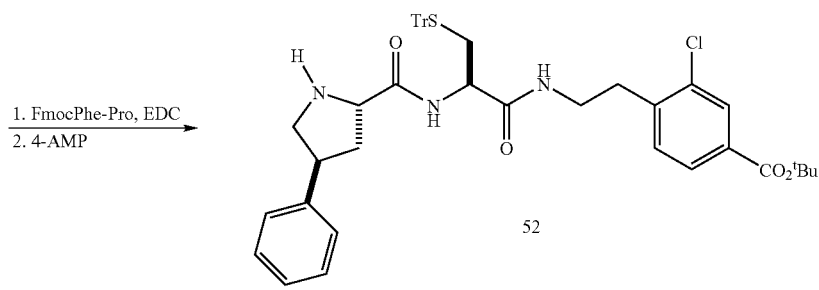

Step 3

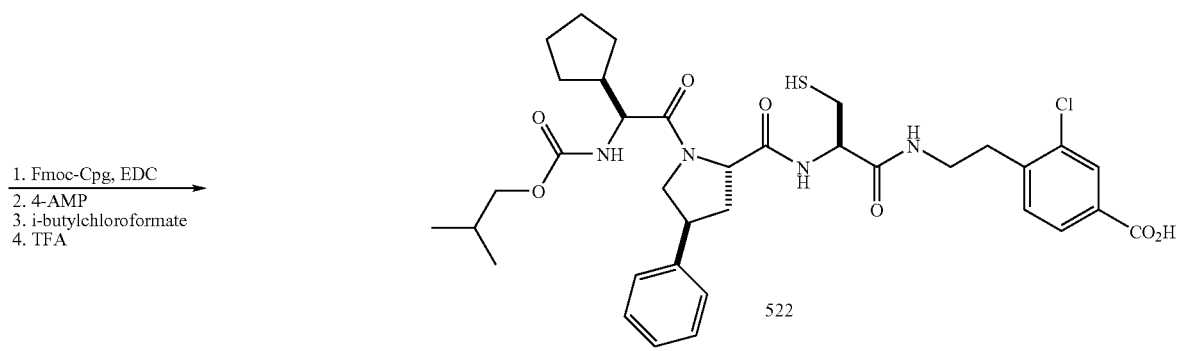

Step 1: Synthesis of 51

To a stirred solution of Fmoc-S-trityl-cysteine (321 mg, 0.548 mmol) in DCM (3 mL) were 7b (140 mg, 0.548 mmol), HOBt (89 mg, 0.659 mmol) and EDC (126 mg, 0.659 mmol). The reaction mixture was stirred at room temperature for 8 hours, diluted with DCM and extracted with HCl (1 N), NaOH (1 N), brine. The oily residue was dissolved in CHCl$_3$ (5 mL) and the solution was cooled in an ice bath. 1.25 mL of 4-AMP were added and the mixture was stirred at room temperature for 1 h. The solvent was evaporated under vacuo and the residue was purified by flash column chromatography on silica gel, eluting with PE/EtOAc (80/20 v/v and then 20/80 v/v) to give 51 (330 mg, 60%). $^1$H NMR (DMSO-d$_6$) δ 7.92 (t, J=6.0 Hz, 1 H), 7.81 (d, J=1.6 Hz, 1 H), 7.65 (dd, J=8.0, 1.6 Hz, 1 H), 7.38–7.22 (m, 16 H), 3.30–3.20 (m, 2 H), 3.06 (dd, J=7.6, 5.6 Hz, 1 H), 2.88 (t, J=6.6 Hz, 2 H), 2.33–2.29 (m, 1 H), 2.12 (dd, J=7.79, 11.6 Hz, 1 H), 1.53 (s, 9 H).

Step 2: Synthesis of 52

To a solution of 51 (190 mg, 0.316 mmol) and (2S,4S)-Fmoc-4-phenyl-pyrrolidine-2-carboxylic acid (131 mg, 0.316 mmol) in CH$_2$Cl$_2$ (2 mL), HOBt (51 mg, 0.379 mmol) and EDC (73 mg, 0.379 mmol) were added and the resulting mixture was stirred at room temperature over night. After a work-up as described above and deprotection of the Fmoc group as described in step 1, the residue was purified by flash column chromatography, eluting with petroleum ether/ethyl acetate (80/20 and then 20/20 v/v) to obtain 52 as a white solid in (130 mg, 53%). MS (m/z) 774.4 (M+1)$^+$.

Step 3: Synthesis of 522

To a solution of 52 (40 mg, 0.052 mmol) in CHCl$_3$ (2 mL) were added Fmoc-cyclopentylglycine (28 mg, 0.077 mmol), HOBt (14 mg, 0.103 mmol) and EDC (20 mg, 0.103 mmol) 0.014 g (0.103 mmol). After being stirred at room temperature for 24 hours, the mixture was diluted with DCM and extracted as described in step 1. The organic layer was dried (Na₂SO₄) and concentrated in vacuo. The oily residue was purified by flash column chromatography on silica gel eluting with PE/EtOAc (1/1 v/v) to yield the coupling product (30 mg), which was deprotected with 4-AMP (30 equ.) in CHCl3 (1 mL) at 0° C. for 0.5 hr. After evaporation of the solvent, the crude was filtered on silica gel eluting with PE/EtOAc (4:1) to remove fulvene, then PE/EtOAc (1:1.7) to obtain the amine. This compound was dissolved in DCM (1 mL) and 0.1 mL of DIPEA and the solution was cooled at 0° C. and treated with 1 equiv. of isobutylchloroformate. The reaction mixture was allowed to warm up to room temperature, diluted with DCM and partitioned with HCl (1 N). The organic extract was washed with brine, dried over Na₂SO₄, filtered and concentrated under vacuum. The oily residue was stirred for 4 hours in a mixture of DCM/TFA (1:1, 1 mL) in the presence of 20 equ. of TES. After evaporation of the solvents, the residue was purified by preparative RP-HPLC (RP 18, 7 um) Gradient: 70% A to 100% of B in 15 min. 8 mg (0.011 mol) of 522 were isolated. $^1$H NMR (DMSO-d₆, 300 MHz, 300 K) δ 8.07 (d, J=8.2. Hz, 1 H), 7.99 (t, J=5.4 Hz, 1 H), 7.88 (s, 1 H), 7.80 (dd, J=7.9 Hz, J=1.4 Hz, 1 H), 7.45 (d, J=7.9 Hz, 1 H), 7.35–7.29 (m, 5 H), 4.52 (dd, J=7.4 Hz, J=2.5 Hz, 1 H), 4.28 (m, 1 H), 4.42–4.05 (m, 2 H), 3.73–3.58 (m, 4 H), 3.41 (m, 1 H), 2.92 (t, J=6.7 Hz, 2 H), 2.80–2.67 (m, 2 H), 2.35 (t, J=8.7 Hz, 1 H), 2.30–2.16 (m, 3 H), 1.82–1.15 (m, 10 H) 0.92–0.84 (m, 6 H).

Example 36

Synthesis of Compound 523

Step 1:

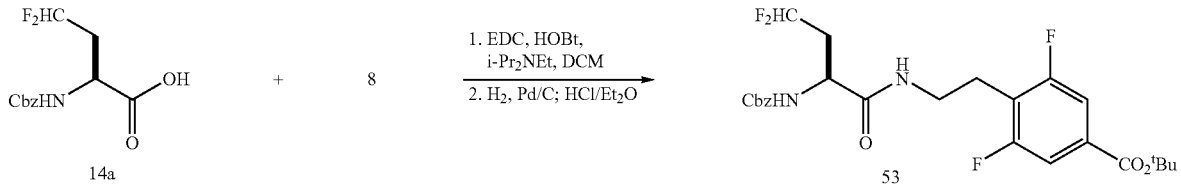

Step 2:

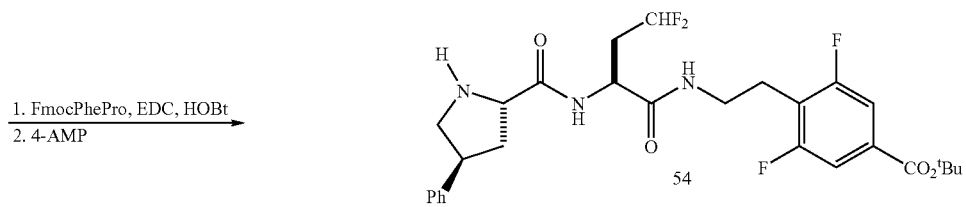

Step 3:

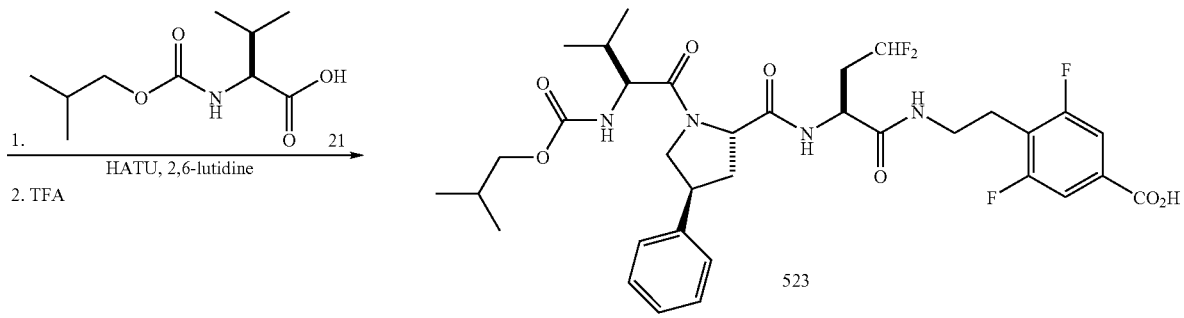

Step 1: Synthesis of 53

EDC (0.9 g, 4.8 mmol) and HOBt (0.7 g, 4.8 mmol) were added to a stirred solution of compound 14a (1.2 g, 4.4 mmol) in DCM (15 ml). The mixture was cooled at 0° C. in an ice bath, then a solution of compound 8 (1.2 g, 4.4 mmol), DIPEA (0.8 ml, 4.4 mmol) in DCM (5 ml) was added dropwise over 5 min. The ice bath was removed and the reaction stirred at room temperature for 4 h(TLC: PE/EtOAc 2/1+1% acetic acid). The reaction was diluted with EtOAc (200 ml) and washed with 1 M HCl (2×50 ml), saturated aqueous sodium hydrogencarbonate and brine. The crude product was purified by flash chromatography (PE/EtOAc 3:1+1% EtOH) to give 1.73 g of coupling product, which was immediately deprotected.

The foregoing compound was dissolved in MeOH (25 ml) and cooled to 0° C., 100 mg of Pd/C (10% Pd) were added, the ice bath removed and the reaction was stirred under hydrogen atmosphere for 1 h. After removal of the catalyst by filtration and evaporation of the solvent, the residue was dissolved in DCM and hydrogenchloride (3.6 ml, 1 M solution in diethyl ether). After removal of the solvents 1.42 g (78%) of amine hydrochloride 53 were obtained as a colorless solid. $^1$H-NMR (CDCl$_3$) δ 1.52 (s, 9 H), 2.53 (m, 2 H), 2.89 (m, 2 H), 3.26 (m, 1 H), 3.59 (m, 1 H), 4.52 (bs, 1 H), 6.04 (bt, J=55.2 Hz, 1 H), 7.39 (d, J=7.5, Hz 2 H), 8.16 (s, 1 H), 8.32 (s, 3 H). MS (m/z) 379 ((M+H)$^+$, free amine).

Step 2: Synthesis of 54

(2S,4S)-Fmoc-4-phenyl-pyrrolidine-2-carboxylic acid (269 mg, 0.65 mmol) was dissolved in DCM (5 mL), EDC (138 mg, 0.72 mmol) and HOBt (110 mg, 0.72 mmol) were added at 0° C., followed by 52 (270 mg, 0.65 mmol) and DIPEA (126 mg, 0.98 mmol). The ice-bath was removed and the solution stirred overnight. Another 5 mL of DCM were the added, together with 4-AMP (2.97 g, 26 mmol). After 30 min the reaction was diluted with EtOAc (100 mL) and extracted thoroughly with phosphate buffer (pH 5.5). 54 was obtained as a yellow foam (346 mg, 96%), which was used without further purification. $^1$H NMR (300 MHz, DMSO-d$_6$): δ 8.43 (d, J=8.4 Hz, 1 H) 8.25 (t, J=5.8 Hz, 1 H); 7.43 (d, J=7.3 Hz, 2 H); 7.13–7.30 (m, 5 H), 5.95 (app tt J=4.5, 56.1 Hz, 1 H), 4.38 (m, 1 H), 3.90 (bd, J=5.9 Hz, 1 H), 3.18–3.39 (m, 4 H), 3.15 (app. t, J=8.4 Hz, 1 H); 2.91 (t, J=9.5 Hz, 1 H); 2.79 (t, J=6.6 Hz, 2 H); 2.0–2.26 (m, 4 H); 1.49 (s, 9 H). MS (m/z) 552.2 (M+1)$^+$.

Step 3: Synthesis of 523

To a solution of 21 (28 mg, 0.13 mmol) in DMF (1 mL) was added HATU (49 mg, 0.13 mmol), 2,6-lutidine (28 mg, 0.26 mmol) and solid 54 (69 mg, 0.12 mmol). The reaction was stirred for 3 h at ambient temperature, then taken into EtOAc and extracted with hydrochloric acid (1 N, 2×), water, saturated aqueous sodium hydrogen carbonate (2×) and brine. The crude product obtained was deprotected with a mixture of TFA/DCM/water (60:35:5, 10 mL) for 30 min at room temperature. Evaporation gave an oil, which was purified by preparative RP-HPLC (gradient: 60% A, 3 min isocratic, then in 9 min to 35% A; RT 12.3 min; 51 mg, 62%). $^1$H-NMR (400 MHz, DMSO-d$_6$) δ 8.17 (d, J=8.6 Hz, 1 H), 7.99 (t, J=5.6 Hz, 1 H), 7.50 (app. d, J=7.5 Hz, 2 H), 7.19–7.35 (m, 5 H), 7.03 (bs, 1 H), 6.02 (ddt, J=3.1, 5.9, 54.4 Hz, 1 H), 4.47 (bs, 1 H), 4.37 (m, 1 H), 4.08 (t, J=6.3 Hz, 2 H), 3.73 (d, J=6.6 Hz, 2 H), 3.61 (m, 2 H), 3.42 (m, 1 H), 3.30 (m, 1 H), 2.85 (t, J=6.8 Hz, 2 H), 2.05–2.31 (m, 4 H); 2.05 (m, 1 H); 1.81 (m, 1 H), 0.88 (m, 12 H). MS (m/z) 695.2 (M+H)$^+$.

Example 37

Synthesis of Compound 526

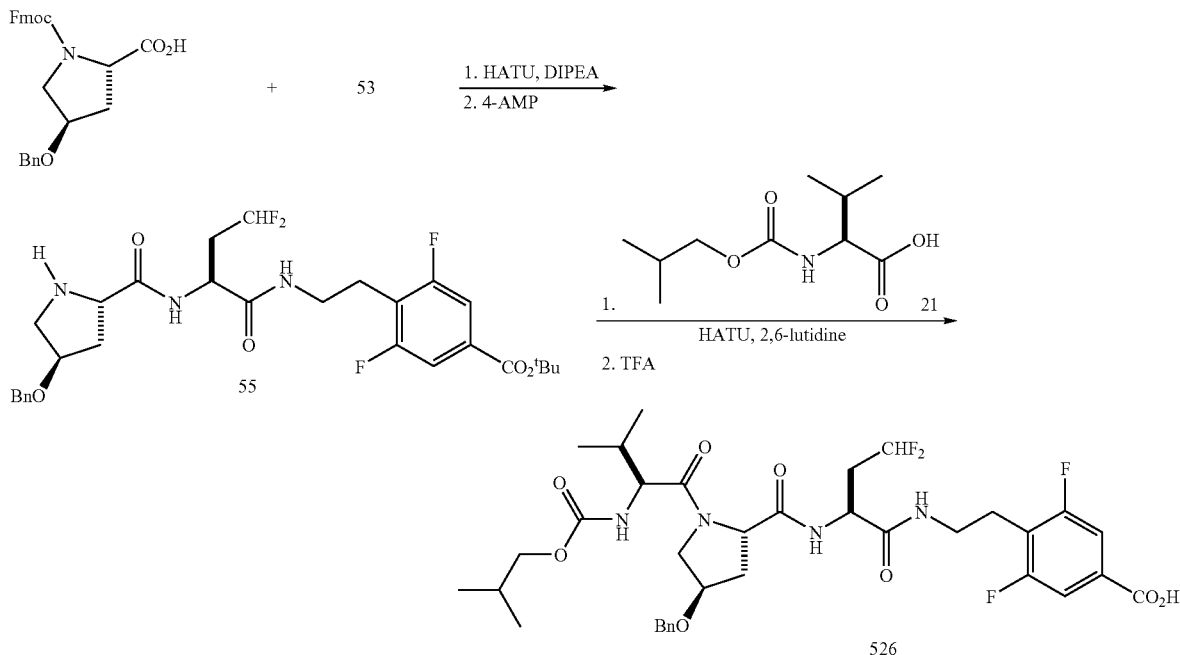

Synthesis of 55

Coupling of 53 (54 mg, 0.13 mmol) and N-Fmoc-O-benzyl-L-trans-4-hydroxyproline (53 mg, 0.12 mmol) was carried out in DCM (2 mL) using HATU (69 mg, 0.18 mmol) and DIPEA (0.042 mL, 0.24 mmol) as described in example 36, step 2. Deprotection with 4-AMP, gave 55 (65 mg, 90%) as a colorless oil. MS (m/z) 582.4 (M+H)$^+$.

Synthesis of 526

Using the procedure described in example 36, step 3, 21 (26 mg, 0.12 mmol 4) was coupled to 55 (65 mg, 0.11 mmol) in DCM (2 mL). After workup and deprotection the crude product was purified by preparative RP-HPLC (Symmetry C18, 19×300 mm; flow 15 mL/min; gradient: 70% A, 3 min isocratic, then in 10 min to 30% A, 2 min isocratic, in 1 min to 10% A; RT 16.2 min; 30 mg (38%). $^1$H-NMR (400 MHz, DMSO-d$_6$) δ 8.37 (d, J=8.4 Hz, 1 H), 8.14 (t, J=5.7 Hz, 1 H), 7.50 (app. d, J=7.2 Hz, 2 H), 7.22–7.40 (m, 6 H), 6.06 (bt, J=56.6 Hz, 1 H), 4.52 (d, J=11.5 Hz, 1 H), 4.45 (d, J=11.5 Hz, 1 H), 4.30 (m, 2 H), 4.24 (bs, 1 H), 4.12 (d, J=11.1 Hz, 1 H), 3.96 (bd, J=8.5 Hz, 1 H), 3.62–3.75 (m, 3 H), 3.37 (m, 1 H), 3.24 (m, 1 H), 2.83 (t, J=6.7 Hz, 2 H), 2.20 (m, 1 H), 2.14 (m, 2 H); 1.93 (m, 2 H); 1.80 (m, 1 H), 0.86 (m, 12 H). MS (m/z) 725.5 (M+H)$^+$.

Example 38

Synthesis of Compound 539

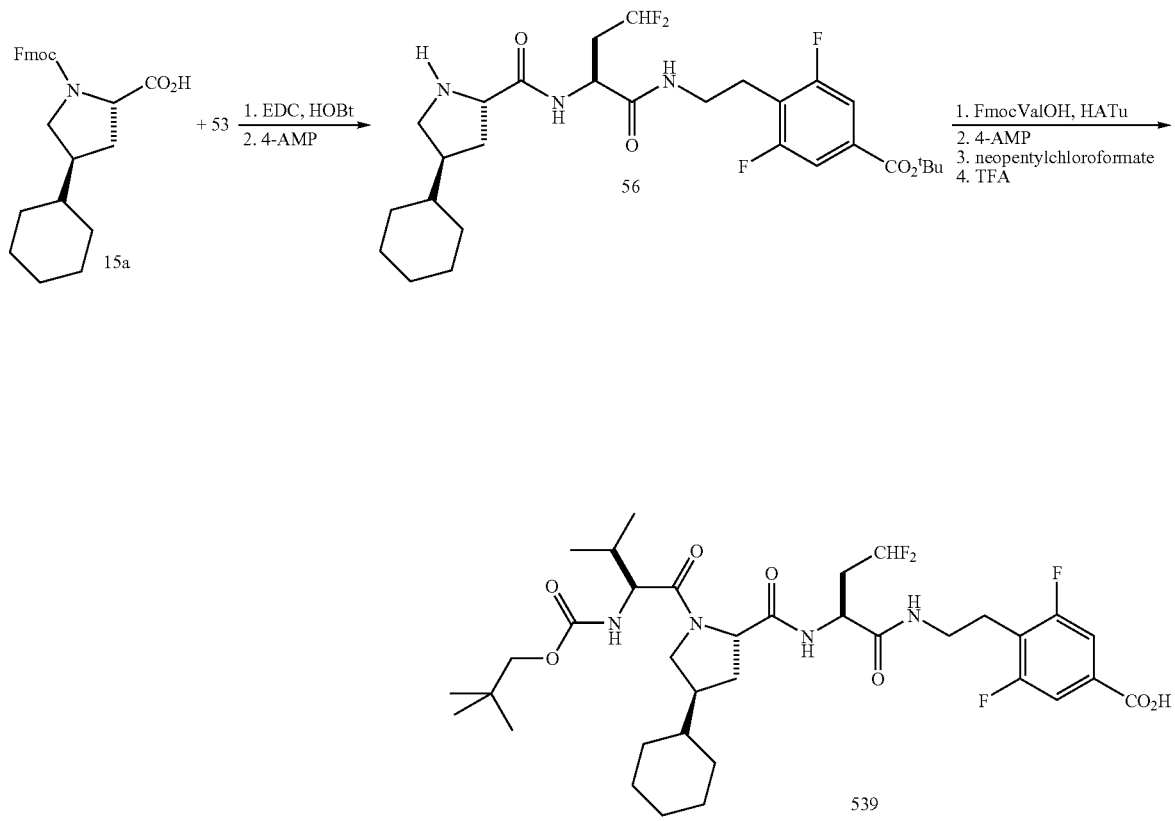

Synthesis of 56

53 (78 mg, 0.19 mmol) and 15a (80 mg, 0.19 mmol) were reacted as described in example 36, step 1 to give after deprotection with 4-AMP 56 as a pale yellow foam, used with no further purification. $^1$H NMR (300 MHz, DMSO-d$_6$): δ 8.64 (d, J=8.0 Hz, 1 H) 8.29 (t, J=5.9 Hz, 1 H); 7.43 (d, J=7.4 Hz, 2 H); 5.95 (app tt J=4.0, 56.3 Hz, 1 H), 4.34 (m, 1 H); 4.02 (m, 1 H); 3.26 (m, 4 H); 2.78 (t, J=6.8 Hz, 2 H); 2.70 (t, J=10.1 Hz, 1 H); 2.03 (m, 3 H); 1.79 (m, 2 H); 1.60 (m, 4 H); 1.50 (s, 9 H); 1.14 (m, 4 H); 0.85 (m, 2 H). MS (m/z) 558 (M+1)$^+$.

Synthesis of 539

To an ice-cold solution of 56 (100 mg, 0.179 mmol), (L)-Fmoc-Val-OH (67 mg, 0.187 mmol) and HATU (102 mg, 0.268 mmol) in DCM (10 ml) was added DIPEA (62 μl, 0.358 mmol). The solution was stirred for two days, diluted with EtOAc (100 ml) and washed with 1N HCl, saturated NaHCO$_3$ and brine (3×50 ml). Drying and evaporation gave the coupling product (150 mg, 91%). The Fmoc group was cleaved with 4-AMP (0.81 ml, 6.8 mmol) in DCM (2.5 ml) for 3 hours at room temp. After dilution of the mixture with EtOAc (50 ml) it was washed with phosphate buffer (pH 5.5, 6×100 ml) and brine (100 ml). The foam obtained 100 mg (100 mg, 89%) of was used with no further purification. A part of this material (80 mg, 0.122 mmol) in DCM (1 ml) and DIPEA (42.5 μl, 0.183 mmol) was treated with a solution of neo-pentyl-chloroformate in DCM (1 ml). The solution was stirred overnight, diluted with EtOAc (30 ml) and washed with 1N HCl, saturated NaHCO$_3$ and brine (3×20 ml). The crude (90 mg) obtained was treated for 3 hours at room temperature with TFA/CH$_2$Cl$_2$/H$_2$O (65:35:5, 15 mL). After removal of the solvents the residue was freeze-dried from CH$_3$CN/H$_2$O 1:1 (50 mL). The powder was purified by preparative RP-HPLC: Symmetry Waters column (C18, 30×50 mm), flow 40 ml/min, gradient linear from 80% to 38% A over 13 minutes, then isocratic (RT 14.6 minutes), 48 mg 0 f 539 (57%).

$^1$H-NMR (DMSO-d$_6$) δ 13.5 (bs, 1 H), 8.18 (d, J=8.5 Hz, 1 H), 8.09 (t, J=5.8 Hz, 1 H), 7.49 (s, 1 H), 7.48 (s, 1 H), 7.26 (d, J=8.5 Hz, 1 H), 5.97 (bt, J=57 Hz, 1 H), 4.30 (m, 2 H), 4.0 (m, 1 H), 3.75 (m, 1 H), 3.33–3.21 (m, 4 H), 2.82 (m, 2 H), 2.08–1.90 (m, 5 H), 1.64 (m, 6 H), 1.13 (m, 4 H), 0.86 (s, 18 H); MS m/z 715.4 (M+H)$^+$.

Example 39

Synthesis of Compounds 551–553

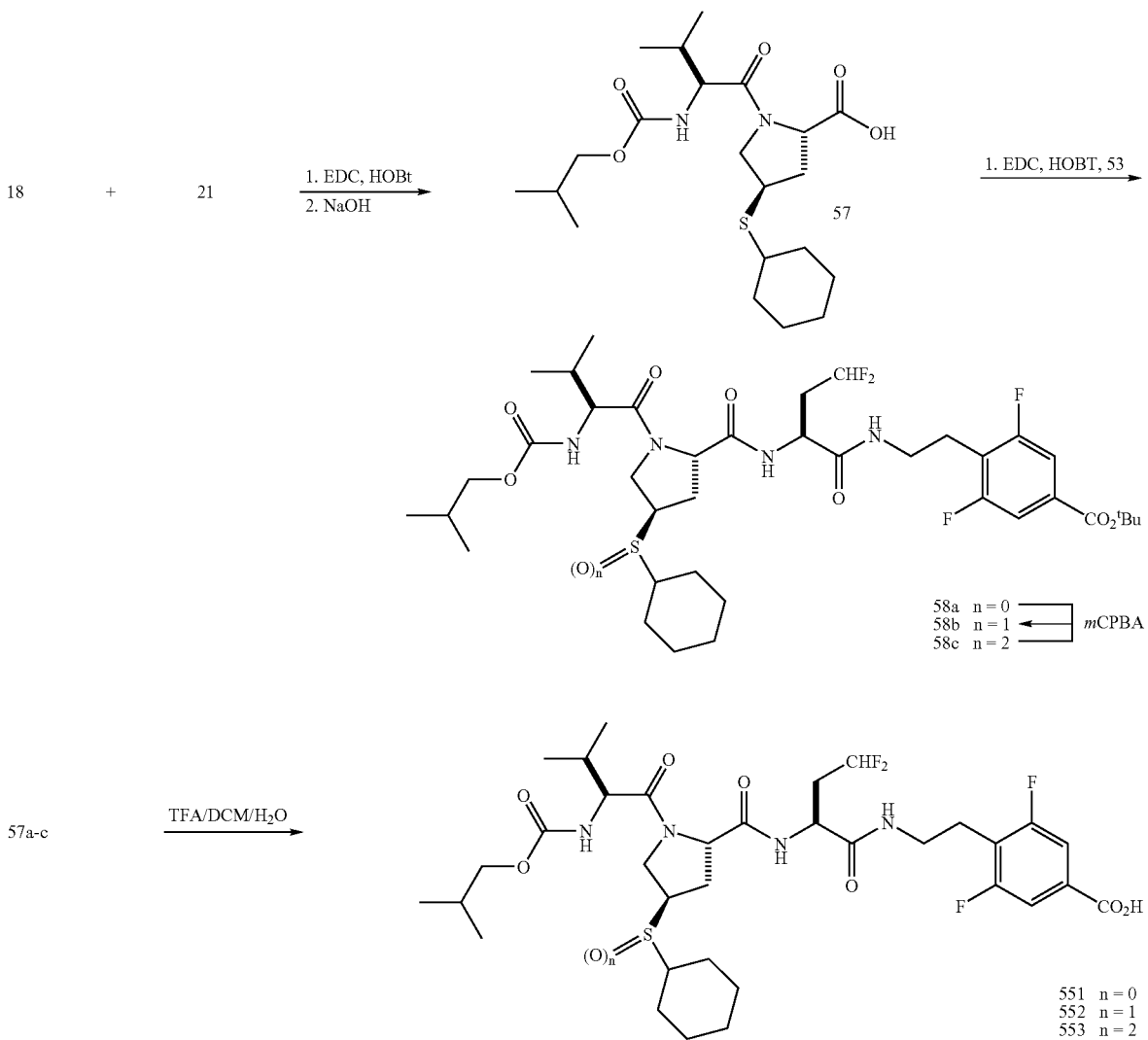

Synthesis of 57

To a solution of the amine hydrogen chloride salt 18 (195 mg, 0.665 mmol) in DCM (8 ml) and DIPEA (0.127 ml, 0.731 mmol) at 0° C. under nitrogen were added 21 (152 mg, 0.698 mmol), HOBt (180 mg, 1.33 mmol) followed EDC (134 mg, 0.698 mmol) and the solution stirred at room teperature overnight. The solution was diluted with EtOAc and the organic phase washed with aqueous HCl (1 N), aqueous saturated NaHCO$_3$, brine, dried (sodium sulfate) and evaporated in vacuo to leave a colourless glass which was purified by flash chromatography (PE/EtOAc) to afford 227 mg (75%) of the coupling product. $^1$H NMR (DMSO-d$_6$, 400 MHz): δ 0.83–0.91 (12 H, m), 1.13–1.33 (7 H, m), 1.51–1.58 (1 H, m), 1.64–1.71 (2 H, m), 1.77–1.95 (4 H, m), 2.03–2.11 (1 H, m), 2.15–2.22 (1 H, m), 2.77–2.86 (1 H, m), 3.51–3.58 (1 H, m), 3.62–3.76 (3 H, m), 3.92–4.09 (5 H, m), 4.33–4.39 (1 H, m), 7.32 (1 H, d, J=8.6 Hz); MS (m/z) 457.1 (M+H)$^+$.

To a solution of the foregoing compound (227 mg, 0.498 mmol) in MeOH (4 ml) was added aqueous NaOH (1 ml, 1 N) and the reaction was stirred at room temperature for 2 hrs. The solution was diluted with EtOAc and acidified with aqueous HCl (1 N). The organic phase was washed with brine, dried (sodium sulfate) and evaporated in vacuo to leave 57 as a white solid (100%). $^1$H NMR (DMSO-d$_6$, 400 MHz): δ 0.83–0.90 (12 H, m), 1.14–1.34 (5 H, m), 1.51–1.58 (1 H, m), 1.64–1.71 (2 H, m), 1.77–1.95 (4 H, m), 2.03–2.10 (1 H, m), 2.15–2.22 (1 H, m), 2.77–2.86 (1 H, m), 3.51–3.58 (1 H, m), 3.61–3.76 (3 H, m), 3.91–3.99 (2 H, m), 4.26–4.32 (1 H, br dd), 7.31 (1 H, d, J=8.7 Hz); MS (m/z) 429.3 (M+H)$^+$.

Synthesis of 58a

To a solution of the acid 57 (178.5 mg, 0.417 mmol) in DCM (6 ml) at 0° C. under nitrogen were added DIPEA (62.2 mg, 0.481 mmol), 53 (181.5 mg, 0.438 mmol), HOBt (112.7 mg, 0.834 mmol) followed EDC (84 mg, 0.438 mmol) and the solution stirred at room temperature overnight. The solution was diluted with EtOAc and the organic phase washed with aqueous HCl (1 N), aqueous saturated NaHCO$_3$, brine, dried (sodium sulfate) and evaporated in vacuo to leave crude 58a (305 mg, 93%) as a white solid. $^1$H NMR (DMSO-d$_6$, 400 MHz): δ 0.84–0.86 (12 H, br d), 1.20–1.37 (5 H, m), 1.53 (10 H, br s), 1.66–1.68(2 H, m), 1.77–1.92 (5 H, m), 2.05–2.18 (3 H, m), 2.78–2.83 (3 H, m), 3.20–3.35 (3 H, m), 3.56–3.65 (2 H, m), 3.66–3.75 (2 H, m), 3.89–3.94 (2 H, m), 4.25–4.30 (1 H, m), 4.34–4.37 (1 H, m), 6.01 (1 H, br t, J$_{HF}$=57.5 Hz), 7.32 (1 H, d, J=8.7 Hz), 7.45 (2 H, d, J=7.2 Hz), 8.09 (1 H, br t), 8.31 (1 H, d, J=8.6 Hz); MS (m/z) 789.4 (MH)$^+$.

Synthesis of 551

A solution of compound 58a (70 mg, 0.089 mmol) in TFA/DCM/H$_2$O (6 ml/3.5 ml/0.5 ml) was stirred for 2 hrs at room temperature. The solvent was removed in vacuo to leave a glass which was purified by reverse phase HPLC (Hibar LiChrosorb RP-18; gradient: 60% A, 2 min isocratic, then in 13 min to 30% A, 5 min isocratic, in 3 min to 10% A). Fractions containing the desired product were pooled and lyophilized to give compound 551. $^1$H NMR (DMSO-d$_6$, 400 MHz): δ 0.83–0.89 (12 H, br d), 1.25–1.31 (5 H, m), 1.48–1.54 (1 H, m)), 1.63–1.69 (2 H, m), 1.84–2.20 (6 H, m)), 2.79–2.88 (5 H, m), 3.52–3.58 (3 H, m), 3.69–3.75 (3 H, m), 3.89–4.00 (2 H, m), 4.25–4.31 (1 H, m), 4.36–4.42 (1 H, m), 5.96 (1 H, br t, J$_{HF}$=56.0 Hz), 6.76 (1 H, br s), 7.44 (2 H, br d, J=7.0 Hz), 7.83 (1 H, br t), 8.01 (1 H, br d); MS (m/z) 733.4 (M+H)$^+$.

Synthesis of 552

To a solution of compound 58a (111 mg, 0.141 mmol) in CHCl$_3$ (2 ml) at 0° C. under nitrogen, mCPBA (technical grade) (32.4 mg, 0.141 mmol) was added and the solution stirred at room temperature for 1 hr. The solution was washed with aqueous saturated NaHCO$_3$, brine, dried (sodium sulfate) and evaporated in vacuo to leave a diastereomeric mixture of sulfoxides 58b as a colorless glass, which were immediately dissolved in a mixture of TFA/DCM/H$_2$O (6.5 ml/3.5 ml/0.5 ml) and stirred at room temperature for 2 hrs. The solvent was removed in vacuo to leave a white residue which was purified by prepaartive RP-HPLC (Hibar LiChrosorb RP-18; gradient: 60% A, 2 min isocratic, then in 13 min to 30% A, 5 min isocratic, in 3 min to 10% A). Fractions containing the desired product were pooled and lyophilized to give compound 552 as a mixture of diastereoisomers (1:1*). $^1$H NMR (DMSO-d$_6$, 400 MHz): δ 0.82–0.89 (12 H, bd), 1.15–1.21 (1 H, m), 1.30–1.39 (4 H, m), 1.60–1.63 (1 H, m), 1.74–2.20 (10 H, m), 2.64–2.70 (1 H, m), 2.79–2.83 (2 H, m), 3.18–3.25 (1 H, m), 3.30–3.39 (1 H, m), 3.59–3.79 (4 H, m), 3.87–4.06 (10 H, m), 4.24–4.34 (1 H, m), 4.35–4.46 (1 H, m), 5.99 (1 H, br t, J$_{HF}$=56.5 Hz), 7.25, 7.37*, (1 H, d, J=8.12, 8.4* Hz), 7.49 (2 H, d, J=7.1 Hz), 8.13–8.19 (1 H, m), 8.35, 8.44* (1 H, d, J=8.8, 8.3* Hz); MS (m/z) 749.6 (M+H)$^+$.

Synthesis of 553

To a solution of compound 58a (98 mg, 0.124 mmol) in CHCl$_3$ (2 ml) at 0° C. under nitrogen, mCPBA (technical grade) (45.04 mg, 0.261 mmol) was added and the solution was stirred at room temperature for 1 hr. The solution was washed with aqueous saturated NaHCO$_3$, brine, dried and evaporated in vacuo to leave 58c as a colourless glass (13) which was dissolved in a mixture of TFA/DCM/H$_2$O (6.5 ml/3.5 ml/0.5 ml) and stirred at room temperature for 2 hrs. The solvent was removed in vacuo to leave a white residue which was purified by preparative RP-HPLC (Hibar LiChrosorb RP-18; gradient: 60% A, 2 min isocratic, then in 13 min to 30% A, 5 min isocratic, in 3 min to 10% A). Fractions containing the desired product were pooled and lyophilized to give compound 553. $^1$H NMR (DMSO-d$_6$, 400 MHz): δ 0.82–0.86 (12 H, br d), 1.12–1.20 (1 H, m), 1.28–1.40 (4 H, m), 1.61–1.64 (1 H, m), 1.76–2.24 (10 H, m), 2.82 (2 H, br t), 3.18–3.36 (3 H, m), 3.66–4.15 (6 H, m), 4.26–4.30 (1 H, m), 4.44–4.48 (1 H, m), 6.00 (1 H, br t, J$_{HF}$=54.5 Hz), 7.35 (1 H, d, J=8.4 Hz), 7.49 (2 H, d, J=7.4 Hz), 8.14 (1 H, br t), 8.44 (1 H, d, J=8.3 Hz); MS (m/z) 765.4 (M+H)$^+$.

Example 40

Synthesis of Compounds 555

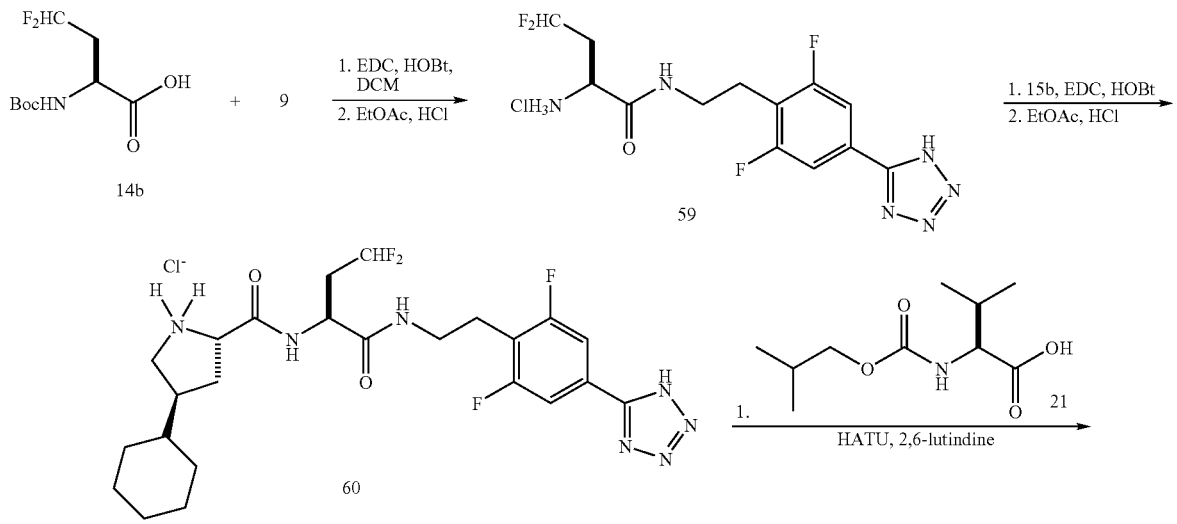

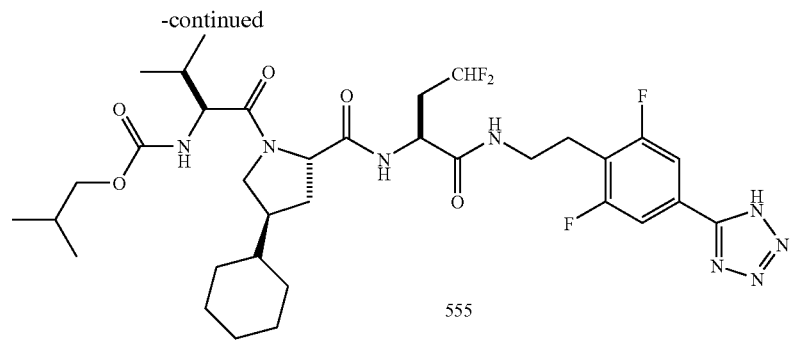

555

Synthesis of 59

The synthesis proceeds analogous to example 36, with the coupling of 14b (71 mg, 0.30 mmol) to 9 (74 mg, 0.33 mol) using EDC (68 mg, 0.36 mmol) and HOBt (55 mg, 0.36 mmol) in DCM/DMF (4 mL, 7:1). The reaction mixture was stirred overnight, and the crude product obtained after workup was dissolved in EtOAc (2 mL). A solution of hydrogen chloride in EtOAc (3.9 M, 2 mL) was added. The mixture was left at room temperature for 1 h and then evaporated to give 58 as a colorless solid (114 mg, quantitative).

Synthesis of 60

The coupling to 15b was performed as described above using 15b (41 mg, 0.14 mmol) and 59 (60 mg, 0.16 mmol) in the presence of EDC (32 mg, 0.17 mmol), HOBt (26 mg, 0.17 mmol) and DIPEA (0.037 mL, 0.21 mmol) in DCM (1.5 mL). After deprotection as described above the amine hydrochloride 59 (66 mg, 90%) was obtained.

Synthesis of 555

60 (66 mg) was added to a stirred solution of 21 (29 mg, 0.13 mmol), HATU (57 mg, 0.15 mmol) and 2,6-lutidine (0.081 mL, 0.44 mmol) in DMF (1 mL). After 3 h at room temperature the reaction was diluted with EtOAc, washed with HCl (1 N), saturated aqueous sodium bicarbonate and brine. Preparative RP-HPLC (Prep NOVAPAK (Waters) C18 cartridge column, 7 micron, 25×100 mm; flow: 10 mL/min; gradient: 50% A, 2 min isocratic, then in 12 min to 20% A; RT 11.0 min) gave 18 mg of 555. $^1$H NMR (300 MHz, DMSO-$d_6$): δ 8.18 (d, J=8.2 Hz, 1 H); 8.11 (m, 1 H); 7.66 (d, J=7.0 Hz, 2 H); 7.25 (d, J=8.4 Hz, 1 H); 5.97 (m, 1 H); 4.31 (m, 2 H); 3.98 (m, 1 H); 3.35 (m, 1 H); 3.26 (m, 2 H); 2.83 (m, 2 H); 2.05 (m, 7 H); 1.89 (m, 2 H); 1.78 (m, 1 H); 1.62 (m, 6 H); 1.10 (m, 4 H); 0.85 (m, 14 H). MS (m/z) 725 (M+1)$^+$.

Example 41

Synthesis of Compound 566

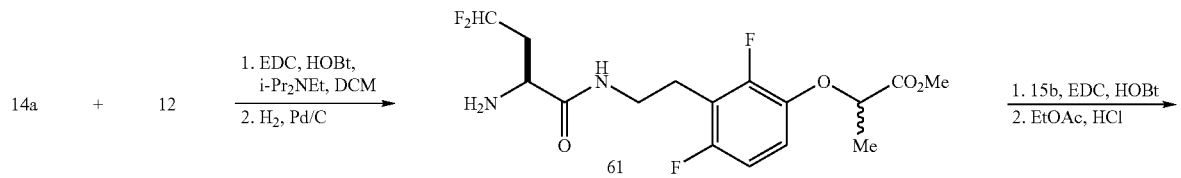

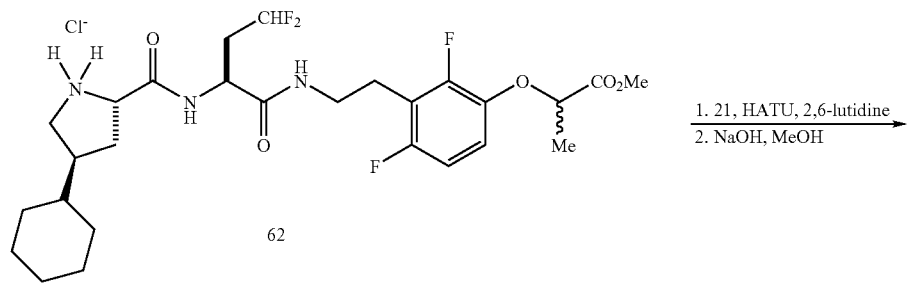

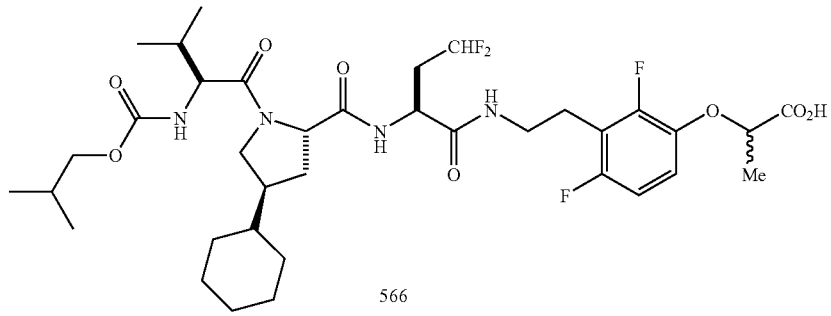

566

Synthesis of 61

As described in example 36, 14a (106 mg, 0.39 mmol) was coupled to 12 (160 mg, 0.39 mmol) using EDC (82 mg, 0.43 mmol) and HOBT (66 mg, 0.43 mmol) in DCM (3 mL). After workup the crude product was purified by flash chromatography (PE/EtOAC 3:1) to afford 110 mg of the coupling product, a part (96 mg, 0.19 mmol) of which was dissolved in methanol (5 mL) containing Pd/C (10 mg, 10% Pd). The reaction was stirred under an atmosphere of hydrogen for 16 h. Filtration and evaporation gave 61 as a colorless oil (68 mg, 95%). MS (m/z) 381 (M+H)$^+$.

Synthesis of 62

The foregoing compound (63 mg, 0.17 mmol) was coupled to 15b (29 mg, 0.19 mmol) analogous to the procedure described in example 36, step 2. After workup, the crude product was treated with a solution of hydrogen cloride in EtOAc (3 M, 2 mL) for 3 h at room temperature. Evaporation gave 62 as a yellow foam (105 mg, quantitative). $^1$H NMR (400 MHz, DMSO-d$_6$): δ 9.58 (bs, 1 H), 8.87 (d, J=8.0 Hz, 1 H), 8.50 (bs, 1 H); 8.38 (d, J=6.8 Hz, 1 H), 6.93 (app. d, J=7.3 Hz, 2 H), 6.03 (bt, J=56.3 Hz, 1 H), 4.95 (q, J=6.7 Hz, 1 H), 4.38 (m, 1 H), 4.21 (m, 1 H), 3.67 (s, 3 H), 3.19 (m, 2 H); 2.82 (m, 2 H), 2.76 (m, 2 H); 2.15 (m, 1 H); 2.04 (m, 1 H); 1.89 (m, 3 H); 1.64 (m, 5 H); 1.49 (d, J=6.7 Hz, 3 H), 1.19 (m, 4 H); 0.85 (m, 2 H). MS (M/Z) 725 (M+1) MS (M/Z) 745 (M+H). MS (M/Z) 560 ((M+H)$^+$, free amine).

Synthesis of 566

To compound 62 (59 mg, 0.1 mmol) was coupled 21 (24 mg, 0.11 mmol) as described in example 36, step 3. The crude product obtained after work-up was dissolved in methanol (2 mL). Sodium hydroxide (1 N, 1 mL) was added and the reaction stirred at room temperature for 20 min. The solution was diluted with water and acetonitrile and 566 isolated by preparative RP-HPLC. Column: Waters Nova-Pak HR C18 cartridge (60 micron, 25×100 mm); flow 10 mL/min; gradient 50% A, 1 min isocratic, in 12 min to 15% A. 32 mg of a colorless powder (RT 12.9 min) was obtained after lyophilization. $^1$H NMR (2, diastereomers, 1:1; 400 MHz, DMSO-d$_6$): δ 13.0 (bs, 1 H), 8.20 (d, J=6.8 Hz, 1 H), 8.11 (bs, 1 H); 7.26 (d, J=8.5 Hz, 1 H), 6.92 (m, 2 H), 5.98 (bt, J=54.1 Hz, 1 H), 4.80 (bs, 1 H), 4.32 (m, 2 H), 4.00 (m, 1 H), 3.74 (m, 3 H), 3.28 (m, 2 H); 3.16 (m, 1 H), 2.74 (m, 2 H); 2.08 (m, 4 H); 1.91 (m, 2 H); 1.80 (m, 1 H); 1.64 (m, 5 H); 1.48 (d, J=6.7 Hz, 3 H); 1.13 (m, 4 H); 0.85 (m, 14 H); MS (m/z) 745.5 (M+H)$^+$.

Example 42

Synthesis of Compound 616

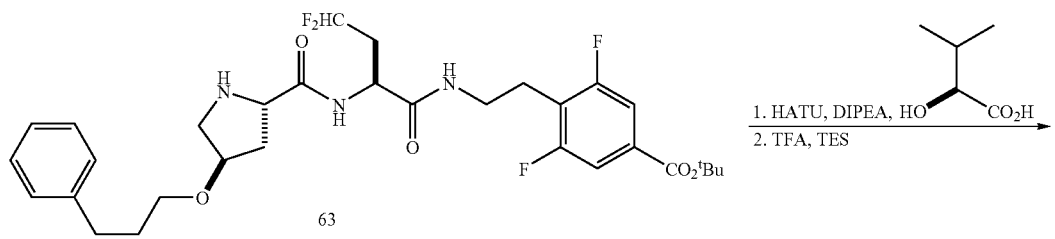

63

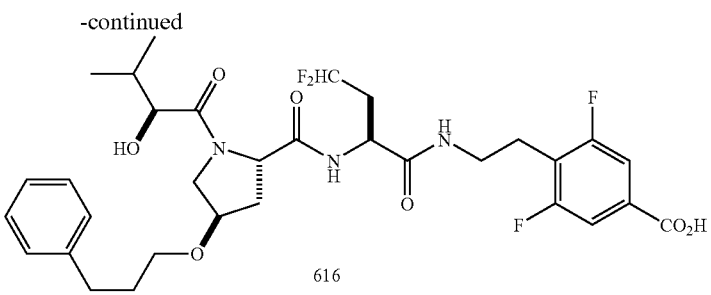
616

A solution of 53 (44 mg, 0.12 mmol), 20 (50 mg, 0.1 mmol) and HATU (60 mg, 0.16 mmol) in DCM (1 mL) and DIPEA (0.037 mL, 0.2 mmol) was stirred at room temperature overnight. The solid obtained after workup from EtOAc was deprotected using 4-AMP as described in example 36. Crude 63 (44 mg, 72%) was used without further purification. MS (m/z) 610 (M+H)$^+$.

To a stirred solution of 63 (24 mg, 0.04 mmol) and HATU (18 mg, 0.048 mmol) in DCM/DMF (1:1, 1 mL) was added DIPEA (0.015 mL, 0.09 mmol). Workup after 2 d gave an orange oil (25 mg), which was deprotected with TFA/DCM/H$_2$O (65:30:5, 1 mL) for 30 min at room temperature. The crude product obtained after evaporation of the solvents was purified by preparative RP-HPLC (gradient: 70% A, 3 min isocratic, in 15 min to 10% A; 8 mg, 31%). $^1$H-NMR (400 MHz, DMSO-d$_6$, 10:1 mixture of rotamers) δ 13.4 (bs, 1 H), 8.33 (d, J=8.8 Hz, 1 H), 8.09 (t, J=6.2 Hz, 1 H), 7.46 (app. d, J=7.9 Hz, 2 H), 7.23 (m, 2 H), 7.15 (m, 3 H), 6.01 (bt, J=56.4 Hz, 1 H), 4.30 (m, 2 H), 4.06 (bs, 1 H), 3.87 (d, J=5.5 Hz, 1 H), 3.73 (d, J=11.4 Hz, 1 H), 3.49 (dd, J=3.9, 11.4 Hz, 1 H), 3.35 (m, 2 H), 3.19 (m, 2 H), 2.79 (t, J=6.8 Hz, 2 H), 2.57 (d, J=7.6 Hz, 2 H), 2.12 (m, 2 H), 2.00 (m, 1 H); 1.70–1.87 (m, 4 H), 0.83 (d, J=6.7 Hz, 3 H), 0.75 (d, J=6.7 Hz, 3 H). MS (m/z) 654.4 (M+H)$^+$.

mg, 0.060 mmol) and HATU (23 mg, 0.060 mmol) were added at 0° C., followed by 2,6-lutidine (14 μl, 0.12 mmol). The cooling bath was removed and the resulting solution stirred overnight After dilution with EtOAc the organic phase was washed with aqueous hydrochloric acid (1 N, 2×), saturated aqueous sodium bicarbonate (2×) and brine. Drying over sodium sulfate and evaporation gave a solid, which was purified by Biotage (column 12×7.5; PE/EtOAc 7:3). MS (m/z) 692 (M+H)$^+$.

The foregoing compound (24 mg, 0.034 mmol) was treated with TFA/DCM/H2O (65:35:5, 1 mL), for 30 min at room temperature. The solvents were removed under vacuum, taken up with Et$_2$O and concentrated to give a white solid.

$^1$H NMR (DMSO-d$_6$): δ 8.25 (d, J=8.35 Hz, 1 H), 8.10 (t, J=5.83 Hz, 1 H), 7.45 (d, J=7.37 Hz, 2 H), 7.24 (m, 5 H), 5.96 (tt, J=56.5, 4.7 Hz, 1 H), 4.43 (t, J=6.55 Hz, 1 H), 4.30 (m, 1 H), 3.97 (dd, J=8.53, 6.07 Hz, 1 H), 3.86 (d, J=6.20 Hz, 1 H), 3.57 (m, 2H), 3.38 (m, 2 H, under water), 3.19 (m, 2H), 2.79 (t, 6.54 Hz, 2 H), 2.16 (m, 2H), 2.09 (m, 1 H), 1.60 (m, 6 H), 1.06 (m, 4H). MS (m/z) 636 (M+H)$^+$.

Example 43

Synthesis of Compound 636

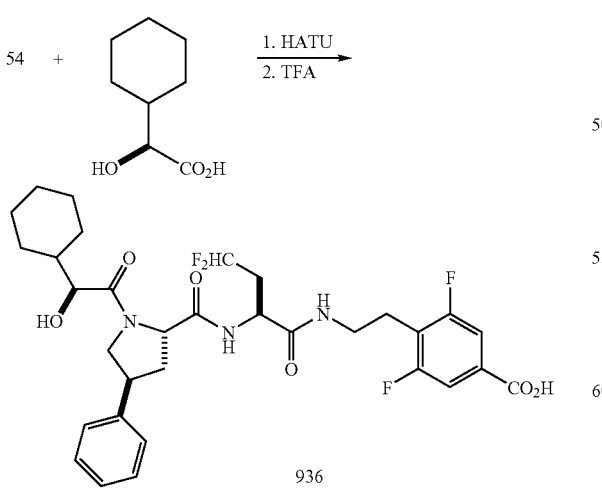
936

The dipeptide 54 (30 mg, 0.054 mmol) was dissolved in DCM/DMF(1:1, 2 mL). (S)-hexahydromandelic acid (9.5

Example 44

Synthesis of Compound 708a,b

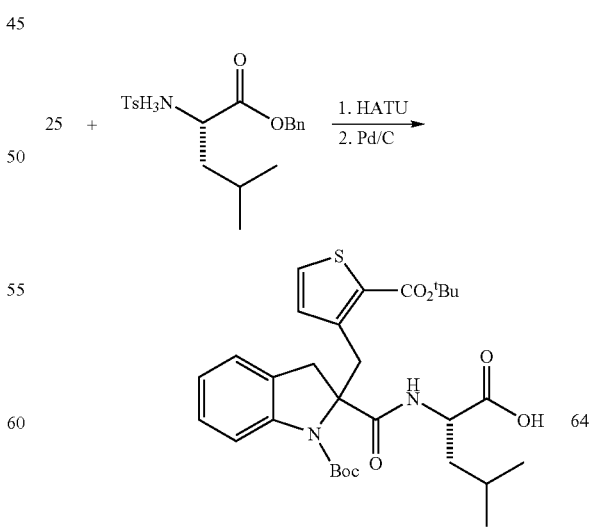

-continued

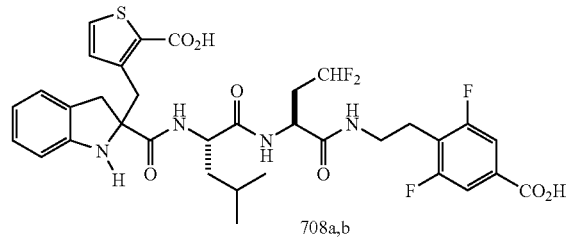

708a,b

Synthesis of 64

To a solution of acid 25 (755 mg, 1.643 mmol), (L)-Leu-OBn tosylate (776 mg, 1.971 mmol) and HATU (687 mg, 1.807 mmol) in DCM (150 ml) cooled to 0° C. was added DIPEA (0.53 ml, 4.11 mmol). The cooling bath was removed and the mixture stirred at room temperature for two days. The reaction mixture was diluted with EtOAc (400 ml), washed with 1 N aqueous HCl, saturated aqueous NaHCO$_3$ and brine. Drying and evaporation gave the coupling product as a mixture of two diastereomers (1.10 g, 100%). MS (m/z) 663.8 (M+H)$^+$.

To a solution of above compound (1.09 g, 1.6 mmol) in MeOH (75 ml) was added Pd/C 30% (230 mg). The reaction mixture was stirred at room temperature under hydrogen (atmospheric pressure) for 18 hours. Dilution with EtOAc, filtration and evaporation of the solvents gave indoline 64 in quantitative yield. $^1$H-NMR (DMSO-d$_6$) δ 7.75 (d, J=Hz, 1 H), 7.60 (d, J=Hz, 1 H), 7.50 (bs, 2 H), 7.4 (d, J=Hz, 2 H), 7.35 (d, J=Hz, 2 H), 7.0 (m, 2 H), 6.81 (m, 2 H), 6.70 (m, 2 H), 6.52–6.60 (m, 2 H), 4.32 (m, 2 H), 4.11 (d, J=14.2 Hz, 2 H), 3.5–3.6 (m, 2 H), 3.15–3.30 (m, 2 H), 1.55–1.80 (m, 6 H), 1.50 (s, 36 H), 0.85 (s, 18 H); MS (m/z) 573.7 (M+H)$^+$.

To a solution of 64 (138 mg, 0.241 mmol), 52 (105 mg, 0.253 mmol) and, HOBt (34.2 mg, 0.253 mmol) in DCM (5.0 ml) cooled to 0° C. was added DIPEA (0.088 ml, 0.506 mmol) and EDC (48.5 mg, 0.253 mmol). After addition the cooling bath was removed and the mixture stirred at room temperature for 18 hours. The reaction mixture was diluted with EtOAc (25 ml), washed with 1 N aqueous HCl, saturated aqueous NaHCO$_3$ and brine. Drying and evaporation gave a yellow foam which was purified by flash chromatography on silica gel (PE/EtOAc 3:1, Et$_3$N 0.1%). 115 mg (50%) of the coupling product were obtained. MS (m/z) 951.1 (M+H)$^+$.

Synthesis of 708a,b

The above compound (115 mg) was treated for 3 hours at room temp. with TFA/CH$_2$Cl$_2$/H$_2$O (65:35:5, 40 mL). After removal of the solvents the residue was freeze-dried from CH$_3$CN/H$_2$O 1:1 (50 mL) obtaining the TFA salt of crude 708 as a mixture of 2 diastereomers (95 mg, 94%).

Purification and separation of the isomers was achieved by preparative RP-HPLC: Gradient linear from 70% to 37% A over 17 min, then isocratic. The first fraction (RT=10.0 min) is diastereomer 708a. $^1$H-NMR (DMSO-d$_6$) δ, 7.96 (d, J=8.1 Hz, 1 H), 7.89 (t, J=6.2 Hz, 1 H), 7.66 (d, J=7.8 Hz, 1 H), 7.50 (d, J=5.2 Hz, 1 H), 7.46 (s, 1 H), 7.44 (s, 1 H), 6.98 (d, J=5.2 Hz, 1 H), 6.84 (m, 2 H), 6.48 (m, 2 H), 5.84 (t, J=57.3 Hz, 1 H), 4.27 (m, 1 H), 4.22 (m, 1 H), 3.67 (d, J=14.2 Hz, 1 H), 3.35–3.03 (m, 5 H), 2.78 (t, J=7 Hz, 2 H), 2.08 (m, 2 H), 1.44 (m, 3 H), 0.82 (m, 6 H). The second peak corresponds to 708b (RT=10.8 min), 38 mg after lyophilization. $^1$H-NMR (DMSO-d$_6$) δ, 8.02 (d, J=8.1 Hz, 1 H), 7.96 (t, J=6.2 Hz, 1 H), 7.72 (d, J=7.8 Hz, 1 H), 7.46 (s, 2 H), 7.45 (d, J=5.2 Hz, 1 H), 7.0 (d, J=5.2 Hz, 1 H), 6.82 (m, 2 H), 6.47 (m, 2 H), 5.91 (t, J=57.3 Hz, 1 H), 4.34 (m, 1 H), 4.25 (m, 1 H), 3.67 (d, J=14.2 Hz, 1 H), 3.4–3.15 (m, 3 H), 3.1 (s, 2 H), 2.8 (t, J=7 Hz, 2 H), 2.11 (m, 2 H), 1.41 (m, 3 H), 0.76 (m, 6 H). MS (m/z) 721.5 (M+H)$^+$.

Example 44

Synthesis of Compound 713

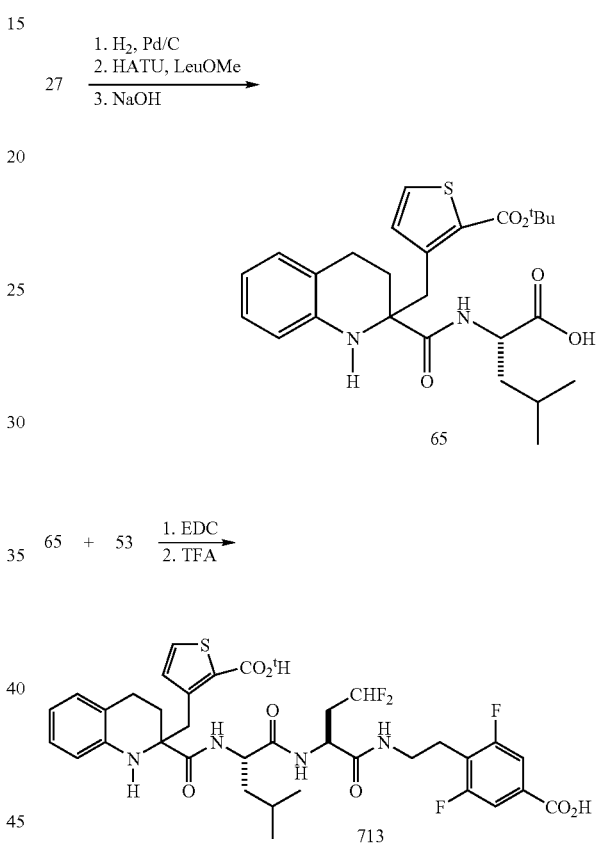

Synthesis of 65

A solution 27 (989 mg) in MeOH (60 mL) was treated with Pd/C (10%, 200 mg) and was stirred under an atmosphere of hydrogen for 15 h. The mixture was filtered and concentrated and the residue (600 mg) was taken up in DCM (3 mL) and then treated with L-leucine methylester (291.9 mg, 1.6 mmol) and DIPEA (0.84 mL, 4.8 mmol). The solution was cooled to 0° C. and HATU (611 mg, 1.61 mmol) was added. The mixture was stirred for 6 h and then diluted with hydrochloric acid (1 N) and extracted with EtOAc. The organic layer was washed with NaHCO$_3$ and brine and then dried over Na$_2$SO$_4$. Concentration afforded a residue which was purified by chromatography (biotage 40×70, 90:10 petroleum ether:ethyl acetate eluent) to give an oil (489 mg), a portion of which (450 mg) was taken up in MeOH (5 mL) and treated dropwise with a 1 N NaOH(aq) (1.1 mL). The mixture was stirred for 8 h at room temperature, then acidified and extracted with EtOAc. Concentration of the dried organic layer gave 65 as a mixture of diastereoisomers (1:1). ¹H NMR (DMSO-d₆) 7.73 (m, 1 H), 7.62 (app. t, J=5.10, 1 H), 7.14 and 7.07 (d, J=5.10 Hz, 1 H), 6.83 (m, 1 H), 6.75 (m, 1 H), 6.50 (d, J=7.97 Hz, 1 H), 6.40 (m, 1 H), 5.88 and 5.66 (s, 1 H), 4.21 (m, 1 H), 3.69–3.57 (m, 1 H), 3.22–3.13 (m, 1 H), 2.47–2.33 (m, 3 H), 2.27 (m, 1 H), 1.49 and 1.47 (s, 9 H), 1.42 (m, 2 H), 1.19 (m, 1 H), 0.81 (m, 3 H), 0.62 (m, 3 H).

Synthesis of 713

A solution of 65 (95 mg, 0.195 mmol) in DCM (5 mL) was treated with DIPEA (0.034 mL, 0.195 mmol), HOBt (26.4 mg, 0.195 mmol), and 53 (81 mg, 0.195 mmol). The solution was cooled to 0° C. and EDC (37.4 mg, 0.195 mmol) was added. After stirring for 15 h at room temperature, the mixture was diluted with hydrochloric acid and extracted with EtOAc. Concentration of the dried organic layer afforded a residue which was treated with a 60/10/30 mixture of TFA/H2O/DCM (10 mL) and stirred for 1 h at room temperature. The solution was concentrated and the solid was purified by HPLC (Column: Nucleosil C18 (Machery Nagel), 25×2.5 cm; 45% A isocratic) to give 713 as the second fraction.

First diastereomer: 14 mg (10%); ¹H NMR (DMSO-d₆) 8.14 (dd, J=5.8, 6.0 Hz, 1 H), 8.10 (d, J=8.2 Hz, 1 H), 7.66 (m, 2 H), 7.49 (m, 2 H), 7.11 (d, J=5.1 Hz, 1 H), 6.87 (m, 1 H), 6.76 (d, J=7.3 Hz, 1 H), 6.52 (d, J=7.9 Hz, 1 H), 6.42 (m, 1 H), 5.91 (bs 1 H), 5.84 (bt, J=56.5 Hz, 1 H), 4.25 (m, 2 H), 3.69 (d, J=13.3 Hz, 1 H), 3.20 (d, J=13.3 Hz, 1 H), 3.18 (m, 2 H), 2.80 (t, J=6.5 Hz, 2 H), 2.37 (m, 4 H), 2.00 (m, 2 H), 1.43 (m, 2 H), 1.11 (m, 1 H), 0.86 (d, J=6.8 Hz, 3 H), 0.82 (d, J=7.2 Hz, 3 H); MS (m/z) 735.4 (M+H)⁺.

713: 14 mg (10%); ¹H NMR (DMSO-d₆) 8.22 (t, J=8.2 Hz, 1 H), 8.19 (d, J=5.1 Hz, 1 H), 7.67 (d, J=7.9 Hz, 1 H), 7.61 (d, J=5.1 Hz, 1 H), 7.49 (m, 2 H), 7.10 (d, J=5.1 Hz, 1 H), 6.87 (m, 1 H), 6.78 (d, J=7.5 Hz, 1 H), 6.54 (d, J=7.8 Hz, 1 H), 6.44 (m, 1 H), 6.07 (bs, 1 H), 5.95 (bt, J=56.2 Hz, 1 H), 4.35 (m, 1 H), 4.23 (m, 1 H), 3.62 (d, J=13.4 Hz, 1 H), 3.25 (d, J=13.4 Hz, 1 H), 3.20 (m, 2 H), 2.81 (t, J=6.8 Hz, 2 H), 2.50–2.25 (m, 3 H), 2.18–2.01 (m, 2 H), 1.34 (m, 2 H), 1.16 (m, 2 H), 0.68 (d, J=6.6 Hz, 3 H), 0.65 (d, J=6.5 Hz, 3 H); MS (m/z) 735.6 (M+H)⁺.

Example 45

Synthesis of Compound 576

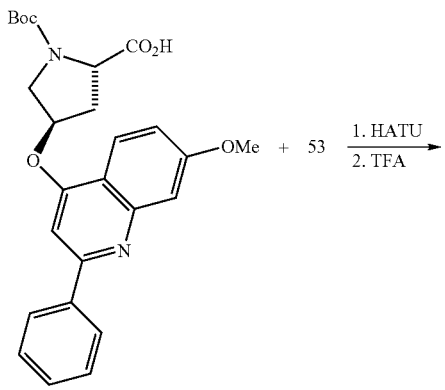

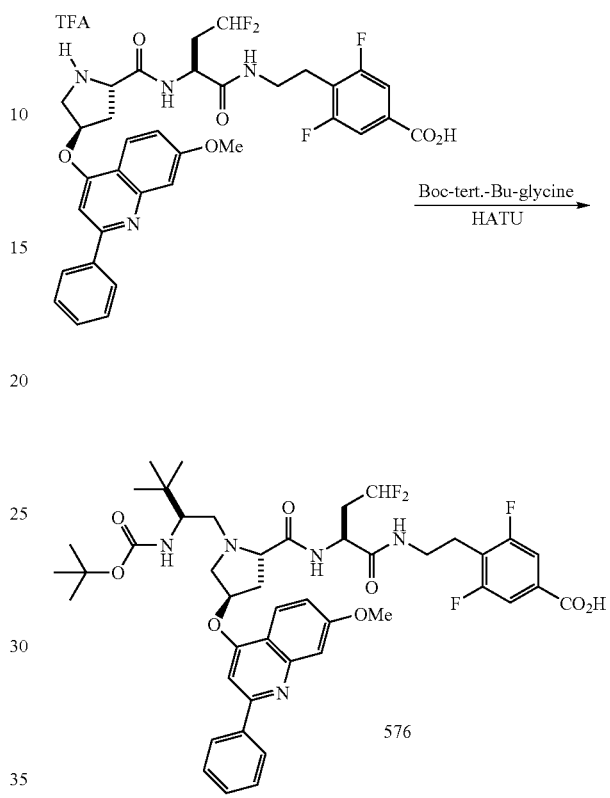

The title compound was prepared using the procedure described in Example 36 by coupling compound 53 with (4R)-1-(tert-butoxycarbonyl)-4-[(7-methoxy-2-phenylquinolin-4-yl)oxy-proline (prepared as described in WO 0009543, example 7). After coupling and work-up, the crude product was treated with TFA to remove the protecting groups, and then coupled to Boc-tert-butyl glycine to give the final product after purification by RP-HPLC.

¹H NMR (400 MHz, DMSO-d₆): δ 8.45 (d, J=8.4 Hz, 1 H); 8.25–8.15 (m, 4 H); 7.20–7.05 (m, 4 H); 7.05–7.45 (m, 3H); 7.25–7.15 (m, 1H); 6.78 (d, J=7.8 Hz, 1 H); 6.13 (app dt J=4.3, 56.0 Hz, 1 H), 5.77 (bs, 1 H); 4.60–4.50 (m, 2 H); 4.40–4.25 (m, 1H); 4.02 (d, J=8.0 Hz, 1 H); 3.96 (s, 3H); 3.89 (d, J=10.8 Hz, 1 H); (peaks overlapped by H₂O bs); 3.25–3.15 (m, 2 H); 2.30–1.95 (m, 3H); 1.22 (s, 9 H); 0.96 (s, 9 H). MS (m/z) 882+ (M+1)⁺.

Inhibition of NS3 Protease

Example 46

Full-Length NS3-NS4A Heterodimer Protein Assay (Assay A)

(Gallinari, P., Paolini, C., Brennan, D., Nardi, C., Steinkühler, C. and De Francesco, R. Modulation of hepatitis C virus NS3 protease and helicase activities through the interaction with NS4A. *Biochemistry* 38, 5620–5632, 1999)

In this assay the full length NS3 protein spanning residues 1027–1657 of the HCV polyprotein, noncovalently complexed with the full-length NS4A cofactor protein (residues 1658–1711) was used. Assays were performed in 60 µl of a buffer containing 50 mM Hepes pH 7.5, 0.15 M NaCl, 0.1% (v/v) Triton X-100, 15% (v/v) glycerol, 10 mM DTT, 2 nM NS3/NS4A complex. To this assay mix 10 µM (final concentration) of a peptide substrate corresponding to the NS5AB cleavage site and having the sequence of the NS5A-NS5B peptide, were added. Incubation times at 23° C. were adjusted to obtain <10% conversion. Reactions were stopped by the addition of 40 µl of 1% TFA. Cleavage was determined by HPLC using a Merck-Hitachi chromatograph equipped with an autosampler. 80 µl samples were injected on a Lichrospher C18 reversed phase cartridge column (4×74 mm, 5 µm, Merck) and fragments were separated using a 10–40% acetonitrile gradient at 5%/min using a flow rate of 2.5 ml/min. Peak detection was done by monitoring both the absorbance at 220 nm and tryptophan fluorescence ($\lambda_{ex}$=280 nm, $\lambda_{em}$=350 nm). Cleavage products were quantitated by integration of chromatograms with respect to appropriate standards. Kinetic parameters were calculated from nonlinear least-squares fit of initial rates as a function of substrate concentration with the help of a Kaleidagraph software, assuming Michaelis-Menten kinetics.

$K_i$ values of peptide inhibitors were calculated from substrate titration experiments performed in the presence of increasing amounts of inhibitor. Experimental data sets were simultaneously fitted to eq.1 using a multicurve fit macro with the help of a Sigmaplot software:

$$V=(V_{max}S)/(K_m(1+K_i/I)+S); \qquad (eq.1)$$

Alternatively, $K_i$ values were derived from IC50 values, calculated using a four-parameter logistic function, according to eq.2:

$$IC50=(1+S/K_m)K_i \qquad (eq.2)$$

Example 47

HCV NS3 Protease Domain/ NS4A Cofactor Peptide Assay (Assay B)

(Steinkühler, C., Biasiol, G., Brunetti, M., Urbani, A., Koch, U., Cortese, R., Pessi, A., and De Francesco, R. Product inhibition of the hepatitis C virus NS3 protease. *Biochemistry* 37, 8899–8905, 1998)

In this assay the NS3 protease domain (residues 1027–1206 of the HCV polyprotein) complexed to a modified form of the NS4A peptide, spanning residues 21–34 of the NS4A cofactor in addition to a solubilizing lys-tag, Pep 4AK were used. As substrate, peptide 4AB based on the sequence of the NS4A/NS4B cleavage site of the HCV polyprotein, was added.

Cleavage assays were performed in 60 µl 50 mM Hepes pH7.5, 1% (w/v) CHAPS, 15% (v/v) glycerol, 10 mM DTT (buffer A), containing 80 µM Pep4AK. Buffer solutions were preincubated for 10 min with 10–200 nM protease and reactions were started by addition of 10 µM substrate. Six duplicate data points at different substrate concentrations were used to calculate kinetic parameters. Incubation times were chosen in order to obtain <7% substrate conversion and reactions were stopped by addition of 40 µl 1% TFA. Reactions were analysed by HPLC essentially as described above. The fluorescence detector was set to monitor tyrosine fluorescence of substrate and cleavage product ($\lambda_{ex}$=260 nm, $\lambda_{em}$=305 nm).

Tables of Compounds

The following tables list compounds representative of the invention. All compounds were characterized by $^1$H-NMR and mass spectroscopy. Compounds of the invention were either assayed in one or both of the assays described in examples 46 and 47 and were found to be active with $IC_{50}$ below 100 µM (C) below 10 µM (B) or below 1 µM (A). A list of abbreviations used in the tables can be found at the beginning of the Examples.

TABLE 1

| No. | $R_5$ | $R_4$ | $R_2$ | $R_1$ | Assay A | Assay B |
|---|---|---|---|---|---|---|
| 101 | Cbz | $CO_2H$ (propyl chain) | —$CH_2$—SH | phenethyl | | C |
| 102 | $HO_2C$-benzyl-O-C(O)- | isopropyl | —$CH_2$—SH | phenethyl | | C |

TABLE 1-continued

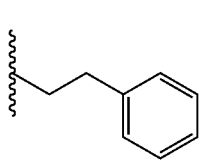

| No. | R₅ | R₄ | R₂ | R₁ | Assay A | Assay B |
|---|---|---|---|---|---|---|
| 103 | Boc | CO₂H (chain) | —CH₂—SH | phenethyl | | C |
| 104 | i-Boc | CO₂H (chain) | —CH₂—SH | phenethyl | C | C |
| 105 | Boc | CO₂H (chain) | —CH₂—CHF₂ | phenethyl | C | C |
| 106 | i-Boc | CO₂H (chain) | —CH₂—SH | a) 2-hydroxy-2-phenylethyl | | C |
| 107 | i-Boc | CO₂H (chain) | —CH₂—SH | a) 2-phenylpropyl (racemic) | | C |
| 108 | i-Boc | CO₂H (chain) | —CH₂—SH | 2-phenylpropyl | | C |
| 109 | i-Boc | CO₂H (chain) | —CH₂—SH | (1-phenylcyclopropyl)methyl | | C |
| 110 | i-Boc | CO₂H (chain) | —CH₂—SH | (1-phenylcyclobutyl)methyl | | C |

TABLE 1-continued

| No. | R₅ | R₄ | R₂ | R₁ | Assay A | Assay B |
|---|---|---|---|---|---|---|
| 111 | i-Boc | CO₂H (butyl) | —CH₂—SH | CH₂CO₂H, 4-Cl-phenyl | | C |
| 112 | i-Boc | CO₂H (butyl) | —CH₂—SH | ethyl-2-F-phenyl | | C |
| 113 | i-Boc | CO₂H (butyl) | —CH₂—SH | ethyl-2-Cl-phenyl | | C |
| 114 | Boc | CO₂H (butyl) | —CH₂—SH | ethyl-2-Cl-phenyl | C | B |
| 115 | Boc | CO₂H (butyl) | —CH₂—CHF₂ | ethyl-2-Cl-phenyl | C | B |
| 116 | Cbz | CO₂H (butyl) | —CH₂—SH | ethyl-2-Cl-phenyl | | C |
| 117 | i-Boc | CO₂H (butyl) | —CH₂—SH | ethyl-2-Br-phenyl | | C |
| 118 | i-Boc | CO₂H (butyl) | —CH₂—SH | ethyl-2-CH₃-phenyl | | C |

TABLE 1-continued

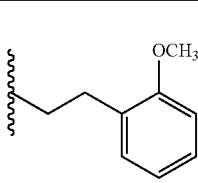

| No. | R₅ | R₄ | R₂ | R₁ | Assay A | Assay B |
|-----|------|------|------|------|------|------|
| 119 | i-Boc | CO₂H (butyl) | —CH₂—SH | 2-OCH₃-phenyl-propyl | | C |
| 120 | i-Boc | CO₂H (butyl) | —CH₂—SH | 2-OEt-phenyl-propyl | | C |
| 121 | i-Boc | CO₂H (butyl) | —CH₂—SH | 2-CF₃-phenyl-propyl | | C |
| 122 | i-Boc | CO₂H (butyl) | —CH₂—SH | 2-CO₂Me-phenyl-propyl | | C |
| 123 | i-Boc | CO₂H (butyl) | —CH₂—SH | 2-OPh-phenyl-propyl | | C |
| 124 | i-Boc | CO₂H (butyl) | —CH₂—SH | 2-OCH₂Ph-phenyl-propyl | | C |
| 125 | i-Boc | i-Pr | —CH₂—CHF₂ | 2-(CO₂H-ethyl)-phenyl-propyl | C | |
| 126 | i-Boc | CO₂H (butyl) | —CH₂—SH | 3-F-phenyl-propyl | | C |

TABLE 1-continued
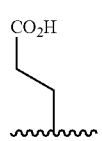
| No. | R5 | R4 | R2 | R1 | Assay A | Assay B |
|-----|------|------|------|------|---------|---------|
| 127 | i-Boc | CO2H 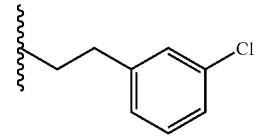 | —CH2—SH | 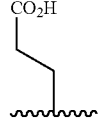 (3-Cl-phenyl) | | C |
| 128 | i-Boc | CO2H 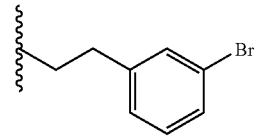 | —CH2—SH | 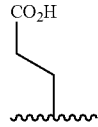 (3-Br-phenyl) | | C |
| 129 | i-Boc | CO2H 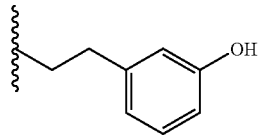 | —CH2—SH | 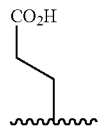 (3-OH-phenyl) | | C |
| 130 | i-Boc | CO2H 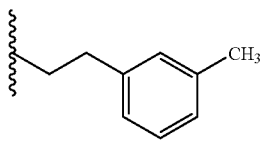 | —CH2—SH | 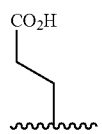 (3-CH3-phenyl) | | C |
| 131 | i-Boc | CO2H 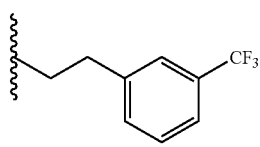 | —CH2—SH | 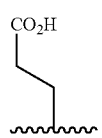 (3-CF3-phenyl) | | C |
| 132 | i-Boc | CO2H 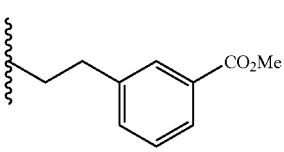 | —CH2—SH | 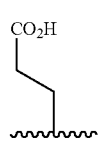 (3-CO2Me-phenyl) | | C |
| 133 | i-Boc | CO2H 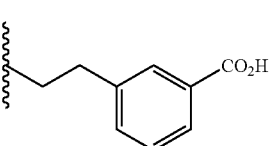 | —CH2—SH | 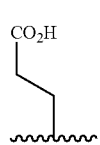 (3-CO2H-phenyl) | C | B |
| 134 | i-Boc | CO2H 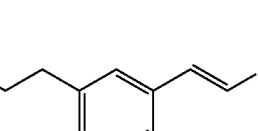 | —CH2—SH | (3-CH=CH-CO2H-phenyl) | B | B |

TABLE 1-continued

| No. | R₅ | R₄ | R₂ | R₁ | Assay A | Assay B |
|---|---|---|---|---|---|---|
| 135 | i-Boc | CO₂H | —CH₂—SH | (3-substituted phenyl propyl, substituent = CH=CH-CO₂Et) | C | C |
| 136 | i-Boc | CO₂H | —CH₂—SH | (3-Ph phenyl propyl) | | C |
| 137 | i-Boc | CO₂H | —CH₂—SH | (3-OPh phenyl propyl) | | C |
| 138 | i-Boc | CO₂H | —CH₂—SH | (4-Cl phenyl propyl) | | C |
| 139 | i-Boc | CO₂H | —CH₂—SH | (4-Br phenyl propyl) | | C |
| 140 | i-Boc | CO₂H | —CH₂—SH | (4-CH₃ phenyl propyl) | | C |
| 141 | i-Boc | CO₂H | —CH₂—SH | (4-OMe phenyl propyl) | | C |
| 142 | Boc | CO₂H | —CH₂—SH | (4-OMe phenyl propyl) | | C |

TABLE 1-continued

| No. | R5 | R4 | R2 | R1 | Assay A | Assay B |
|-----|-----|-----|-----|-----|---------|---------|
| 143 | Cbz | CO2H (butyl chain) | —CH2—SH | 4-methoxyphenylpropyl | | C |
| 144 | i-Boc | CO2H (butyl chain) | —CH2—SH | 4-ethoxyphenylpropyl | | C |
| 145 | i-Boc | CO2H (butyl chain) | —CH2—SH | 4-phenoxyphenylpropyl | | C |
| 146 | i-Boc | CO2H (butyl chain) | —CH2—SH | 4-hydroxyphenylpropyl | | C |
| 147 | i-Boc | CO2H (butyl chain) | —CH2—SH | 4-nitrophenylpropyl | | C |
| 148 | i-Boc | CO2H (butyl chain) | —CH2—SH | 4-t-Bu-phenylpropyl | | C |
| 149 | i-Boc | CO2H (butyl chain) | —CH2—SH | 4-CF3-phenylpropyl | | C |
| 150 | i-Boc | CO2H (butyl chain) | —CH2—SH | 4-CO2Me-phenylpropyl | | C |

TABLE 1-continued
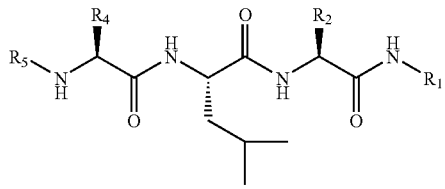
| No. | R5 | R4 | R2 | R1 | Assay A | Assay B |
|---|---|---|---|---|---|---|
| 151 | i-Boc | CO2H (propyl) | —CH2—SH | 4-(CH2CH2)-C6H4-CO2H | C | B |
| 152 | i-Boc | isopropyl | —CH2—SH | 4-(CH2CH2)-C6H4-CO2H | B | B |
| 153 | i-Boc | CO2H (propyl) | —CH2—SH | 4-(CH2CH2)-C6H4-CH2-CO2Me | | C |
| 154 | i-Boc | CO2H (propyl) | —CH2—SH | 4-(CH2CH2)-C6H4-CH2-CO2H | C | B |
| 155 | i-Boc | CO2H (propyl) | —CH2—SH | 4-(CH2CH2)-C6H4-CH2CH2-CO2Me | | C |
| 156 | i-Boc | CO2H (propyl) | —CH2—SH | 4-(CH2CH2)-C6H4-CH2CH2-CO2H | C | B |
| 157 | i-Boc | CO2H (propyl) | —CH2—SH | 4-(CH2CH2)-C6H4-CH=CH-CO2Et | B | B |
| 158 | i-Boc | CO2H (propyl) | —CH2—SH | 4-(CH2CH2)-C6H4-CH=CH-CO2H | B | B |

TABLE 1-continued

| No. | R₅ | R₄ | R₂ | R₁ | Assay A | Assay B |
|-----|-----|-----|-----|-----|---------|---------|
| 159 | i-Boc | CO₂H | —CH₂—SH | 4-(SO₂NH₂)phenyl-propyl | | B |
| 160 | i-Boc | CO₂H | —CH₂—SH | 4-(SO₂NHC(O)CH₃)phenyl-propyl | B | B |
| 161 | i-Boc | CO₂H | —CH₂—SH | 4-(SO₂NHC(O)CH(CH₃)₂)phenyl-propyl | | B |
| 162 | i-Boc | CO₂H | —CH₂—SH | 4-(SO₂NHC(O)Ph)phenyl-propyl | | B |
| 163 | i-Boc | CO₂H | —CH₂—SH | 4-(SO₂NHC(O)-(4-n-Bu-pyridin-2-yl))phenyl-propyl | | B |
| 164 | i-Boc | CO₂H | —CH₂—SH | 2,6-dichlorophenyl-propyl | C | B |
| 165 | i-Boc | CO₂H | —CH₂—SH | | B | B |

TABLE 1-continued

| No. | R5 | R4 | R2 | R1 | Assay A | Assay B |
|---|---|---|---|---|---|---|
| 166 | i-Boc | CO2H (chain) | —CH2—CHF2 | | C | B |
| 167 | Boc | CO2H (chain) | —CH2—SH | | | C |
| 168 | alloc | CO2H (chain) | —CH2—SH | | | C |
| 169 | Cbz | CO2H (chain) | —CH2—SH | | | C |
| 170 | MeO2C-C6H4-CH2-O-C(=O)- | CO2H (chain) | —CH2—SH | | | C |
| 171 | HO2C-C6H4-CH2-O-C(=O)- | CO2H (chain) | —CH2—SH | | | C B |
| 172 | i-Boc | CO2H (chain) | —CH2—SH | 3,4-dichlorophenethyl | | C |
| 173 | i-Boc | CO2H (chain) | —CH2—SH | 5-bromo-2-methoxyphenethyl | | C B |
| 174 | i-Boc | CO2H (chain) | —CH2—SH | 2,5-dimethoxyphenethyl | | C |

TABLE 1-continued

| No. | R₅ | R₄ | R₂ | R₁ | Assay A | Assay B |
|-----|-----|-----|-----|-----|---------|---------|
| 175 | i-Boc | (CH₂)₃-CO₂H | —CH₂—SH | 4-(2-methoxy-4-hydroxyphenyl)propyl (3-OMe, 4-OH) | | C |
| 176 | i-Boc | (CH₂)₃-CO₂H | —CH₂—SH | 3-Br-4-OMe-phenylpropyl | | C |
| 177 | i-Boc | (CH₂)₃-CO₂H | —CH₂—SH | 3-Cl-4-CO₂Me-phenylpropyl | C | B |
| 178 | i-Boc | (CH₂)₃-CO₂H | —CH₂—SH | 3-Cl-4-CO₂H-phenylpropyl | B | A |
| 179 | i-Boc | i-Pr | —CH₂—CHF₂ | 3-Cl-4-CO₂H-phenylpropyl | B | B |
| 180 | i-Boc | (CH₂)₃-CO₂H | —CH2—CHF2 | 3-Cl-4-CO₂H-phenylpropyl | B | A |
| 181 | cyclopentylmethyl-O-C(O)- | i-Pr | —CH₂—SH | 3-Cl-4-CO₂H-phenylpropyl | B | B |
| 182 | (1,1-dioxo-tetrahydro-2H-thiopyran-4-yl)-O-C(O)- | i-Pr | —CH₂—SH | 3-Cl-4-CO₂H-phenylpropyl | | C |

TABLE 1-continued

| No. | R₅ | R₄ | R₂ | R₁ | Assay A | Assay B |
|-----|-----|-----|-----|-----|---------|---------|
| 183 | (tetrahydrofuran-3-ylmethyl ester) | isopropyl | —CH₂—SH | 3-chloro-4-(propyl)benzoic acid | | B |
| 184 | (isopentyl ester) | isopropyl | —CH₂—SH | 3-chloro-4-(propyl)benzoic acid | | B |
| 185 | i-Boc | CO₂H (propyl) | —CH₂—SH | 3-fluoro-4-(propyl)benzoic acid methyl ester | | C |
| 186 | i-Boc | CO₂H (propyl) | —CH₂—SH | 3-fluoro-4-(propyl)benzoic acid | | A |
| 187 | i-Boc | CO₂H (propyl) | —CH₂—CHF₂ | 3,5-difluoro-4-(propyl)benzoic acid | A | A |
| 188 | i-Boc | CO₂H (propyl) | —CH₂—SH | 1-(carboxymethyl)indol-3-yl propyl | | B |
| 189 | i-Boc | CO₂H (propyl) | —CH₂—SH | indol-3-yl propyl | | C |
| 190 | i-Boc | CO₂H (propyl) | —CH₂—SH | thiophen-3-yl propyl | | B |

TABLE 1-continued
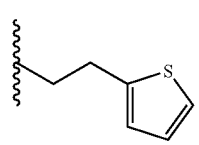
| No. | $R_5$ | $R_4$ | $R_2$ | $R_1$ | Assay A | Assay B |
|---|---|---|---|---|---|---|
| 191 | i-Boc | $CO_2H$ 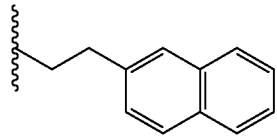 | —$CH_2$—SH | 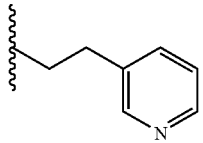 | | C |
| 192 | i-Boc | $CO_2H$ | —$CH_2$—SH | 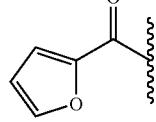 | | C |
| 193 | i-Boc | $CO_2H$ | —$CH_2$—SH | 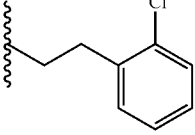 | | C |
a) 1:1 mixture of diastereomers
TABLE 2
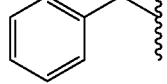
| No. | $R_5$ | $R_1$ | Assay A | Assay B |
|---|---|---|---|---|
| 201 | 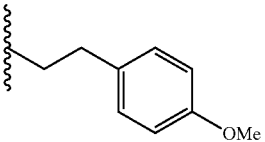 | | | C |
| 202 | | | | C |

TABLE 2-continued

| No. | R₅ | R₁ | Assay A | Assay B |
|-----|----|----|---------|---------|
| 203 | benzo[1,3]dioxol-5-yl-carbonyl | 2-chlorophenethyl | C | C |
| 204 | benzo[1,3]dioxol-5-yl-carbonyl | 4-methoxyphenethyl | | C |
| 205 | 3,4-dimethoxybenzoyl | 2-chlorophenethyl | | C |
| 206 | 3-bromobenzoyl | 2-chlorophenethyl | | C |
| 207 | 4-cyanobenzoyl | 4-methoxyphenethyl | | C |
| 208 | 2-amino-5-hydroxybenzoyl | 2-chlorophenethyl | | C |
| 209 | 3-aminopyridin-4-yl-carbonyl | 2-chlorophenethyl | | C |

TABLE 2-continued
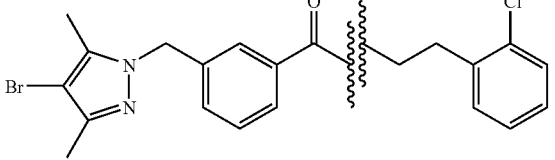
| No. | R₅ | R₁ | Assay A | Assay B |
|---|---|---|---|---|
| 210 | 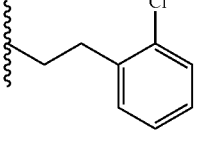 | 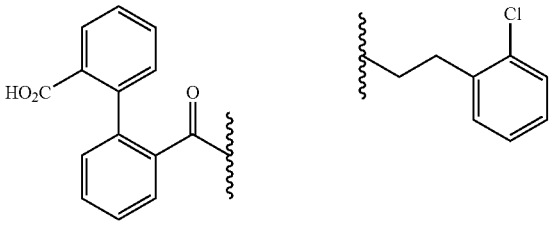 | | C |
| 211 | 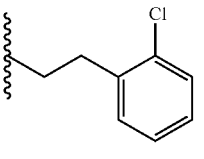 | 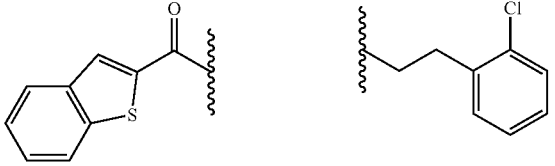 | | C |
| 212 | 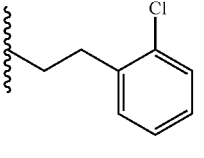 | 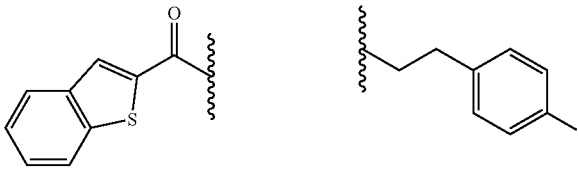 | | C |
| 213 | 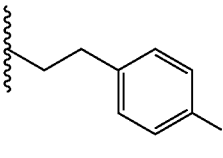 |  | | C |
| 214 | 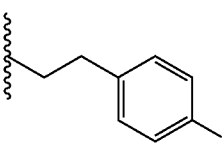 |  | | C |
| 215 | 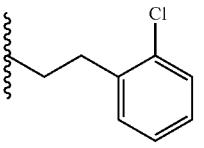 |  | | C |
| 216 | 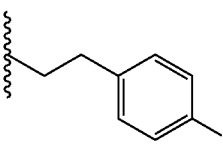 | | | C |

TABLE 2-continued

| No. | R₅ | R₁ | Assay A | Assay B |
|-----|----|----|---------|---------|
| 217 | phenyl-CH₂CH₂-C(=O)- | 2,4-dichlorophenethyl |  | C |
| 218 | 4-O₂N-phenyl-CH=CH-C(=O)- | 2-chlorophenethyl |  | C |
| 219 | 2-phenylcyclopropyl-C(=O)- (R/S, R/S) | 2-chlorophenethyl |  | C |
| 220 | 2-phenylcyclopropyl-C(=O)- (R/S, R/S) | 4-methoxyphenethyl |  | C |
| 221 | phenyl-CH(OH)-C(=O)- | 2-chlorophenethyl |  | B |
| 222 | thiophen-3-yl-CH₂-C(=O)- | 2-chlorophenethyl |  | C |
| 223 | thiophen-2-yl-CH₂-C(=O)- | 4-methoxyphenethyl |  | C |
| 224 | thiophen-2-yl-C(=O)-C(=O)- | 2-chlorophenethyl |  | C |

TABLE 2-continued
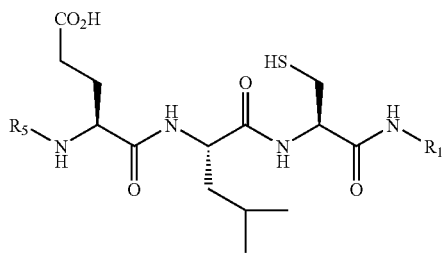
| No. | R₅ | R₁ | Assay A | Assay B |
|---|---|---|---|---|
| 225 | 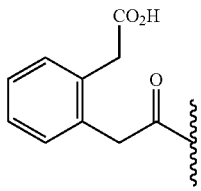 | 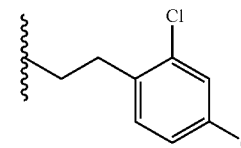 | | B |
| 226 | 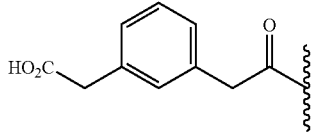 | 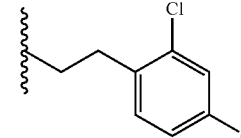 | | C |
| 227 | 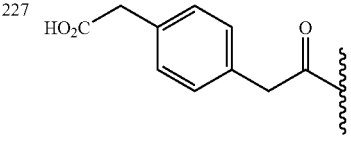 | 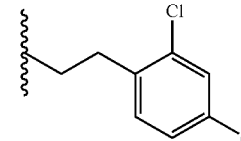 | | C |
| 228 | 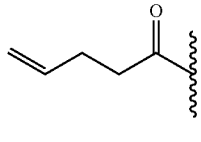 | 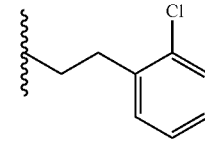 | | C |
| 229 a) | 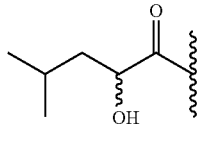 | 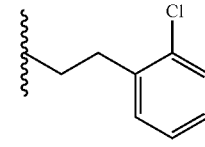 | | C |
| 230 | 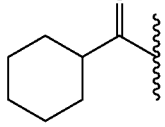 | 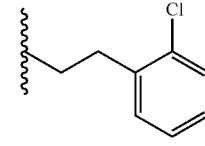 | | C |
| 231 | 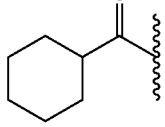 | 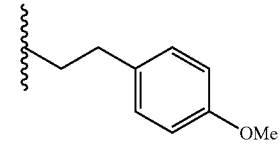 | | C |

TABLE 2-continued
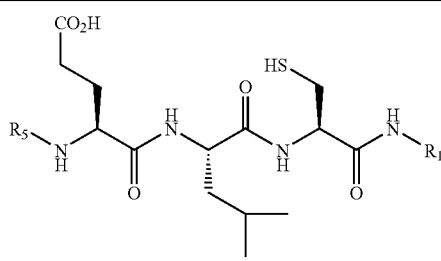
| No. | R₅ | R₁ | Assay A | Assay B |
|---|---|---|---|---|
| 232 | 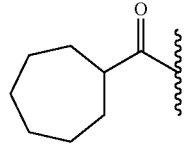 | 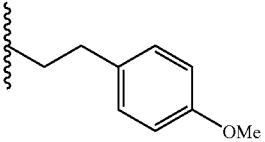 | | C |
| 233 | 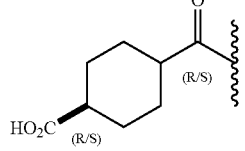 | 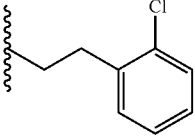 | | C |
| 234 | 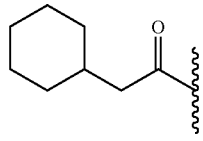 | 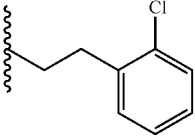 | | C |
| 235 | 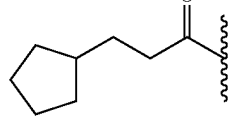 | 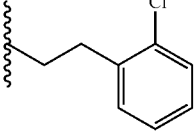 | | C |
| 236 | 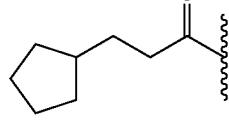 | 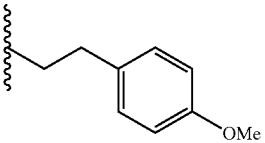 | | C |
| 237 | 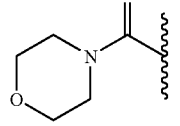 | 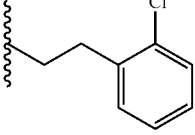 | | C |
| 238 | 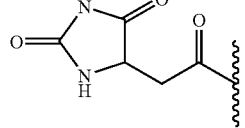 | 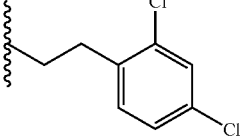 | | C |
| 239 | 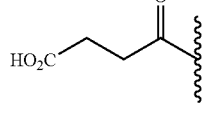 | 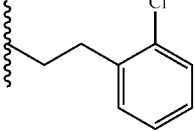 | | C |

TABLE 2-continued

| No. | R₅ | R₁ | Assay A | Assay B |
|-----|----|----|---------|---------|
| 240 | HO₂C-CH₂-C(CH₃)₂-CH₂-C(=O)- | -CH₂CH₂-(2-Cl-C₆H₄) | | C |
| 241 | HO₂C-CH₂-C(CH₃)₂-CH₂-C(=O)- | -CH₂CH₂-(4-OMe-C₆H₄) | | C |
| 242 b) | HO₂C-CH₂CH₂-C(CH₃)₂-C(=O)- and HO₂C-C(CH₃)₂-CH₂CH₂-C(=O)- | -CH₂CH₂-(2-Cl-C₆H₄) | | B |
| 243 | HO₂C-CH₂CH₂-C(CH₃)₂-C(=O)- | -CH₂CH₂-(4-OMe-C₆H₄) | | C |
| 244 | HO₂C-CH₂CH₂CH₂-C(=O)- | -CH₂CH₂-(2-Cl-C₆H₄) | | C |
| 245 a) | HO₂C-CH₂-CH(Me)-CH₂-C(=O)- | -CH₂CH₂-(2-Cl-C₆H₄) | | C |
| 246 | CH₂=CH-CH₂-NH-C(=O)- | -CH₂CH₂-(2-Cl-C₆H₄) | | C |

TABLE 2-continued

| No. | R₅ | R₁ | Assay A | Assay B |
|---|---|---|---|---|
| 247 | phenyl-NH-C(O)- | 2-Cl-phenyl-(CH₂)₂- | | C |
| 248 | benzyl-NH-C(O)- | 2,4-diCl-phenyl-(CH₂)₂- | | C |
| 249 | phenyl-SO₂- | 2-Cl-phenyl-(CH₂)₂- | | C |
| 250 | phenyl-SO₂- | 4-OMe-phenyl-(CH₂)₂- | | C |
| 251 | 4-methylphenyl-SO₂- | 2-Cl-phenyl-(CH₂)₂- | | C |
| 252 | naphth-1-yl-SO₂- | 2-Cl-phenyl-(CH₂)₂- | B | B |
| 253 | thien-2-yl-SO₂- | 2-Cl-phenyl-(CH₂)₂- | | C |
| 254 | methyl-SO₂- | 4-OMe-phenyl-(CH₂)₂- | | C |

TABLE 2-continued

[Structure: tripeptide with CO2H (Glu) side chain, leucine middle, HS-cysteine, with R5-NH on left and NH-R1 on right]

| No. | R₅ | R₁ | Assay A | Assay B |
|---|---|---|---|---|
| 255 | 2-naphthylsulfonyl | -CH₂CH₂-C₆H₄-OMe (para) | | C |
| 256 | benzylsulfonyl | -CH₂CH₂-(2,4-dichlorophenyl) | | C | a) 1:1 mixture of diastereomers; b) nearly 1:1 mixture of regioisomers

TABLE 3

[Structure: tripeptide with CO2H (Glu) side chain, cyclohexylmethyl middle residue, R2 on third residue, R5-NH on left and NH-R1 on right]

| No. | R₅ | R₂ | R₁ | Assay A | Assay B |
|---|---|---|---|---|---|
| 301 | AcDif | —CH₂—CHF₂ | -CH₂-O-CH₂-C₆H₅ | | C |
| 302 | AcDif | —CH₂—SH | -CH₂CH₂-C₆H₅ | | C |
| 303 | AcAspGluDif | —CH₂—SH | -CH₂CH₂-C₆H₅ | | A |

TABLE 3-continued

| No. | R₅ | R₂ | R₁ | Assay A | Assay B |
|-----|-----|-----|-----|---------|---------|
| 304 | AcAspGluDif | —CH₂—CHF₂ | (3-phenylpropyl) | | A |
| 305 | AcAspGluDif | —CH₂—CHF₂ | (benzyloxymethyl) | | A |
| 306 | AcAspGluDif | —CH₂—SH | (2-chlorophenyl)propyl | | A |
| 307 | AcAspGluDif | —CH₂—SH | (2-methoxyphenyl)propyl | | A |
| 308 | AcAspGluDif | —CH₂—SH | (3-chlorophenyl)propyl | | A |
| 309 | AcAspGluDif | —CH₂—SH | (3-methoxyphenyl)propyl | | A |
| 310 | AcAspGluDif | —CH₂—SH | (4-chlorophenyl)propyl | | A |
| 311 | AcAspGluDif | —CH₂—SH | (4-methoxyphenyl)propyl | | A |

TABLE 3-continued

| No. | R₅ | R₂ | R₁ | Assay A | Assay B |
|---|---|---|---|---|---|
| 312 | AcAspGluDif | —CH₂—SH | (3-(4-sulfamoylphenyl)propyl) | | A |
| 313 | AcAspGluDif | —CH₂—SH | (3-(4-nitrophenyl)propyl) | | A |
| 314 | AcAspGluDif | —CH₂—SH | (3-(4-methylphenyl)propyl) | | A |
| 315 | AcAspGluDif | —CH₂—SH | (3-(2,5-dimethoxyphenyl)propyl) | | A |
| 316 | AcAspGluDif | —CH₂—SH | (3-(3,4-dimethoxyphenyl)propyl) | | A |
| 317 | AcAspGluDif | —CH₂—SH | (3,3-diphenylpropyl) | | A |
| 318 | AcAspGluDif | —CH₂—SH | a) (2-phenylpropyl) | | A |

TABLE 3-continued
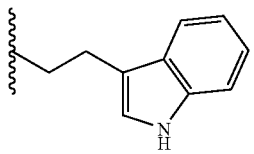
| No. | $R_5$ | $R_2$ | $R_1$ | Assay A | Assay B |
|---|---|---|---|---|---|
| 319 | AcAspGluDif | —$CH_2$—SH | 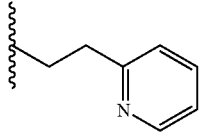 | | A |
| 320 | AcAspGluDif | —$CH_2$—SH | 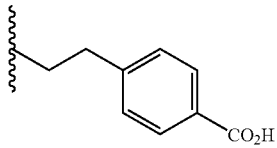 | | A |
| 321 | AcAspGluDif | —$CH_2$—$CHF_2$ | 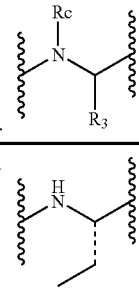 | A | A |
a) 1:1 mixture of diastereomers;
TABLE 4
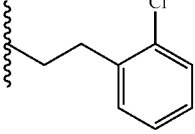
| No. | $\begin{array}{c}Rc\\ N\\ R_3\end{array}$ | $R_2$ | $R_1$ | Assay A | Assay B |
|---|---|---|---|---|---|
| 401 | 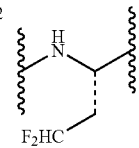 | —$CH_2$—SH | 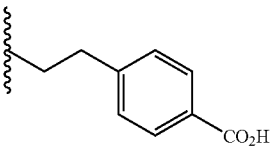 | | C |
| 402 | (structure with $F_2HC$) | —$CH_2$—SH | (4-CO2H phenyl) | | C |

TABLE 4-continued

| No. | N(Rc)(R3) group | R2 | R1 | Assay A | Assay B |
|---|---|---|---|---|---|
| 403 a) | NH, CH2CF3 substituent | —CH2—SH | 4-(CO2H)-phenethyl | | C |
| 404 | NH, CH2-(thiophen-2-yl) substituent | —CH2—SH | 2-Cl-phenethyl | | C |
| 405 | NH, n-propyl substituent | —CH2—SH | 2-Cl-phenethyl | | C |
| 406 | NH, CH2-(naphthalen-1-yl) substituent | —CH2—SH | 2-Cl-phenethyl | | C |
| 407 | NH, n-propyl substituent | —CH2—SH | 2-Cl-phenethyl | | C |

TABLE 4-continued

| No. | Rc, R3 | R2 | R1 | Assay A | Assay B |
|---|---|---|---|---|---|
| 408 | NH, cyclopropylmethyl | —CH2—SH | 2-Cl-phenylpropyl | C | C |
| 409 | NH, cyclohexylmethyl | —CH2—SH | 4-(CO2H)-phenylpropyl | | B |
| 410 a) | NH, phenyl | —CH2—SH | 2-Cl-phenylpropyl | | C |
| 411 | NH, cyclopentyl | —CH2—SH | 2-Cl-phenylpropyl | | C |
| 412 | NH, CH2CH2CO2H | —CH2—SH | 2-Cl-phenylpropyl | | C |
| 413 | NH, CH2CH2CO2Bn | —CH2—SH | 2-Cl-phenylpropyl | | C |

TABLE 4-continued
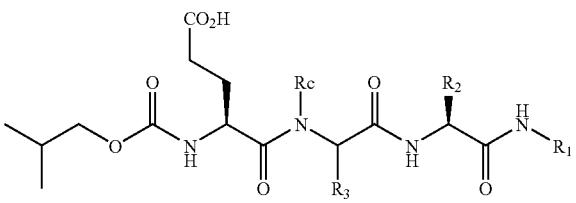
| No. | 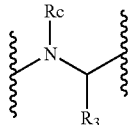 | R₂ | R₁ | Assay A | Assay B |
|---|---|---|---|---|---|
| 414 |  | —CH₂—SH | 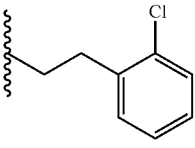 | | C |
| 415 | 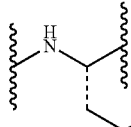 | —CH₂—SH | 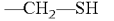 | | C |
| 416 | 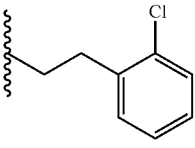 | —CH₂—SH | 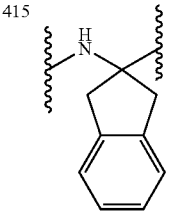 | | C |
| 417 | 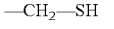 | —CH₂—SH | 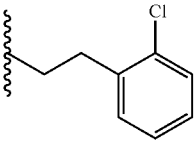 | | C |
| 418 | 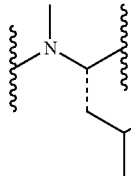 | —CH₂—SH | 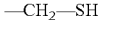 | | C |
| 419 | 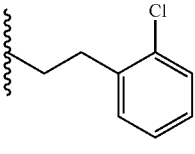 | —CH₂—SH | 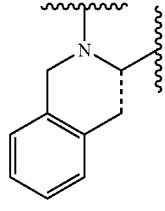 | | C |

TABLE 4-continued

| No. | | R₂ | R₁ | Assay A | Assay B |
|---|---|---|---|---|---|
| 420 | octahydroindole | —CH₂—SH | 2-chlorophenethyl | | B |
| 421 | indoline | —CH₂—CHF₂ | 3-chloro-4-(propyl)benzoic acid | | C |
| 422 | 5-phenylpyrrolidine | —CH₂—SH | 2-chlorophenethyl | | C | a) 1:1 mixture of diastereomers;

TABLE 5

| No. | R₅—NH—CH(R₄)—C(O)— | R₂₀ | R₂ | R₁ | Assay A |
|---|---|---|---|---|---|
| 501 | iBuO-C(O)-NH-CH(CH₂CH₂CO₂H)-C(O)- | H | —CH₂—SH | 2-chlorophenyl | C |

TABLE 5-continued

| No. | [R5-NH-CHR4-C(O)- group] | R20 | R2 | R1 | Assay A |
|---|---|---|---|---|---|
| 502 | isobutyl-O-C(O)-NH-CH(iPr)-C(O)- | H | —CH2—CHF2 | 3,5-difluoro-4-yl benzoic acid | B |
| 503 | isobutyl-O-C(O)-NH-CH(CH2CH2CO2H)-C(O)- | OH | —CH2—SH | 2-chlorophenyl | C |
| 504 | isobutyl-O-C(O)-NH-CH(iPr)-C(O)- | OH | —CH2—CHF2 | 3,5-difluoro-4-yl benzoic acid | B |
| 505 | isobutyl-O-C(O)-NH-CH(iPr)-C(O)- | OCH2O—(CH2)2OCH3 | —CH2—CHF2 | 3,5-difluoro-4-yl benzoic acid | B |
| 506 | isobutyl-O-C(O)-NH-CH(CH2CH2CO2H)-C(O)- | Ph | —CH2—SH | 2-chlorophenyl | B |
| 507 | isobutyl-O-C(O)-NH-CH(CH2CH2CO2H)-C(O)- | OCH2Ph | —CH2—SH | 2-chlorophenyl | B |

TABLE 5-continued

| No. | ![R5-NH-CHR4-C(O)-] | R20 | R2 | R1 | Assay A |
|---|---|---|---|---|---|
| 508 | iBuO-C(O)-NH-CH(CH2CH2CO2H)-C(O)- | CO2H | Ph | —CH2—SH | 2-Br-Ph | C |
| 509 | iBuO-C(O)-NH-CH(iPr)-C(O)- | —O-CH2-(4-CO2H-Ph) | Ph | —CH2—CHF2 | 2,6-Cl2-Ph | C |
| 510 | iBuO-C(O)-NH-CH(CH2CH2CO2H)-C(O)- | CO2H | Ph | —CH2—CHF2 | 2-Ph-Ph (biphenyl) | B |
| 511 | iBuO-C(O)-NH-CH(CH2CH2CO2H)-C(O)- | CO2H | Ph | —CH2—CHF2 | cyclohexenyl | C |
| 512 | iBuO-C(O)-NH-CH(CH2CH2CO2H)-C(O)- | CO2H | Ph | —CH2—SH | 4-CO2H-Ph | C |

TABLE 5-continued

| No. | R5-NH-CHR4-C(O)- group | R20 | R2 | R1 | Assay A |
|-----|------------------------|-----|-----|-----|---------|
| 513 | 1-Naphthylsulfonyl-NH-CH(CH2CH2CO2H)-C(O)- | Ph | —CH2—SH | 4-(CO2H)-C6H4— | C |
| 514 | 1-Naphthylsulfonyl-NH-CH(CH2CH2CO2H)-C(O)- | Ph | —CH2—SH | 4-(CO2Me)-C6H4— | C |
| 515 | Ph-CH(OH)-C(O)-NH-CH(CH2CH2CO2H)-C(O)- | Ph | —CH2—SH | 4-(CO2H)-C6H4— | C |
| 516 | iBuO-C(O)-NH-CH(iPr)-C(O)- | Ph | —CH2—SH | 4-(CO2H)-C6H4— | B |
| 517 | iBuO-C(O)-NH-CH(iPr)-C(O)- | Ph | —CH2—CHF2 | 4-(CO2H)-C6H4— | B |
| 518 | iBuO-C(O)-NH-CH(iPr)-C(O)- | Ph | —CH2—CHF2 | 4-(2H-tetrazol-5-yl)-C6H4— | B |

TABLE 5-continued
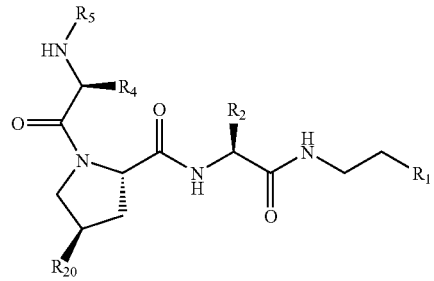
| No. | 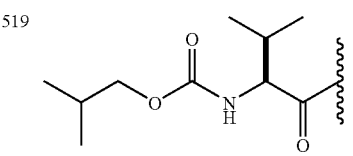 | $R_{20}$ | $R_2$ | $R_1$ | Assay A |
|---|---|---|---|---|---|
| 519 | 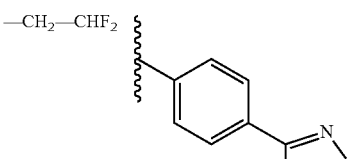 | Ph | —CH$_2$—CHF$_2$ | 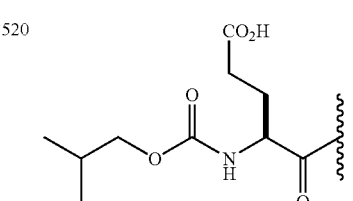 | C |
| 520 | 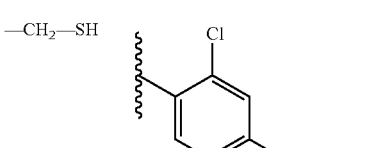 | Ph | —CH$_2$—SH | 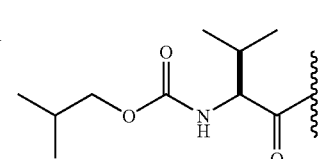 | B |
| 521 | 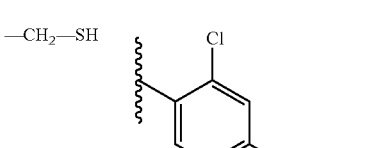 | Ph | —CH$_2$—SH | 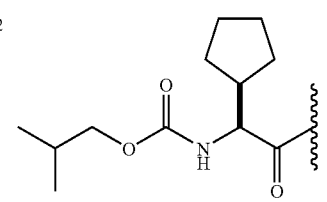 | A |
| 522 | 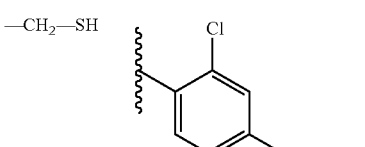 | Ph | —CH$_2$—SH | 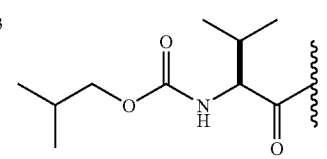 | A |
| 523 | 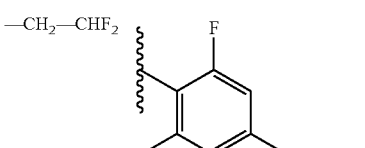 | Ph | —CH$_2$—CHF$_2$ | 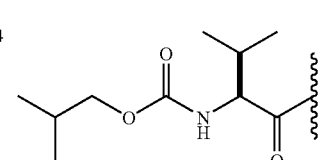 | A |
| 524 | 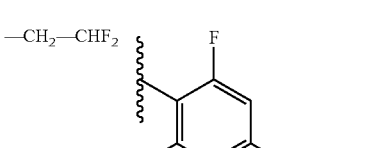 | Ph | —CH$_2$—CHF$_2$ | CO$_2$i-Pr | C |

TABLE 5-continued

| No. | R₂₀ | R₂ | R₁ | Assay A |
|---|---|---|---|---|
| 525 | Ph | —CH₂—CH₃ | 3,5-difluoro-4-CO₂H-phenyl | C |
| 526 | (R)-O-benzyl | —CH₂—CHF₂ | 3,5-difluoro-4-CO₂H-phenyl | A |
| 527 | (S)-O-benzyl | —CH₂—CHF₂ | 3,5-difluoro-4-CO₂H-phenyl | B |
| 528 | cyclohexyl | —CH₂—CHF₂ | 3,5-difluoro-4-CO₂H-phenyl | A |
| 529 | cyclohexyl | CH₂—CF₃ | 3,5-difluoro-4-CO₂H-phenyl | B |

All entries share R₅-NH-CH(R₄)-C(O)- group = isobutoxycarbonyl-Val-

TABLE 5-continued

| No. | R₅-NH-CHR₄-C(O)- group | R₂₀ | R₂ | R₁ | Assay A |
|---|---|---|---|---|---|
| 530 | isobutyl-O-C(O)-NH-CH(iPr)-C(O)- | -O-CH₂-Ph | CH₂—CF₃ | 3,5-difluoro-4-yl benzoic acid | B |
| 531 | isobutyl-O-C(O)-NH-CH(iPr)-C(O)- | cyclohexyl | —CH₂—CHF₂ | 3,5-difluoro-4-yl benzoic acid | B |
| 532 | isobutyl-O-C(O)-NH-CH(iPr)-C(O)- | cyclohexyl | —CH₂—CHF₂ | 3-chloro-4-yl benzoic acid | A |
| 533 | isobutyl-O-C(O)-NH-CH(sec-Bu)-C(O)- | cyclohexyl | —CH₂—CHF₂ | 3,5-difluoro-4-yl benzoic acid | A |
| 534 | isobutyl-O-C(O)-NH-CH(sec-Bu)-C(O)- | Ph | —CH₂—CHF₂ | 3,5-difluoro-4-yl benzoic acid | B |
| 535 | isobutyl-O-C(O)-NH-CH(sec-Bu)-C(O)- | cyclohexyl | —CH₂—CHF₂ | 3,5-difluoro-4-yl benzoic acid | A |

TABLE 5-continued

| No. | R5-NH-CHR4-C(O)- | R20 | R2 | R1 | Assay A |
|---|---|---|---|---|---|
| 536 | isobutyl-O-C(O)-NH-CH(tBu)-C(O)- | cyclohexyl | —CH2—CHF2 | 3,5-difluoro-4-(CO2H-phenyl) | B |
| 537 | isobutyl-O-C(O)-NH-CH(tBu)-C(O)- | Ph | —CH2—CHF2 | 3,5-difluoro-4-(CO2H-phenyl) | B |
| 538 | isobutyl-O-C(O)-NH-CH(cyclopentyl)-C(O)- | cyclohexyl | —CH2—CHF2 | 3,5-difluoro-4-(CO2H-phenyl) | A |
| 539 | neopentyl-O-C(O)-NH-CH(iPr)-C(O)- | cyclohexyl | —CH2—CHF2 | 3,5-difluoro-4-(CO2H-phenyl) | A |
| 540 | cyclopropylmethyl-O-C(O)-NH-CH(iPr)-C(O)- | cyclohexyl | —CH2—CHF2 | 3,5-difluoro-4-(CO2H-phenyl) | A |
| 541 | cyclopentyl-O-C(O)-NH-CH(iPr)-C(O)- | cyclohexyl | —CH2—CHF2 | 3,5-difluoro-4-(CO2H-phenyl) | A |

TABLE 5-continued
| No. | 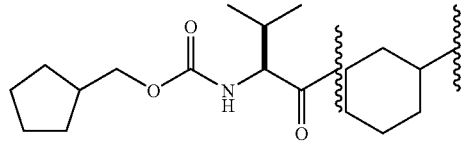 | $R_{20}$ | $R_2$ | $R_1$ | Assay A |
|---|---|---|---|---|---|
| 542 | 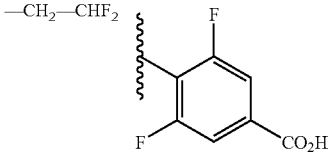 | 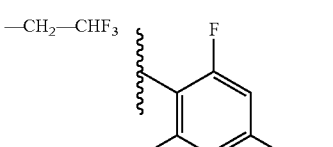 | —CH$_2$—CHF$_2$ | 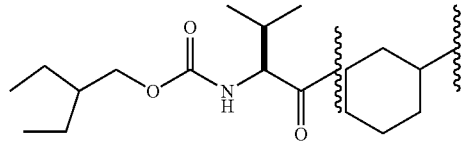 | B |
| 543 | 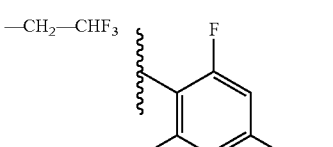 | 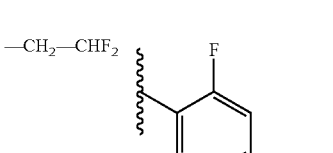 | —CH$_2$—CHF$_3$ | 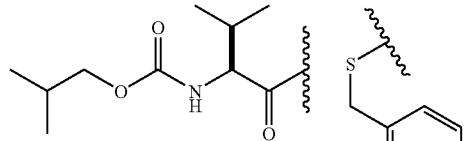 | B |
| 544 | 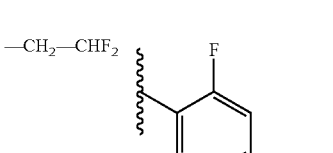 | 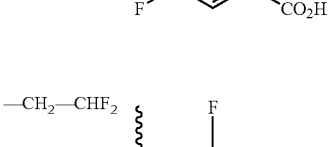 | —CH$_2$—CHF$_2$ | 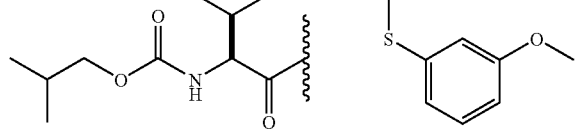 | B |
| 545 | 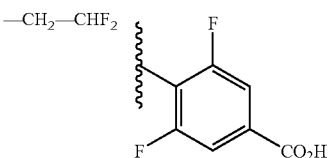 | 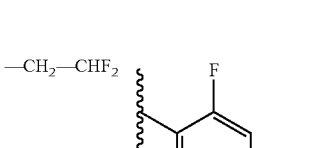 | —CH$_2$—CHF$_2$ | 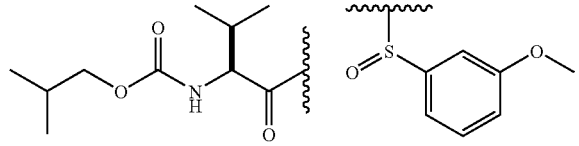 | A |
| 546 a) | 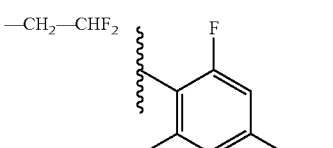 | 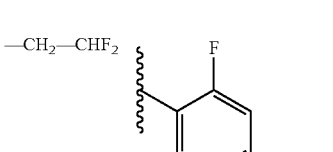 | —CH$_2$—CHF$_2$ | 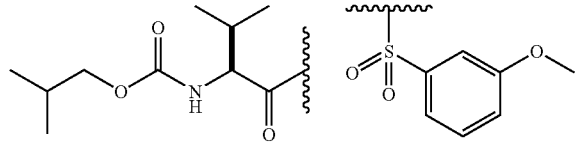 | B |
| 547 | 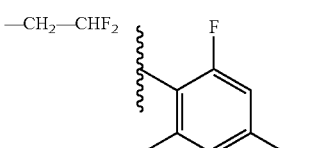 | 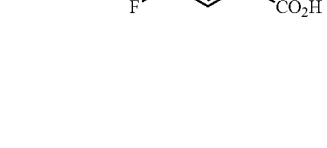 | —CH$_2$—CHF$_2$ | 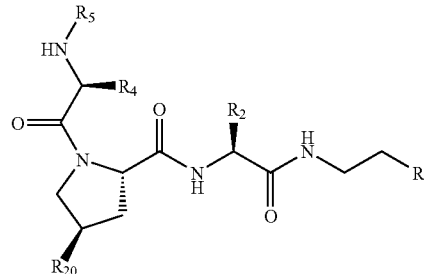 | A |

TABLE 5-continued

| No. | R5-NH-CHR4-C(O)- | R20 | R2 | R1 | Assay A |
|---|---|---|---|---|---|
| 548 | isobutyl-O-C(O)-NH-CH(iPr)-C(O)- | n-PrS | —CH₂—CHF₂ | 3,5-difluoro-4-yl benzoic acid | A |
| 549 | isobutyl-O-C(O)-NH-CH(iPr)-C(O)- | n-PrS(O) | —CH₂—CHF₂ | 3,5-difluoro-4-yl benzoic acid | B |
| 550 | isobutyl-O-C(O)-NH-CH(iPr)-C(O)- | n-PrS(O)₂ | —CH₂—CHF₂ | 3,5-difluoro-4-yl benzoic acid | A |
| 551 | isobutyl-O-C(O)-NH-CH(iPr)-C(O)- | cyclohexyl-S- | —CH₂—CHF₂ | 3,5-difluoro-4-yl benzoic acid | B |
| 552 | isobutyl-O-C(O)-NH-CH(iPr)-C(O)- | cyclohexyl-S(O)- a) | —CH₂—CHF₂ | 3,5-difluoro-4-yl benzoic acid | A |
| 553 | isobutyl-O-C(O)-NH-CH(iPr)-C(O)- | cyclohexyl-S(O)₂- | —CH₂—CHF₂ | 3,5-difluoro-4-yl benzoic acid | A |

TABLE 5-continued

| No. | R5-NH-CHR4-C(O)- | R20 | R2 | R1 | Assay A |
|---|---|---|---|---|---|
| 554 | isobutyl-O-C(O)-NH-CH(iPr)-C(O)- | Ph | —CH2—CHF2 | 3,5-difluorophenyl-tetrazole | A |
| 555 | isobutyl-O-C(O)-NH-CH(iPr)-C(O)- | cyclohexyl | —CH2—CHF2 | 3,5-difluorophenyl-tetrazole | A |
| 556 | isobutyl-O-C(O)-NH-CH(iPr)-C(O)- | -SO2-cyclohexyl | —CH2—CHF2 | 3,5-difluorophenyl-tetrazole | A |
| 557 | isobutyl-O-C(O)-NH-CH(iPr)-C(O)- | cyclohexyl | —CH2—CHF2 | 3,5-difluorophenyl-C(O)NHSO2Me | A |
| 558 | isobutyl-O-C(O)-NH-CH(iPr)-C(O)- | Ph | —CH2—CHF2 | 3-(CH=CH-CO2H)phenyl | B |
| 559 | isobutyl-O-C(O)-NH-CH(iPr)-C(O)- | Ph | —CH2—CHF2 | 3-(CH=CH-CO2Et)phenyl | C |

TABLE 5-continued
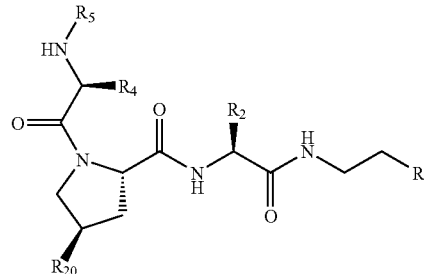
| No. | 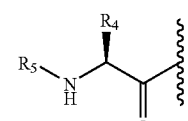 | $R_{20}$ | $R_2$ | $R_1$ | Assay A |
|---|---|---|---|---|---|
| 560 | 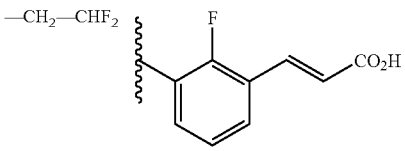 | Ph | —CH$_2$—CHF$_2$ | 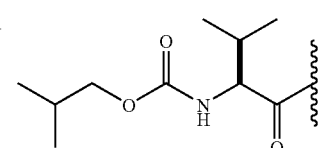 | A |
| 561 | 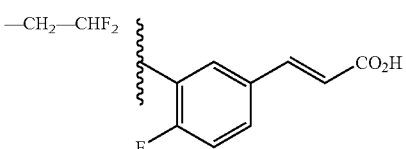 | Ph | —CH$_2$—CHF$_2$ | 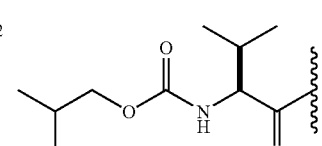 | A |
| 562 | 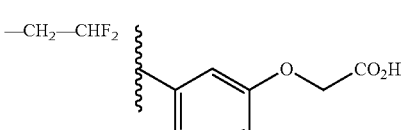 | Ph | —CH$_2$—CHF$_2$ | 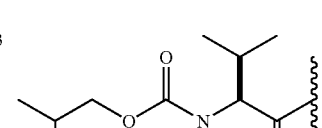 | C |
| 563 | 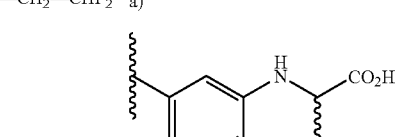 | Ph | —CH$_2$—CHF$_2$ a) | 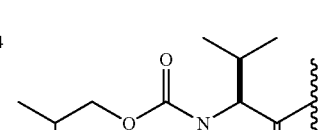 | B |
| 564 | 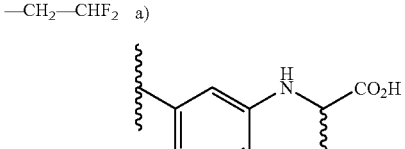 | Ph | —CH$_2$—CHF$_2$ a) | 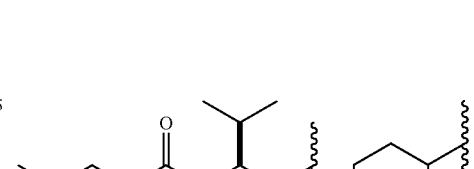 | B |
| 565 | 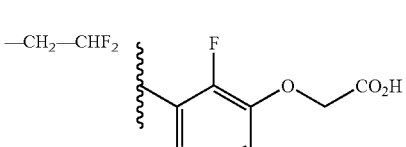 |  | —CH$_2$—CHF$_2$ | | A |

TABLE 5-continued

| No. | R5-NH-CHR4-C(O)- | R20 | R2 | R1 | Assay A |
|---|---|---|---|---|---|
| 566 | isobutyl carbamate-Val- | cyclohexyl | —CH2—CHF2 a) | 2,4-difluorophenoxy-CH(CO2H)- | A |
| 567 | neopentyl carbamate-Val- | cyclohexyl | —CH2—CHF2 a) | 2,4-difluorophenoxy-CH(CO2H)- | A |
| 568 | isobutyl carbamate-Val- | cyclohexyl | —CH2—CHF2 a) | 2,4-difluorophenoxy-CH(Et)(CO2H)- | A |
| 569 | isobutyl carbamate-Val- | Ph | —CH2—CHF2 a) | 3-phenoxy-CH(Ph)(CO2H)- | B |
| 570 | isobutyl carbamate-Val- | Ph | —CH2—CHF2 a) | 3-phenoxy-CH(4-BrPh)(CO2H)- | A |

TABLE 5-continued
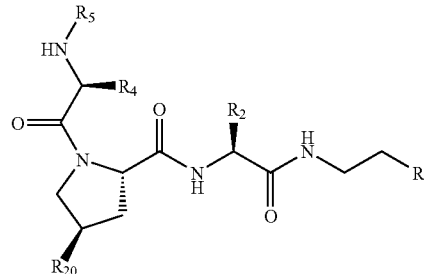
| No. | (R5-NH-CHR4-CO-) | R20 | R2 | R1 | Assay A |
|---|---|---|---|---|---|
| 571 | 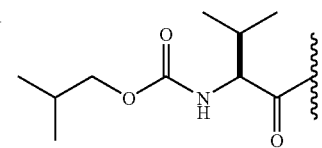 | Ph | —CH2—CHF2 a) | 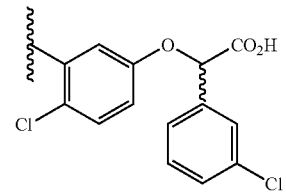 | B |
| 572 | 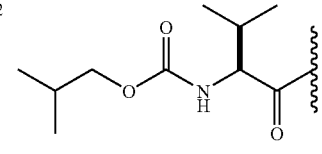 | Ph | —CH2—CHF2 | 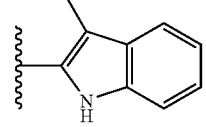 | C |
| 573 | 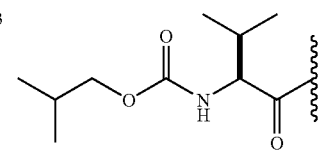 | Ph | —CH2—CHF2 | 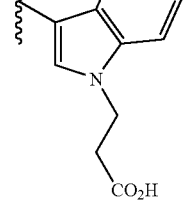 | C |
| 574 | 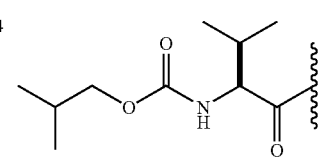 | Ph | —CH2—CHF2 | 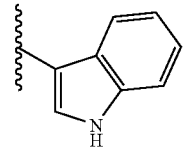 | C |
| 575 | 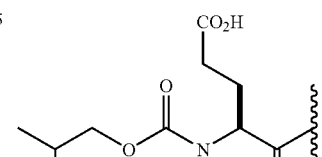 | Ph | —CH2—CHF2 | 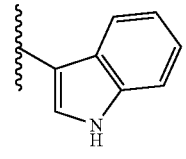 | C |

TABLE 5-continued
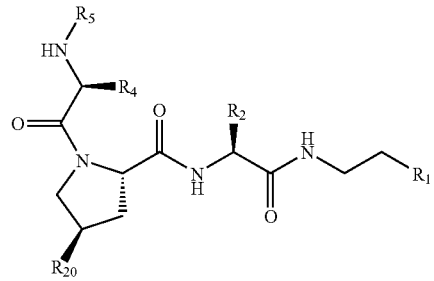
| No. | 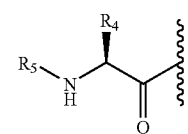 | $R_{20}$ | $R_2$ | $R_1$ | Assay A |
|---|---|---|---|---|---|
| 576 |  |  | —CH$_2$—CHF$_2$ | 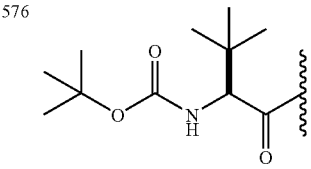 | A |
a) roughly 1:1 mixture of diastereomers; b) regio- and stereochemistry not determined; c) mixture of four diastereomers
TABLE 6
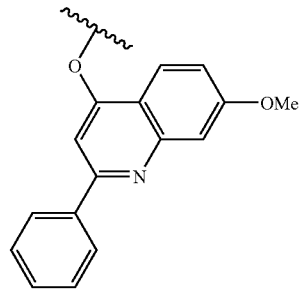
| No. | | $R_{17}$ |
|---|---|---|
| 601 |  | Ph |
| 602 | 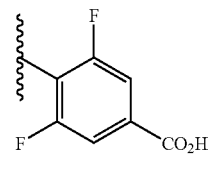 | Ph |
| 603 | 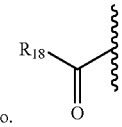 | Ph |
| 604 |  | Ph |

TABLE 6-continued

| | | |
|---|---|---|
| 605 | (thiophene-CH2-C(=O)-) | Ph |
| 606 b) | (3-thienyl-CH(CO2H)-CH2-C(=O)-) and (HO2C-CH2-CH(3-thienyl)-C(=O)-) | Ph |
| 607 | (4-pyridyl-CH2-C(=O)-) | Ph |
| 608 | (2-(CO2H)-C6H4-CH2-C(=O)-) | Ph |
| 609 | (2-(CO2H)-C6H4-CH2-C(=O)-) | Ph |
| 610 | (iPr-CH(OH)-C(=O)-) | Ph |
| 611 | (iPr-CH(OH)-C(=O)-) | Ph |
| 612 | (iPr-CH(OH)-C(=O)-) | Ph |
| 613 | (iPr-CH(OH)-C(=O)-) | Ph |

TABLE 6-continued
| | | |
|---|---|---|
| 614 | 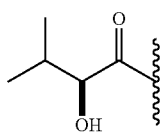 | 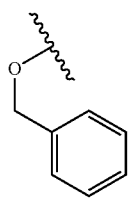 |
| 615 | 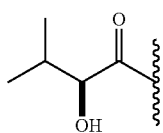 | 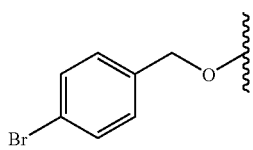 |
| 616 | 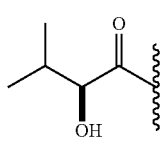 | Ph(CH$_2$)$_3$O |
| 617 | 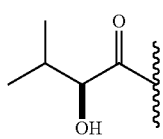 | 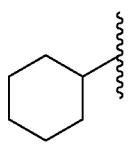 |
| 618 | 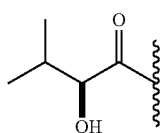 | 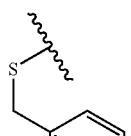 |
| 619 | 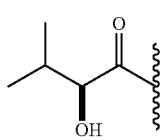 | 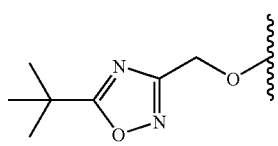 |
| 620 | 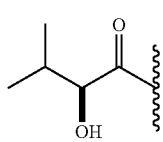 | 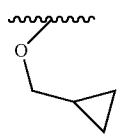 |
| 621 | 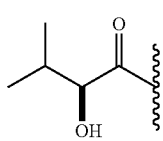 | 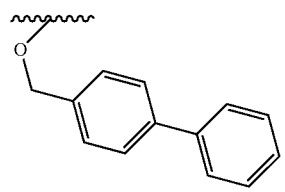 |
| 622 | 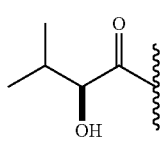 | OtBu |

TABLE 6-continued
| | | |
|---|---|---|
| 623 | 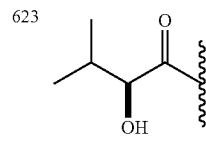 | 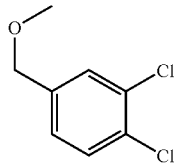 |
| 624 | 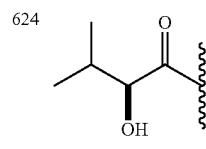 | 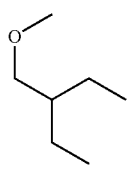 |
| 625 | 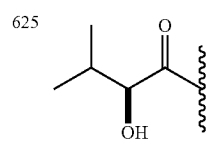 | 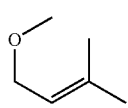 |
| 626 | 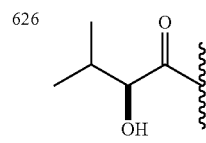 | 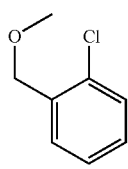 |
| 627 | 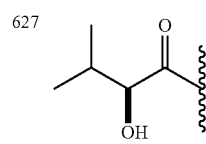 | 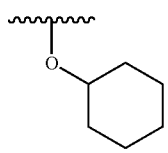 |
| 628 | 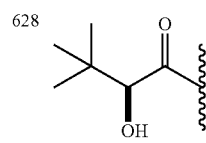 | Ph |
| 629 a) | 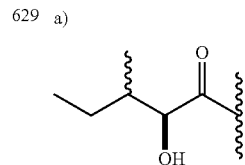 | Ph |
| 630 a) | 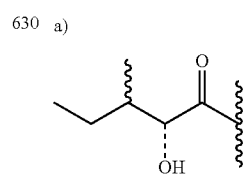 | Ph |
| 631 | 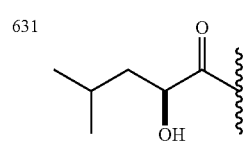 | Ph |

TABLE 6-continued
| No. | | | Ph |
|---|---|---|---|
| 632 a) | 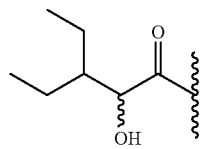 | | Ph |
| 633 c) | 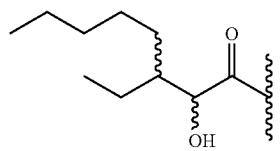 | | Ph |
| 634 a) | 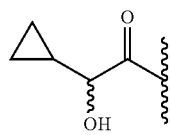 | | Ph |
| 635 | 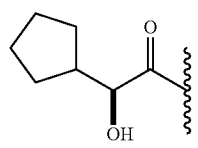 | | Ph |
| 636 | 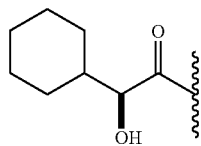 | | Ph |
| 637 | 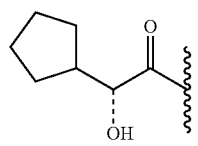 | | Ph |
| 638 | 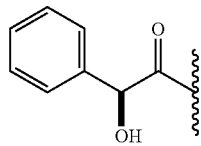 | | Ph |
| No. | $R_2$ | $R_1$ | Assay A |
|---|---|---|---|
| 601 | —CH$_2$—CHF$_2$ | 3,5-difluoro-4-yl-benzoic acid | C |
| 602 | —CH$_2$—CHF$_2$ | 3,5-difluoro-4-yl-benzoic acid | C |

TABLE 6-continued
| 603 | —CH₂—CHF₂ | 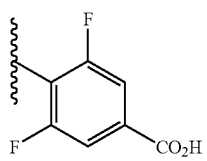 | C |
| 604 | —CH₂—CHF₂ | 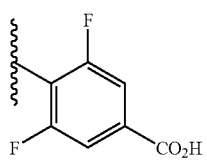 | C |
| 605 | —CH₂—CHF₂ | 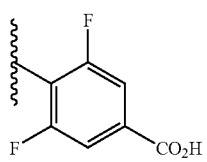 | C |
| 606 | —CH₂—CHF₂ | 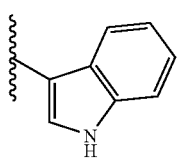 | C |
| 607 | —CH₂—CHF₂ | 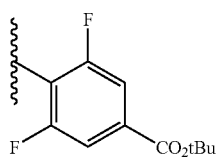 | C |
| 608 | —CH₂—CHF₂ | 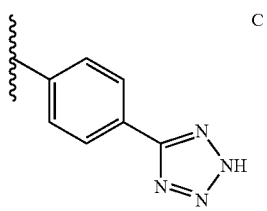 | C |
| 609 | —CH₂—CHF₂ | 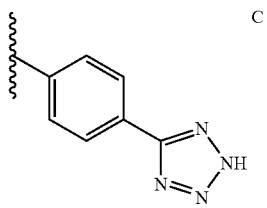 | C |
| 610 | —CH₂—CHF₂ | 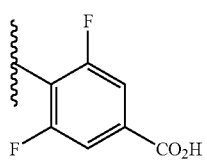 | C |

TABLE 6-continued
| 611 | —CH₂—CHF₂ | 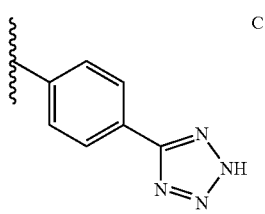 | C |
| 612 | —CH₂—CHF₂ |  | C |
| 613 | —CH₂—CHF₂ | 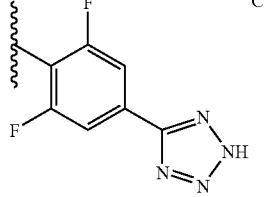 | C |
| 614 | —CH₂—CHF₂ | 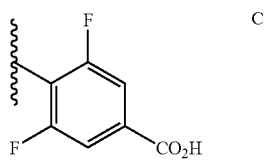 | C |
| 615 | —CH₂—CHF₂ | 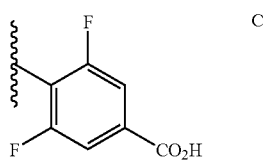 | C |
| 616 | —CH₂—CHF₂ | 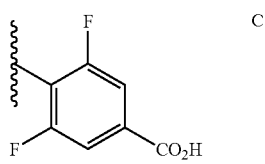 | C |
| 617 | —CH₂—CHF₂ | 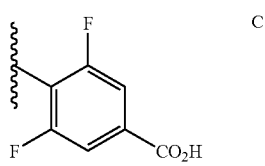 | C |
| 618 | —CH₂—CHF₂ | 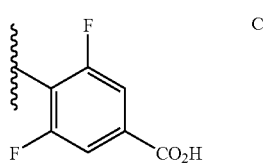 | C |

TABLE 6-continued
| 619 | —CH₂—CHF₂ | 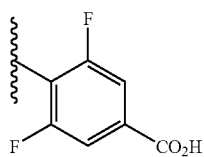 | C |
| 620 | —CH₂—CHF₂ | 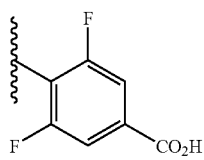 | C |
| 621 | —CH₂—CHF₂ | 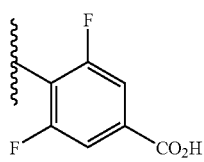 | C |
| 622 | —CH₂—CHF₂ | 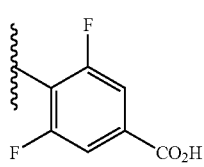 | C |
| 623 | —CH₂—CHF₂ | 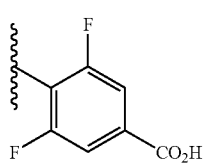 | C |
| 624 | —CH₂—CHF₂ | 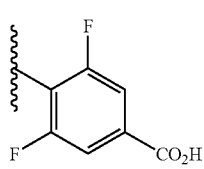 | C |
| 625 | —CH₂—CHF₂ | 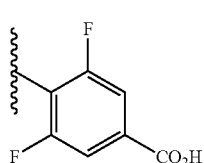 | C |
| 626 | —CH₂—CHF₂ | 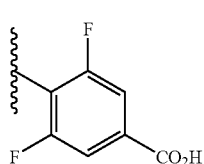 | C |
| 627 | —CH₂—CHF₂ | 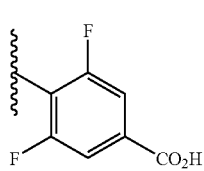 | C |

TABLE 6-continued
| | | | |
|---|---|---|---|
| 628 | —CH₂—CHF₂ | 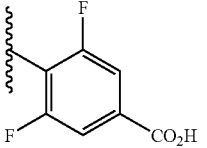 | C |
| 629 | —CH₂—CHF₂ | 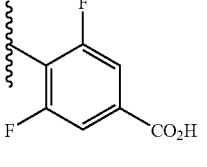 | C |
| 630 | —CH₂—CHF₂ | 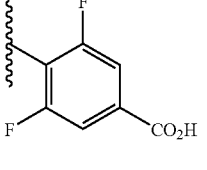 | C |
| 631 | —CH₂—CHF₂ | 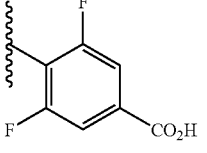 | C |
| 632 | —CH₂—CHF₂ | 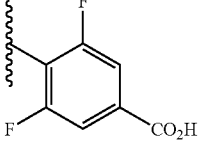 | C |
| 633 | —CH₂—CHF₂ | 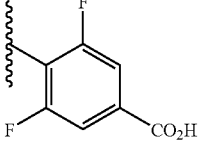 | C |
| 634 | —CH₂—CHF₂ | 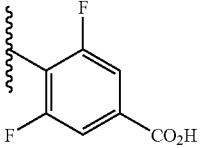 | C |
| 635 | —CH₂—CHF₂ | 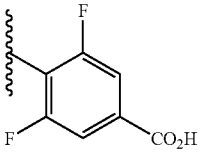 | C |
| 636 | —CH₂—CHF₂ | 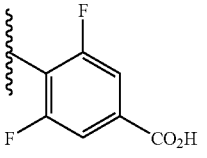 | C |

TABLE 6-continued

| 637 | —CH$_2$—CHF$_2$ | 3,5-difluoro-4-yl benzoic acid | C |
| 638 | —CH$_2$—CHF$_2$ | 3,5-difluoro-4-yl benzoic acid | C | a) roughly 1:1 mixture of diastereomers; b) regio- and stereochemistry not determined; c) mixture of four diastereomers

TABLE 7

| No. | R$_{13}$ | R$_2$ | R$_1$ | Assay A | Assay B |
|-----|----------|-------|-------|---------|---------|
| 701 | a) 2-(3-carboxybenzyl)indoline | —CH$_2$—SH | 4-carboxyphenyl | | C |
| 702 | b) 2-(4-carboxybenzyl)indoline | —CH$_2$—SH | 4-carboxyphenyl | C | C |
| 703 | a) 2-((5-carboxythiophen-2-yl)methyl)indoline | —CH$_2$—SH | 4-carboxyphenyl | | C |

TABLE 7-continued
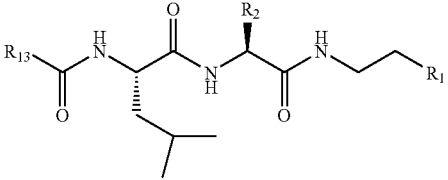
| No. | R13 | R2 | R1 | Assay A | Assay B |
|---|---|---|---|---|---|
| 704 | a) 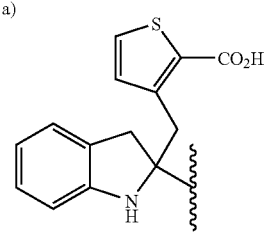 | —CH2—SH | 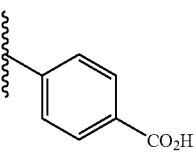 | | C |
| 705 | b) 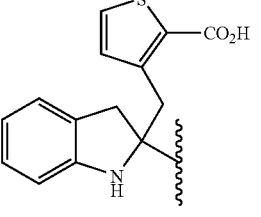 | —CH2—CHF2 | 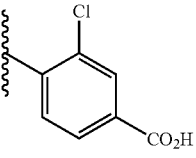 | C | B |
| 706 | b) 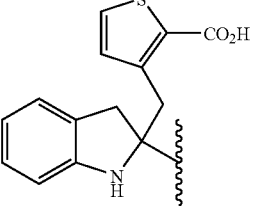 | —CH2—CHF2 | 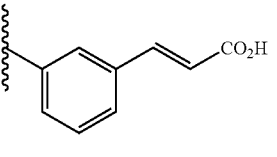 | C | B |
| 707a | b) 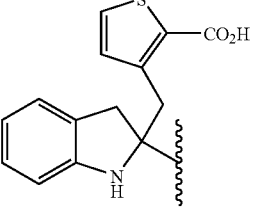 | —CH2—CHF2 | 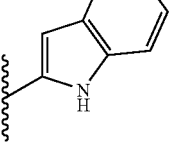 | | C |
| 707b | b) 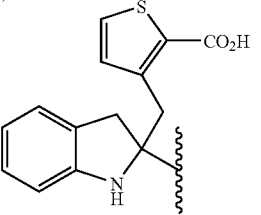 | —CH2—CHF2 | 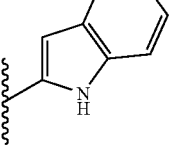 | | C |

TABLE 7-continued

| No. | R13 | R2 | R1 | Assay A | Assay B |
|---|---|---|---|---|---|
| 708a | b) [indoline-thiophene-CO2H] | —CH2—CHF2 | [difluorophenyl-CO2H] | | C |
| 708b | b) [indoline-thiophene-CO2H] | —CH2—CHF2 | [difluorophenyl-CO2H] | C | B |
| 709 | [indoline] | —CH2—CHF2 | [difluorophenyl-CO2H] | C | C |
| 710 | b) [tetrahydroquinoline-thiophene-CO2H] | —CH2—CHF2 | [chlorophenyl-CO2H] | C | B |
| 711a | b) [tetrahydroquinoline-thiophene-CO2H] | —CH2—CHF2 | [chlorophenyl-CO2H] | | C |

TABLE 7-continued

| No. | R13 | R2 | R1 | Assay A | Assay B |
|---|---|---|---|---|---|
| 711b | b) tetrahydroquinoline-CH2-thiophene-CO2H | —CH2—CHF2 | 4-Cl, 4-CO2H phenyl | C | B |
| 712a | b) tetrahydroquinoline-CH2-phenyl-3-CO2H | —CH2—CHF2 | 4-Cl, 4-CO2H phenyl | | C |
| 712b | b) tetrahydroquinoline-CH2-phenyl-3-CO2H | —CH2—CHF2 | 4-Cl, 4-CO2H phenyl | C | B |
| 713 | b) tetrahydroquinoline-CH2-thiophene-2-CO2H | —CH2—CHF2 | 3,5-diF, 4-CO2H phenyl | C | C |
| 714 | b) tetrahydroquinoline-CH2-thiophene-2-CO2H | —CH2—CHF2 | 3-(CH=CH-CO2H) phenyl | C | C |
| 715 | 2'-CO2H biphenyl | —CH2—CHF2 | 4-Cl, 4-CO2H phenyl | C | C |

TABLE 7-continued

| No. | R13 | R2 | R1 | Assay A | Assay B |
|---|---|---|---|---|---|
| 716 | 2-biphenyl-CO2H | —CH2—SH | 2-Cl-phenyl | C | C |
| 717 | 2-biphenyl-CO2H | —CH2—SH | 2,4-diCl-phenyl | C | C |
| 718 | 2-biphenyl-CO2H | —CH2—CHF2 | 3,5-diF-4-CO2H-phenyl | C | C |
| 719 | 2-biphenyl-CO2H | —CH2—CHF2 | 3-(CH=CH-CO2Et)-phenyl | C | C |
| 720 | 2-biphenyl-CO2H | —CH2—CHF2 | 3-(NH-CH2-CO2H)-phenyl | C | C |
| 721 | 2-biphenyl-CO2H | —CH2—CHF2 | 3-(NH-CH2-CO2Et)-phenyl | C | C | a) mixture of diastereomers at indoline (1:1 to 3:1);
b) single diastereomer

The invention claimed is:

1. A compound of Formula (I), or a pharmaceutically acceptable salt or ester thereof:

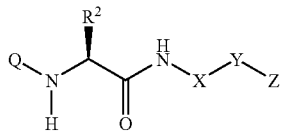

(I)

wherein Q is:

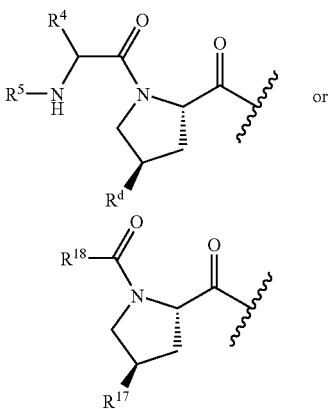

wherein X is —CH$_2$— or —O—;
Y is a group of formula —C(R$^a$)$_2$— where each R$^a$ is independently selected from hydrogen, hydroxyl, carboxylic acid, lower alkyl, aryl, heteroaryl, aralkyl and heteroalkyl, or the two R$^a$ groups together form a cycloalkyl group containing 3 to 7 carbon atoms;
Z is a substituted or unsubstituted aryl or heteroaryl group;
R$^2$ is a lower alkyl group, optionally substituted with one or more fluorine atoms, or is —CH$_2$SH;
R$^d$ is hydrogen, lower alkyl, lower alkenyl, aryl, heteroaryl, aralkyl, heteroaralkyl, hydroxyl, alkoxy, aryloxy, heteroaryloxy, aralkoxy, heteroaralkoxy, thioether, sulfonyl or sulfoxide;
R$^4$ is an alkyl, alkenyl, aralkyl, heteroaralkyl, aryl or heteroaryl group containing from 2 to 16 carbon atoms or is an acidic group;
R$^5$ selected from (R$^6$)$_2$NCO—, R$^7$CO—, R$^7$OCO—, R$^7$NHCO—, R$^7$CO.CO—, R$^7$S(O)$_2$— and R$^8$ pep;
each R$^6$, independently, is selected from hydrogen and optionally substituted, optionally interrupted lower alkyl or lower alkenyl, aryl, heteroaryl, aralkyl or heteroaralkyl groups, or the two R$^6$ taken together form a four to seven membered ring optionally containing one or more other heteroatoms in addition to the nitrogen atoms to which the R$^6$ groups are bonded;
R$^7$ is an optionally substituted, optionally interrupted alkyl, alkenyl, aralkyl, heteroaralkyl, aryl or heteroaryl group containing from 1–18 carbon atoms;
R$^8$ is a group of formula (R$^6$)$_2$NCO—, R$^7$CO—, R$^7$OCO—, R$^7$NHCO—, R$^7$ COCO—, or R$^7$ S(O)$_2$—;
"pep" if present is an amino acid, di, or tri peptide of formula C-B-A;

wherein A is selected from naturally and non-naturally occurring amino acids having a hydrophobic side chain containing 1–20 carbon atoms;
B is optionally absent, in which case C will also be absent, but if present is selected from naturally and non-naturally occurring amino acids having a side chain which includes an acidic functionality;
C is optionally absent, either by itself or together with B, but if present is selected from naturally and non-naturally occurring amino acids containing an acidic functionality;
R$^{17}$ is hydrogen, a lower alkyl, lower alkenyl, aryl, heteroaryl, aralkyl, heteroaralkyl, hydroxyl, alkoxy, aryloxy, aralkoxy, heteroaralkoxy, thioether, sulfonyl or sulfoxide group;
R$^{18}$ is:

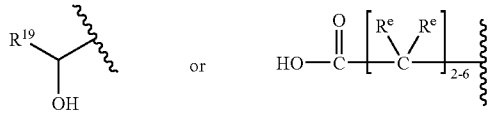

R$^{19}$ is alkyl, C$_3$–C$_7$ cycloalkyl, or optionally substituted aryl; and
each R$^e$ is independently hydrogen, lower alkyl, lower alkenyl, lower alkoxy, optionally substituted aryl, heteroaryl, aralkyl or heteroaralkyl; or two R$^e$ taken together form a three to seven membered aliphatic or aromatic ring which optionally contains at least one heteroatom, wherein when two R$^e$ are taken together in the formation of a ring containing unsaturation, then other R$^e$ may be absent.

2. A compound as claimed in claim 1 represented by the formula:

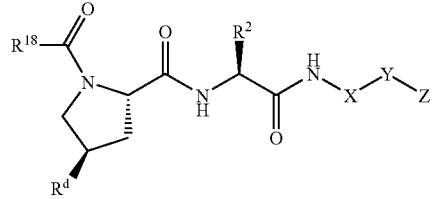

or a pharmaceutically acceptable salt or ester thereof.

3. A compound according to claim 1, which is:

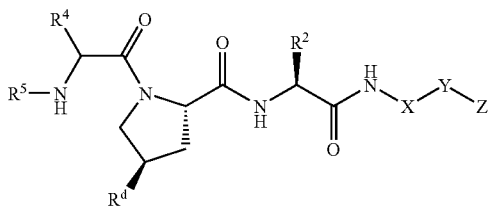

or a pharmaceutically acceptable salt or ester thereof.

4. A compound according to claim 1, or a pharmaceutically acceptable salt or ester thereof, which is a compound as depicted in Table 5 or Table 6.

5. A compound according to claim 3, or a pharmaceutically acceptable salt or ester thereof, wherein —X—Y— is —OCH$_2$— or —CH$_2$CH$_2$—.

6. A compound according to claim 3, or a pharmaceutically acceptable salt or ester thereof, wherein Z is a substituted or unsubstituted phenyl, indolyl, thienyl, naphthyl, or pyridyl.

7. A compound according to claim 3, or a pharmaceutically acceptable salt or ester thereof, wherein $R^d$ is phenyl, cyclohexyl, benzyl ether, benzyl thioether, or a thioether or sulfone or sulfoxide formed with phenyl, cyclohexyl or n-propyl.

8. A compound according to claim 3, or a pharmaceutically acceptable salt or ester thereof, wherein $R^4$ is lower alkyl, cyclopentyl, or t-butyl, or is carboxyalkyl containing from 2 to 8 carbon atoms.

9. A compound according to claim 3, or a pharmaceutically acceptable salt or ester thereof, wherein $R^5$ is $R^7OCO-$.

10. A compound according to claim 3, or a pharmaceutically acceptable salt or ester thereof, wherein $R^7$ is an optionally substituted, optionally interrupted alkyl, alkenyl, aralkyl, heteroaralkyl, aryl or heteroaryl group containing from 1 to 8 carbon atoms.

11. A compound according to claim 10, or a pharmaceutically acceptable salt or ester thereof, wherein $R^7$ is t-butyl or isobutyl.

12. A compound according to claim 2, or a pharmaceutically acceptable salt or ester thereof, wherein $-X-Y-$ is $-OCH_2-$ or $-CH_2CH_2-$.

13. A compound according to claim 2, or a pharmaceutically acceptable salt or ester thereof, wherein Z is a substituted or unsubstituted phenyl, indolyl, thienyl, naphthyl, or pyridyl.

14. A compound according to claim 2, or a pharmaceutically acceptable salt or ester thereof, wherein X and Y are both $CH_2$; $R^2$ is $CH_2CHF_2$ or $CH_2SH$; and Z is 2,6-difluoro-4-carboxy-phenyl-.

15. A compound according to claim 2, or a pharmaceutically acceptable salt or ester thereof, wherein $R^{17}$ is phenyl, cyclohexyl, benzyl ether, benzyl thioether, or a thioether or sulfone or sulfoxide formed with phenyl, cyclohexyl or n-propyl.

16. A compound according to claim 2, or a pharmaceutically acceptable salt or ester thereof, wherein $R^{18\ is}$

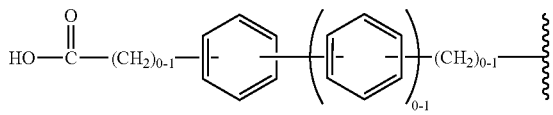

wherein the carboxylic acid group is optionally esterified to a lower alkyl ester.

17. A pharmaceutical composition comprising a compound of formula (I) as defined in claim 1, or a pharmaceutically acceptable salt or ester thereof, in association with a pharmaceutically acceptable carrier.

18. A process for the preparation of a compound of formula (I) as defined in claim 1, which comprises reacting protected form of the P1 amino acid:

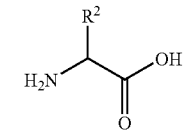

with a compound of formula $H_2N-X-Y-Z$; and subsequently extending towards the N-terminus.

19. A method of inhibiting HCV NS3 protease activity, which comprises administering to a subject in need of such inhibition a therapeutically effective amount of a compound of formula (I) as defined in claim 1, or a pharmaceutically acceptable salt or ester thereof.

20. A method for treating hepatitis C, which comprises administering to a subject in need of such treatment a compound of formula (I) as defined in claim 1, or a pharmaceutically acceptable salt or ester thereof.

* * * * *

UNITED STATES PATENT AND TRADEMARK OFFICE
CERTIFICATE OF CORRECTION

PATENT NO. : 7,119,073 B2  
APPLICATION NO. : 10/473443  
DATED : October 10, 2006  
INVENTOR(S) : Stefania Colarusso et al.

It is certified that error appears in the above-identified patent and that said Letters Patent is hereby corrected as shown below:

Title page, column 1:     Please delete from Item (75) Inventors the following: "Steven Harper, Pomezia (IT);":

Title page, column 1:     In Item (75) Inventors, please replace "Vicenzo Summa" with --Vincenzo Summa--.

Signed and Sealed this

Twenty-fourth Day of June, 2008

JON W. DUDAS  
*Director of the United States Patent and Trademark Office*